United States Patent
Yen et al.

(10) Patent No.: US 10,577,328 B2
(45) Date of Patent: Mar. 3, 2020

(54) AMINONAPTHOQUINONE COMPOUNDS AND PHARMACEUTICAL COMPOSITION FOR BLOCKING UBIQUITINATION-PROTEASOME SYSTEM IN DISEASES

(71) Applicant: TAIPEI MEDICAL UNIVERSITY, Taipei (TW)

(72) Inventors: Yun Yen, Arcadia, CA (US); Jing-ping Liou, Taipei (TW); Shiow-lin Pan, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 15/746,964

(22) PCT Filed: Jul. 23, 2015

(86) PCT No.: PCT/US2015/041767
§ 371 (c)(1),
(2) Date: Jan. 23, 2018

(87) PCT Pub. No.: WO2017/014788
PCT Pub. Date: Jan. 26, 2017

(65) Prior Publication Data
US 2018/0319749 A1    Nov. 8, 2018

(51) Int. Cl.
| | |
|---|---|
| C07D 213/75 | (2006.01) |
| C07D 213/74 | (2006.01) |
| A61P 37/00 | (2006.01) |
| A61P 25/28 | (2006.01) |
| A61P 35/02 | (2006.01) |
| A61P 3/10 | (2006.01) |
| C07D 209/04 | (2006.01) |
| C07D 215/40 | (2006.01) |
| C07D 215/42 | (2006.01) |
| C07D 231/38 | (2006.01) |
| C07D 235/30 | (2006.01) |
| C07D 239/42 | (2006.01) |
| C07D 241/04 | (2006.01) |
| C07D 241/20 | (2006.01) |
| C07D 277/42 | (2006.01) |
| C07D 471/04 | (2006.01) |
| C07D 487/04 | (2006.01) |
| A61K 31/337 | (2006.01) |
| A61K 31/475 | (2006.01) |
| A61K 31/506 | (2006.01) |
| A61K 31/593 | (2006.01) |
| A61K 31/704 | (2006.01) |
| A61K 33/24 | (2019.01) |

(52) U.S. Cl.
CPC .............. *C07D 213/75* (2013.01); *A61P 3/10* (2018.01); *A61P 25/28* (2018.01); *A61P 35/02* (2018.01); *A61P 37/00* (2018.01); *C07D 209/04* (2013.01); *C07D 213/74* (2013.01); *C07D 215/40* (2013.01); *C07D 215/42* (2013.01); *C07D 231/38* (2013.01); *C07D 235/30* (2013.01); *C07D 239/42* (2013.01); *C07D 241/04* (2013.01); *C07D 241/20* (2013.01); *C07D 277/42* (2013.01); *C07D 471/04* (2013.01); *C07D 487/04* (2013.01); *A61K 31/337* (2013.01); *A61K 31/475* (2013.01); *A61K 31/506* (2013.01); *A61K 31/593* (2013.01); *A61K 31/704* (2013.01); *A61K 33/24* (2013.01); *A61K 2300/00* (2013.01)

(58) Field of Classification Search
CPC .. C07D 209/04; C07D 213/74; C07D 213/75; C07D 213/76; C07D 215/40; C07D 215/42; C07D 231/38; C07D 235/30; C07D 239/42; C07D 241/04; C07D 241/20; C07D 277/42; C07D 471/04; C07D 487/04
See application file for complete search history.

(56) References Cited

U.S. PATENT DOCUMENTS

| | | | |
|---|---|---|---|
| 7,442,830 B1 | 10/2008 | Olhava | |
| 8,003,819 B2 | 8/2011 | Olhava | |

(Continued)

FOREIGN PATENT DOCUMENTS

| | | |
|---|---|---|
| KR | 2013-0101908 A | 9/2013 |
| WO | 2006/011136 A2 | 2/2006 |

(Continued)

OTHER PUBLICATIONS

Carroll et al. (J. Med. Chem. (1969), 12(1), 187-189).*

(Continued)

*Primary Examiner* — Valerie Rodriguez-Garcia
(74) *Attorney, Agent, or Firm* — Duane Morris LLP

(57) ABSTRACT

The invention relates to a compound of formula (I)

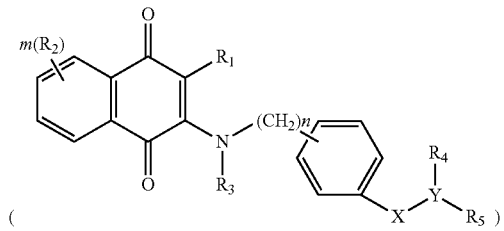

with low cytotoxicity for blocking the ubiquitination-proteasome system in diseases. Accordingly, these compounds can be used in treatment of disorders including, but not limited to, multiple myeloma, cancers, neurodegenerative diseases, inflammatory disorders, autoimmune disorders and metabolic disorders.

11 Claims, 17 Drawing Sheets

(56) References Cited

U.S. PATENT DOCUMENTS

| | | | |
|---|---|---|---|
| 8,058,262 | B2 | 11/2011 | Bernardini |
| 8,389,564 | B2 | 3/2013 | Macherla |
| 2004/0167189 | A1 | 8/2004 | Bulavin et al. |
| 2006/0193844 | A1 | 8/2006 | Bennett et al. |
| 2008/0300274 | A1 | 12/2008 | Granot |
| 2010/0240581 | A1 | 9/2010 | Tortoriello et al. |
| 2011/0201609 | A1 | 8/2011 | Lawrence et al. |
| 2013/0071353 | A1 | 3/2013 | Guenther |
| 2014/0213627 | A1 | 7/2014 | Scherzer et al. |

FOREIGN PATENT DOCUMENTS

| | | |
|---|---|---|
| WO | 2010/005534 A2 | 1/2010 |
| WO | 2014074976 A1 | 5/2014 |
| WO | 2017/014788 A1 | 1/2017 |

OTHER PUBLICATIONS

Wolff, Manfred E. "Burger's Medicinal Chemistry, 5ed, Part I", John Wiley & Sons, 1995, pp. 975-977).*

Jordan, V. C. Nature Reviews: Drug Discovery, 2, 2003, pp. 205-213.*

Dörwald, F. Zaragoza. Side Reactions in Organic Synthesis: A Guide to Successful Synthesis Design, Weinheim: WILEY-VCH Verlag GmbH & Co. KGaA, 2005, Preface.*

Tumor definition in National Cancer Institute—www.cancer.gov (May 22, 2014).*

Cancer definition in MedicineNet.com—(Sep. 16, 2005).*

Stomach cancer—Mayoclinic.com—Apr. 9, 2011.*

"Adult Brain Tumors Treatment", National Cancer Institute, pp. 1-21 (Jan. 24, 2013).*

"Types of Brain Cancer" at http://www.cancercenter.com/brain-cancer/types-of-brain-cancer.cfm (Mar. 12, 2013).*

"Colorectal Cancer" at cancer.net (published Sep. 2012).*

"Types of Breast Cancer", published in breastcancer.org (Sep. 30, 2012).*

Cancer Drug Design and Discovery Neidle, Stephen, ed. (Elsevier/Academic Press, 2008).*

Johnson et al. (British J. of Cancer, 2001, 84(10):1424-1431).*

Lens (Br. J. Nurs., 2008, vol. 17, No. 5, pp. 300-305).*

Divers et al. (Cutis. 2004, vol. 73, No. 4, pp. 257-262).*

Translation of Office Action dated Dec. 22, 2018, from corresponding Taiwan Patent Application No. 105123321, 3 total pages.

Patani GA, LaVoie EJ. "Bioisosterism: a rational approach in drug design" Chem. Rev. 1996, 96(8), 3147-3176.

Berge, S. M. et al., Pharmaceutical salts, J. Pharm. Sci., (1977), 66,1-19.

Biswas A, Mukherjee S, Das S, Shields D, Chow CW, Maitra U. (2011). Opposing action of casein kinase 1 and calcineurin in nucleo-cytoplasmic shuttling of mammalian translation initiation factor eIF6. Journal of Biological Chemistry, 286 (4): 3129-38.

Bode AM, Dong Z. (2007) The Functional Contrariety of JNK. Mol. Carcinog. 46 (8): 591-8.

Chang L, Kamata H, Solinas G, Luo JL, Maeda S, Venuprasad K, Liu YC, and Karin M. The E3 ubiquitin ligase itch couples JNK activation to TNFalpha-induced cell death by inducing c-FLIP(L) turnover, Cell. Feb. 10, 2006;124(3):601-13.

Eun Kyung Kim, Eui-Ju Choi. (2010) Pathological roles of MAPK signaling pathways in human diseases. Biochimica et Biophysica Acta. 1802: 396-405.

Ferrer, Isidre; Mohan, Pooja; Chen, Helen; Castellsague, Joan; Gómez-Baldó, Laia; Carmona, Marga; García, Nadia; Aguilar, Helena; Jiang, Jihong; Skowron, Margaretha; Nellist, Mark; Ampuero, Israel; Russi, Antonio; Lázaro, Conxi; Maxwell, Christopher A; Pujana, Miguel Angel. (2014). Tubers from patients with tuberous sclerosis complex are characterized by changes in microtubule biology through ROCK2 signalling. The Journal of Pathology, 233(3): 247-57.

Graeser R, Gannon J, Poon RY, Dubois T, Aitken A, Hunt T. (2002) Regulation of the CDK-related protein kinase PCTAIRE-1 and its possible role in neurite outgrowth in Neuro-2A cells. J. Cell. Sci., 115: 3479-90.

Keramati, M.D., Ali R., Mohsen Fathzadeh, Ph.D., Gwang-Woong GO, Ph.D., Rajvir Singh, Ph.D., Murim Choi, Ph.D., Saeed Faramarzi, M.D., Shrikant Mane, Ph.D., Mohammad Kasaei, M.D., Kazem Sarajzadeh-Fard, M.D., John Hwa, M.D., Ph.D., Kenneth K. Kidd, Ph.D., Mohammad A. Babaee Bigi, M.D., Reza Malekzadeh, M.D., Adallat Hosseinian, M.D., Masoud Babaei, M.D., Richard P. Lifton, M.D., Ph.D., and Arya Mani, M.D. (2014) A Form of the Metabolic Syndrome Associated with Mutations in DYRK1B.

Kim-Ann Saal, Jan C. Koch, Lars Tatenhorst, Éva M. Szegö, Vinicius Toledo Ribas, Uwe Michel, Mathias Bähr, Lars Tönges, Paul Lingor. (2015) AAV.shRNA mediated downregulation of ROCK2 attenuates degeneration of dopaminergic neurons in toxininduced models of Parkinson's disease in vitro and in vivo. Neurobiology of Disease, (73):150-162.

Lee H, Chen R, Lee Y, Yoo S, Lee C, (2009) Essential roles of CKI and CKI in the mammalian circadian clock. PNAS, 106 (50): 21359-64.

Lin Yao, Surabhi Chandra , Haroldo A. Toque, Anil Bhatta, Modesto Rojas, Ruth B. Caldwell, R. William Caldwell, (2013) Prevention of diabetesinduced arginase activation and vascular dysfunction by Rho kinase (ROCK) knockout. Cardiovascular Research, 97, 509-519.

Liu T, Deng M. Li J, Tong X, Wei Q, Ye X. (2011) Phosphorylation of right open reading frame 2 (Rio2) protein kinase by polo-like kinase 1 regulates mitotic progression. J Biol Chem, 286(42):36352-60.

Read RD, Fenton TR, Gomez GG, Wykosky J, Vandenberg SR, Babic I, Iwanami A, Yang H, Cavenee WK, Mischel PS, Furnari FB, Thomas JB. (2013) A kinome-wide RNAi screen in Drosophila glia reveals that the RIO kinases mediate cell proliferation and survival through TORC2-Akt signaling in glioblastoma. PLoS Genet, 9(2): e1003253.

Remington's Pharmaceutical Sciences, Gennaro, Ed., Mack Publishing Co., Easton, Pa. 1990.

Scialpi F, Malatesta M, Peschiaroli A, Rossi M, Melino G, and Bernassola F. Itch selfpolyubiquitylation occurs through lysine-63 linkages. Biochem Pharmacol. Dec. 1, 2008;76(11):1515-21

Tönges L, Frank T et al. (2012) Inhibition of rho kinase enhances survival of dopaminergic neurons and attenuates axonal loss in a mouse model of Parkinson's disease. Brain, 135 (11): 3355-70.

Extended European Search Report dated Feb. 5, 2019, from corresponding European Patent Application No. 15899099.4, 6 total pages.

Carroll, F. Ivy, Kenneth H. Dudley, and H. Wayne Miller. "Preparation of some sulfonamide and diaminodiphenyl sulfone analogs of 1, 4-naphthoquinone." Journal of Medicinal Chemistry 12.1 (1969): 187-189.

Japan Office Action dated Jul. 18, 2019, from corresponding Japan Patent Application No. 2018-503202, with translation, 12 total pages.

Kazi, Aslamuzzaman, et al. "Discovery of a novel proteasome inhibitor selective for cancer over non-transformed cells." Cell Cycle 8.12 (2009): 1940-1951.

Lawrence, Harshani R., et al. "Synthesis and biological evaluation of naphthoquinone analogs as a novel class of proteasome inhibitors." Bioorganic & Medicinal Chemistry 18.15 (2010): 5576-5592.

Roushdi, I. M., A. A. Mikhail, and I. Chaaban. "Synthesis of substituted benzoquinones and naphthoquinones with potential antituberculous activity." Die Pharmazie 32.5 (1977): 269-270.

Xu, Kai, et al. "Design and synthesis of naphthoquinone derivatives as antiproliferative agents and 20S proteasome inhibitors." Bioorganic & Medicinal Chemistry Letters 22.8 (2012): 2772-2774.

Xu, Guanhong, Zhou Zhou, and Fei Li. "Combined Three Dimensional Quantitative Structure Activity Relationships (3D-QSAR) Modeling and Molecular Docking Studies on Naphthoquinone Analogs as Proteasome Inhibitors." Letters in Drug Design & Discovery 10.2 (2013): 129-144.

* cited by examiner

AMINONAPTHOQUINONE COMPOUNDS AND PHARMACEUTICAL COMPOSITION FOR BLOCKING UBIQUITINATION-PROTEASOME SYSTEM IN DISEASES

CROSS-REFERENCE TO RELATED APPLICATION

This application is a § 371 national stage entry of International Application No. PCT/US2015/041767, filed Jul. 23, 2015, the entire contents of which are incorporated herein by reference.

FIELD OF THE INVENTION

The present invention relates to the identification of new drug targets for therapy of disorders. In particular, the present invention relates to new drug targets with low cytotoxicity for blocking the ubiquitination-proteasome system in diseases.

BACKGROUND OF THE INVENTION

Cancer is a disease in which cells in the body grow out of control. The majority of current cancer treatment methods result in severe general toxicity to the human body. Both radiation and chemotherapy have deleterious effects to the host, causing significant morbidity and mortality. Hence, there is a need in the art for non-invasive and non-toxic methods of treating cancer and preventing tumor growth. However, the cancer cannot be effectively cured. Therefore, there is a need to develop a compound for effectively treating a cancer but having low cytotoxicity.

Inflammation is a mechanism that protects mammals from invading pathogens. However, while transient inflammation is necessary to protect a mammal from infection, uncontrolled inflammation causes tissue damage and is the underlying cause of many illnesses. Inflammation is typically initiated by binding of an antigen to T-cell antigen receptor. Antigen binding by a T-cell initiates calcium influx into the cell via calcium ion channels, such as $Ca^{2+}$-release-activated $Ca^{2+}$ channels (CRAC). Calcium ion influx in turn initiates a signaling cascade that leads to activation of these cells and an inflammatory response characterized by cytokine production. Overproduction of proinflammatory cytokines other than IL-2 has also been implicated in many autoimmune diseases. Therefore, there is a continuing need for new drugs which overcome one or more of the shortcomings of drugs currently used for the treatment or prevention of inflammatory disorders, allergic disorders and autoimmune disorders.

Proteasomes are part of a major mechanism by which cells regulate the concentration of particular proteins and degrade misfolded proteins. Proteasomes are large ring- or cylinder-shaped multicomponent complexes common to all eukaryotic cells. Proteasomes are large multi-subunit protease complexes, localized in the nucleus and cytosol, which selectively degrade intracellular proteins. Proteasomes play a major role in the degradation of many proteins that are involved in cell cycling, proliferation, and apoptosis. They have at least three distinct endopeptidase activities, which include hydrolysis of peptide bonds on the carboxyl side of hydrophobic, basic, and acidic amino acid residues. Proteasomes, through their protein degradation activity, have been implicated in several important cell functions, including DNA repair, cell cycle progression, signal transduction, transcription, and antigen presentation.

Proteasome inhibition represents an important new strategy in cancer treatment. U.S. Pat. Nos. 7,442,830, 8,003,819 and 8,058,262 relate to boronic acid and boronic ester compounds useful as proteasome inhibitors. U.S. Pat. No. 8,389,564 provides salinosporamide used for treating and/or ameliorating a disease or condition, such as cancer, a microbial disease and/or inflammation. WO 2010/005534 provides compounds having activity as inhibitors of proteasomes.

However, there is an ongoing need for new and/or improved inhibitors of proteasome.

SUMMARY OF THE INVENTION

One aspect of the invention is to provide a compound having the following Formula (I):

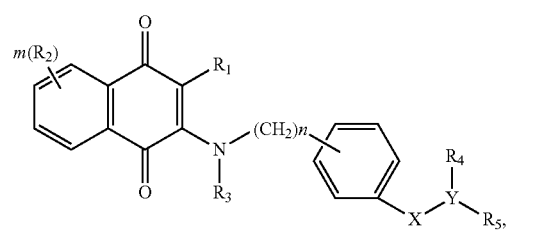

(I)

or a tautomer, stereoisomer or enantiomer thereof, or a solvate, prodrug or a pharmaceutically acceptable salt thereof.

Another aspect of the invention is to provide a pharmaceutical composition containing a compound of Formula (I).

A further aspect is to provide a method for inhibiting ITCH E3 ligase, comprising administrating a compound of Formula (I) to a cell or a subject.

Another further aspect is to provide a method for treating a cancer, comprising administrating a compound of Formula (I) to a cell or a subject.

Another further aspect is to provide a method for treating autoimmune disorders, comprising administrating a compound of Formula (I) to a cell or a subject.

DETAILED DESCRIPTION OF THE INVENTION

Figure 1:
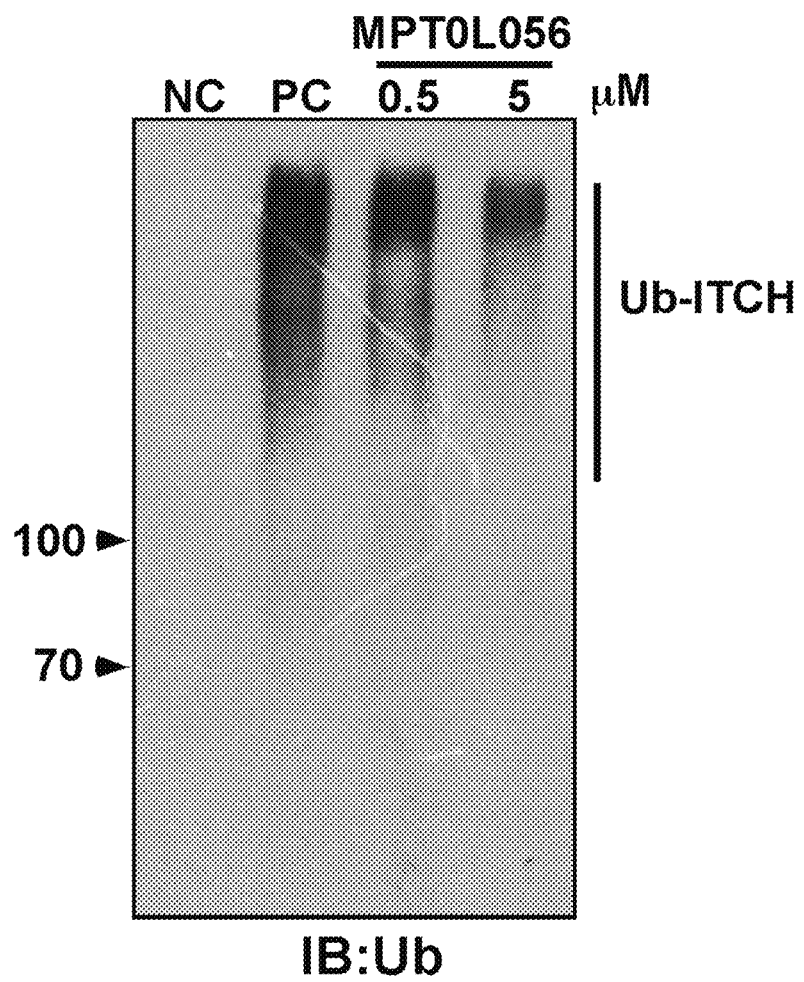
FIG. 1 shows that MPT0L056 of the invention blocks ITCH self-ubiquitination efficiently.

The invention relates to new compounds with low cytotoxicity for blocking the ubiquitination-proteasome system in diseases. Accordingly, these compounds can be used to treat disorders including, but not limited to, cancers, inflammatory disorders and autoimmune disorders.

Definitions and Terms

Terms not specifically defined herein should be understood according to the meanings that would be given to them by one of skill in the art in light of the disclosure and the context. As used in the specification, however, unless specified to the contrary, the following terms have the meaning indicated according to the following conventions.

The terms "a" and "an" refer to one or more.

The terms "disease" and "disorder" herein can be used interchangeably.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compounds, compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The term "substituted" as used herein means that any one or more hydrogens on the designated atom, radical or moiety is replaced with a selection from the indicated group, provided that the atom's normal valence is not exceeded, and that the substitution results in an acceptably stable compound.

The term "pharmaceutically acceptable" is employed herein to refer to those compounds, materials, compositions, and/or dosage forms which are, within the scope of medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines, pyridine, pyrimidine and quinazoline; alkali or organic salts of acidic residues such as carboxylic acids; and the like.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active, wherein the enantiomer rotates the plane of polarized light in one direction and its mirror image compound rotates the plane of polarized light in the opposite direction.

The term "racemic" refers to a mixture of equal parts of enantiomers that is optically inactive.

The term "resolution" refers to the separation or concentration or depletion of one of the two enantiomeric forms of a molecule.

As used herein, halo or halogen refers to fluoro, chloro, bromo or iodo.

As used herein, the term "alkyl" refers to straight or branched hydrocarbon chains containing the specified number of carbon atoms. For example, "$C_1$-$C_6$ alkyl" is selected from straight-chained and branched non-cyclic hydrocarbons having from 1 to 6 carbon atoms. Representative straight chain $C_1$-$C_6$ alkyl groups include -methyl, -ethyl, -n-propyl, -n-butyl, -n-pentyl, and -n-hexyl. Representative branched $C_1$-$C_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

As used herein, the term "alkenyl" refers to straight or branched chain hydrocarbon chains containing the specified number of carbon atoms and one or more double bonds. For example, "$C_2$-$C_6$ alkenyl" is selected from straight chain and branched non-cyclic hydrocarbons having from 2 to 6 carbon atoms and including at least one carbon-carbon double bond. Representative straight chain and branched $C_2$-$C_6$ alkenyl groups include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, 2-hexenyl, and 3-hexenyl.

As used herein, the term "alkynyl" refers to straight or branched chain hydrocarbon chains containing the specified number of carbon atoms and one or more triple bonds. For example, "$C_2$-$C_6$ alkynyl" is selected from straight chain and branched non-cyclic hydrocarbon having from 2 to 6 carbon atoms and including at least one carbon-carbon triple bond.

Representative straight chain and branched $C_2$-$C_6$ alkynyl groups include -acetylenyl, -propynyl, -1-butyryl, -2-butyryl, -1-pentynyl, -2-pentynyl, -3-methyl-1-butynyl, -4-pentynyl, -1-hexynyl, -2-hexynyl, and -5-hexynyl.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_3))$—, —$(CHCH(CH_3)_2)$— and —$C(CH_3)(CH_2CH_3)$—.

As used herein, "cycloalkyl" refers to a group selected from $C_3$-$C_{12}$ cycloalkyl, and preferably a $C_{3-8}$ cycloalkyl. Typical cycloalkyl groups include cyclopropyl, cyclobutyl, cyclopentyl, cyclohexyl, cycloheptyl, cyclooctyl, and cyclononyl.

As used herein, the term "heterocyclyl" refers to groups containing one to four heteroatoms each selected from O, S and N, wherein each heterocyclic group has from 4 to 10 atoms in its ring system, and wherein the ring of said group does not contain two adjacent O or S atoms. Typical heterocyclyl groups include pyrrolidinyl, tetrahydrofuranyl, dihydrofuranyl, tetrahydrothienyl, tetrahydropyranyl, dihydropyranyl, tetrahydrothiopyranyl, piperidino, sulfolanyl, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroquinazolinyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. The point of attachment may be on the oxygen or carbon atom.

As used herein, the term "alkylthio" (also termed as alkylsulfanyl) refers to straight-chain or branched alkyl groups (preferably having 1 to 6 carbon atoms, e.g. 1 to 4 carbon atoms ($C_1$-$C_6$-alkylthio), which are bound to the remainder of the molecule via a sulfur atom at any bond in the alkyl group. Examples of $C_1$-$C_4$-alkylthio include methylthio, ethylthio, n-propylthio, isopropylthio, n-butylthio, sec-butylthio, isobutylthio and tert-butylthio. Examples of $C_1$-$C_6$-alkylthio include, apart from those mentioned for $C_1$-$C_4$-alkylthio, 1-, 2- and 3-pentylthio, 1-, 2- and 3-hexylthio and the positional isomers thereof.

As used herein, the term "alkoxyalkyl" refers to the group -alk$_1$-O-alk$_2$ where alk$_1$ is alkyl or alkenyl, and alk$_2$ is alkyl or alkenyl.

As used herein, the term "alkylamino" refers to the group —NRR' where R is alkyl and R' is hydrogen or alkyl.

As used herein, "aryl" refers to a group selected from $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

As used herein, "heteroaryl" refers to a group having from 5 to 14 ring atoms; 6, 10 or 14 pi electrons shared in a cyclic array; and containing carbon atoms and 1, 2 or 3 oxygen, nitrogen and/or sulfur heteroatoms. Examples of heteroaryl groups include indazolyl, furyl, thienyl, pyrrolyl, imidazolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, tetrazolyl, triazinyl, azepinyl, oxazepinyl, morpholinyl, thiazepinyl, diazepinyl, thiazolinyl, benzimidazolyl, benzoxazolyl, imidazopyridinyl, benzoxazinyl, benzothiazinyl, benzothiophenyl oxazolopyridinyl, benzofuranyl, quinolinyl, quinazolinyl, quinoxalinyl, benzothiazolyl, phthalimido, benzofuranyl, benzodiazepinyl, indolyl, indanyl, azaindazolyl, deazapurinyl and isoindolyl.

As used herein, the term "amino" or "amino group" refers to —$NH_2$.

As used herein, the term "optionally substituted" refers to a group that is unsubstituted or substituted with one or more substituents. For example, where the groups $C_1$-$C_6$ alkyl, $C_2$-$C_6$ alkenyl, $C_2$-$C_6$ alkynyl, —O—$C_1$-$C_6$ alkyl, —O—$C_2$-$C_6$ alkenyl, and —O—$C_2$-$C_5$ alkynyl are referred to as being optionally substituted, they may or may not be substituted. Where substituted, they may be substituted with a group selected from the group consisting of halo, halo($C_{1-6}$)alkyl, (halo)$_2$($C_{1-4}$)alkyl, (halo)$_3$($C_{1-6}$)alkyl, aryl, heteroaryl, cycloalkyl, heterocycloalkyl, $C_{1-6}$alkyl, $C_{2-6}$alkenyl, $C_{2-6}$alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxyl($C_{1-6}$)alkyl, amino($C_{1-6}$)alkyl, carboxy($C_{1-6}$)alkyl, alkoxy($C_{1-6}$)alkyl, nitro, amino, ureido, cyano, alkylcarbonylamino, hydroxyl, thiol, alkylcarbonyloxy, azido, alkoxy, carboxy, aminocarbonyl, and $C_{1-6}$alkylthiol. Preferred optional substituents include halo, halo($C_{1-6}$)alkyl, (halo)$_2$($C_{1-6}$)alkyl, (halo)$_3$($C_{1-6}$)alkyl, hydroxyl($C_{1-6}$)alkyl, amino($C_{1-6}$)alkyl, hydroxyl, nitro, $C_{1-6}$alkyl, $C_{1-6}$alkyl and amino. Preferred numbers of optional substituents are 1, 2 or 3.

Compounds of the Invention or a Tautomer or Stereoisomer Thereof, or a Solvate, Prodrug or a Pharmaceutically Acceptable Salt Thereof In one aspect, the invention provides a compound having the following Formula (I):

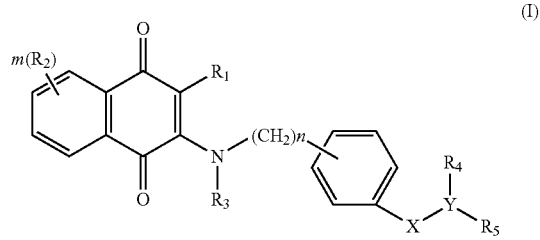

wherein $R_1$ is halogen, $C_{1-10}$alkyl, $C_{2-10}$alkenyl, $C_{2-10}$alkynyl, $NH_2$, $NO_2$, OH or CN;

each $R_2$ is the same or different, representing H, $C_{1-10}$alkyl, $C_{2-10}$alkenyl, $C_{2-10}$alkynyl, $NH_2$, $NO_2$, $C_{1-10}$alkyloxy, $C_{1-10}$alkylthio, $C_{1-10}$alkylamino, $C_{1-10}$alkyloxy$C_{1-10}$alkyl, OH or CN, $C_{6-10}$aryl or $C_{5-7}$heterocyclic having 1 to 3 heteroatoms selected from the group consisting of N, O and S;

$R_3$ is H, $C_{1-10}$alkyl, $C_{2-10}$alkenyl, $C_{2-10}$alkynyl, $NH_2$, $NO_2$, OH or CN;

when Y is —N—, $R_4$ is H, $C_{1-10}$alkyl, $C_{2-10}$alkenyl, $C_{2-10}$alkynyl, $NH_2$, $NO_2$, OH or CN, or when Y is —C—, $R_4$ together with carbon atom attached therefrom and $R_5$ form a $C_{5-7}$heterocyclic ring having 0 to 3 heteroatoms selected from O; N and S or heterofused bicyclic ring having 0 to 3 heteroatoms selected from O; N and S;

$R_5$ is absent, OH, $C_{3-10}$cycloalkyl, $C_{6-10}$aryl, $C_{5-7}$heterocyclic ring having 0 to 3 heteroatoms selected from O; N and S or $C_{10-12}$ fused heterocyclic ring having 0 to 3 heteroatoms selected from O; N and S, each of cycloalkyl, aryl, heterocyclic ring and fused heterocyclic ring is unsubstituted or substituted with one to three of OH; halogen; $NH_2$; $NO_2$; CN, $C_{1-10}$alkyl; $C_{2-10}$alkenyl; $C_{2-10}$alkynyl; $C_{1-10}$alkyloxy; $C_{5-10}$heteroaryl having 1 to 3 heteroatoms selected from the group consisting of N, O and S, unsubstituted or substituted with $C_{1-10}$alkyl, $C_{2-10}$alkenyl, $C_{2-10}$alkynyl, OH, halogen, CN, $NH_2$ or $NO_2$; —S(O)$_2$-phenyl wherein the phenyl is unsubstituted or substituted with halogen, OH, CN, $NH_2$, $NO_2$, $C_{1-10}$alkyl, $C_{2-10}$alkenyl, $C_{2-10}$alkynyl or $C_{1-10}$alkyloxy; —C(O)NHOH; —C(O)NH$_2$; —C(O)-phenyl wherein phenyl is unsubstituted or substituted with 1-5 same or different substituents selected from the group consisting of OH, halogen, CN, $NH_2$, $NO_2$, $C_{1-10}$alkyl, $C_{2-10}$alkenyl, $C_{2-10}$alkynyl or $C_{1-10}$alkyloxy; —C(O)NR$_a$R$_b$; NHS(O)$_2$ phenyl wherein phenyl is optionally substituted with OH, halogen, CN, $NH_2$, $NO_2$, $C_{1-10}$alkyl, $C_{2-10}$alkenyl, $C_{2-10}$alkynyl or $C_{1-10}$alkyloxy; $C_{1-10}$alkylene-heteroaryl; —S(O)$_2$-heteroaryl; —S(O)$_2$-heterocyclic ring; —S(O)$_2$N(H)-heteroaryl; -alkylene-N(H)-heteroaryl; heterocyclic ring unsubstituted or substituted with $C_{1-10}$alkyl; and $R_a$ and $R_b$ are the same or different, independently representing H; OH; alkyl; alkenyl; alkynyl; alkyloxy; cycloalkyl; heterocylyl; alkyleneamino; alkylene-N-(alkyl)$_2$; aryl unsubstituted or substituted with OH, halogen, CN, $NH_2$, $NO_2$, alkyl, alkenyl, alkynyl, alkyloxy or heteroaryl; heteroaryl unsubstituted or substituted with OH, halogen, CN, $NH_2$, $NO_2$, alkyl, alkenyl, alkynyl or alkyloxy; alkylene-heteroaryl; or alkylene-heterocylyl unsubstituted or substituted with alkyl;

X is —C(O), —S(O)$_2$ or —NH—C(O)—;
Y is —C— or —N—;
m is an integer of 0-3; and
n is an integer of 0-7;

or a tautomer, stereoisomer or enantiomer thereof, or a solvate, prodrug or a pharmaceutically acceptable salt thereof.

In some embodiments of formula (I), m is 0; $R_1$ is halogen; n is any integer of 1-4; $R_3$ is H; X is —C(O)—; Y is —N—; $R_4$ is H; and $R_5$ is OH; $C_{3-8}$cycloalkyl; phenyl unsubstituted or substituted with one to three same or different substituents selected from OH, CN, halogen, $NH_2$ or $C_{1-4}$alkylpiperazinyl; $C_{1-6}$alkylpiperazinyl; $C_{1-6}$alkylpyridinyl; $C_{1-6}$alkylpyrrolidinyl; pyridinyl; pyrimidinyl; pyrazinyl; piperazinyl; pyrrolidinyl; thiazolyl; benzimidazolyl; pyrazolyl; indazolyl; pyrazolyl; quinolinyl; indolyl; $C_{1-4}$indolyl; indazolyl; azaindolyl; azaindazolyl; deazapurinyl; indanyl; morpholinoyl or $C_{1-4}$alkylmorpholinoyl, each of which is unsubstituted or substituted with one, two or three groups selected from OH, CN, halogen or $NH_2$.

In some embodiments of formula (I), m is 0; $R_1$ is halogen; n is any integer of 1-2; $R_3$ is H; X is —C(O); Y is —N—; $R_4$ is H; and $R_5$ is OH; $C_3$cycloalkyl; pyridinyl; phenyl substituted by one to three of $NH_2$, halogen, OH, CN or $C_{1-4}$alkylpiperazinyl; pyrinidinyl unsubstituted or substituted $NO_2$, $NH_2$ or $C_{1-4}$alkyl; pyrazinyl unsubstituted or substituted $NO_2$, $NH_2$ or $C_{1-4}$alkyl; thiazolyl unsubstituted or substituted $NO_2$, $NH_2$ or $C_{1-4}$alkyl; benzimidazolyl unsubstituted or substituted $NO_2$, $NH_2$ or $C_{1-4}$alkyl; pyrazolyl unsubstituted or substituted $NO_2$, $NH_2$ or $C_{1-4}$alkyl; indazolyl unsubstituted or substituted $NO_2$, $NH_2$ or $C_{1-4}$alkyl; thiazolyl unsubstituted or substituted $NO_2$, $NH_2$ or $C_{1-4}$alkyl; quinolinyl unsubstituted or substituted $NO_2$, $NH_2$ or $C_{1-4}$alkyl; indolyl unsubstituted or substituted $NO_2$, $NH_2$ or $C_{1-4}$alkyl; indazolyl unsubstituted or substituted $NO_2$, $NH_2$ or $C_{1-4}$alkyl; azaindazolyl unsubstituted or substituted $NO_2$, $NH_2$ or $C_{1-4}$alkyl; deazapurinyl unsubstituted or substituted $NO_2$, $NH_2$ or $C_{1-4}$alkyl; indanyl unsubstituted or substituted $NO_2$, $NH_2$ or $C_{1-4}$alkyl; or morpholinoyl unsubstituted or substituted $NO_2$, $NH_2$ or $C_{1-4}$alkyl.

In some embodiments of formula (I), m is 0; n is 0; X is —C(O); Y is —N—; $R_1$ is halogen or $C_{1-4}$alkyl; $R_3$ is H; $R_4$ is H or $C_{1-4}$alkyl; and $R_5$ is pyridinyl, pyrazinyl, or pyrimidinyl.

In some embodiments of formula (I), m is 0; n is 0; X is —C(O); Y is —N—; $R_1$ is halogen; $R_3$ is H; $R_4$ is H; and $R_5$ is pyridinyl, pyrazinyl, or pyrimidinyl.

In some embodiments of formula (I), m is 0; n is 0; X is —NHC(O)—; Y is —C—; $R_1$ is halogen or $C_{1-4}$alkyl; $R_3$ is H; and $R_4$ together with carbon atom attached therefrom and $R_5$ form a $C_{5-7}$heterocyclic ring having 0 to 3 heteroatoms selected from O. Preferably, the fused $C_{5-7}$heterocyclic ring is pyridinyl.

In some embodiments of formula (I), m is 0; n is 0; X is S(O)$_2$; Y is —N—; $R_1$ is halogen or $C_{1-4}$alkyl; $R_3$ is H; and $R_4$ together with nitrogen atom attached therefrom and $R_5$ form a fused bicyclic ring. Preferably, the fused bicyclic ring is indolyl or azaindolyl.

In some embodiments of formula (I), the compounds include but are not limited to the following:

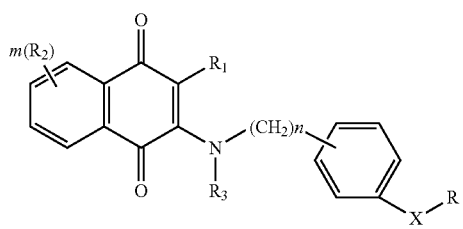

m is 0; $R_3$ is H; X is C(O); and R is

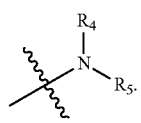

| Example (Compound #) | Code | Number | R₁ | (CH₂)ₙ | R | Structure of R |
|---|---|---|---|---|---|---|
| Example 2 (1) | MPT0L016 | 19-1304 | Cl | CH₂ | NHOH | 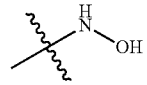 [SMILES: *NO] |
| Example 3 (2) | MPT0L018 | 19-1312 | Cl | CH₂ | 2-aminopyridine | 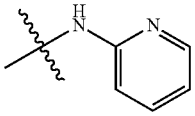 [SMILES: *Nc1ccccn1] |
| Example 4 (3) | MPT0L019 | 19-1313 | Cl | CH₂ | 2-aminobenzamide | 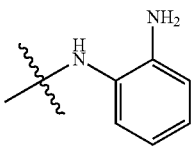 [SMILES: *Nc1ccccc1N] |
| Example 5 (4) | MPT0L055 | 31-324 | Cl | CH₂ | 3-aminopyridine | 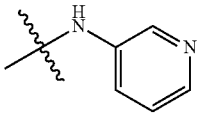 [SMILES: *Nc1cccnc1] |
| Example 6 (5) | MPT0L056 | 31-326 | Cl | CH₂ | 4-aminopyridine | 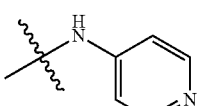 |
| Example 48 (6) | MPT0L080 | 19-1637 | Br | CH₂ | 2-aminopyridine | 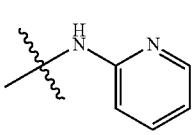 [SMILES: *Nc1ccccn1] |
| Example 51 (7) | MPT0L101 | 31-482 | Cl | CH₂ | 4-aminopyrimidine | 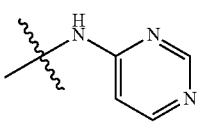 [SMILES: *Nc1ccncn1] |
| Example 52 (8) | MPT0L076 | 31-396 | Cl | CH₂ | 2-aminopyrazine | 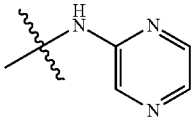 [SMILES: *Nc1cnccn1] |
| Example 7 (9) | MPT0L081 | 19-1652 | Cl | CH₂ | 3-fluoroaniline | 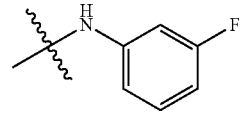 [SMILES: *Nc1cccc(F)c1] |
| Example 8 (10) | MPT0L082 | 19-1653 | Cl | CH₂ | 4-fluoroaniline | 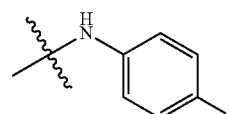 |
| Example 9 (11) | MPT0L083 | 19-1654 | Cl | CH₂ | Aniline | 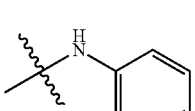 |
| Example 10 (12) | MPT0L084 | 19-1655 | Cl | CH₂ | 2-fluoroaniline | 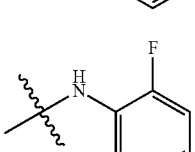 |

-continued

| Example (Compound #) | Code | Number | R₁ | (CH₂)ₙ | R | Structure of R |
|---|---|---|---|---|---|---|
| Example 11 (13) | MPT0L085 | 19-1658B | Cl | CH₂ | 2-aminothiazole | 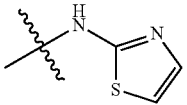 |
| Example 12 (14) | MPT0L086 | 19-1659 | Cl | CH₂ | 2-aminobenzimidazole | 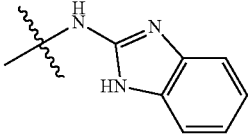 [SMILES: *Nc1nc2ccccc2[nH]1] |
| Example 13 (15) | MPT0L087 | 19-1666 | Cl | CH₂ | 4-aminophenol | 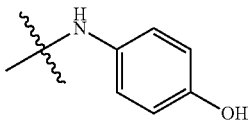 [SMILES: *Nc1ccc(O)cc1] |
| Example 14 (16) | MPT0L088 | 19-1673 | Cl | CH₂ | 3-ethynylaniline | 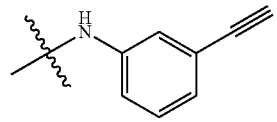 [SMILES: *Nc1cccc(C#C)c1] |
| Example 15 (17) | MPT0L092 | 19-1678A | Cl | CH₂ | 2-fluoro-4-iodoaniline | 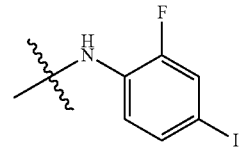 [SMILES: *Nc1ccc(I)cc1F] |
| Example 16 (18) | MPT0L093 | 19-1703 | Cl | CH₂ | 5-aminobenzimidazole | 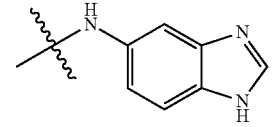 [SMILES: *Nc1ccc2[nH]cnc2c1] |
| Example 17 (19) | MPT0L094 | 19-1704 | Cl | CH₂ | (N1-)3-aminopyrazole | 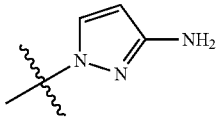 [SMILES: *n1ccc(N)n1] |
| Example 18 (20) | MPT0L095 | 19-1705 | Cl | CH₂ | Cyclopropylamine | 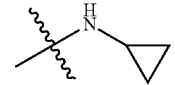 |
| Example 19 (21) | MPT0L096 | 19-1706 | Cl | CH₂ | Cyclopentylamine | 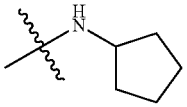 |
| Example 20 (22) | MPT0L097 | 19-1708 | Cl | CH₂ | 5-aminoindazole | 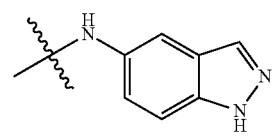 [SMILES: *Nc1ccc2[nH]ncc2c1] |
| Example 21 (23) | MPT0L098 | 19-1709 | Cl | CH₂ | 2-amino-5-methylthiazole | 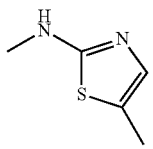 |

-continued

| Example (Compound #) | Code | Number | R₁ | (CH₂)ₙ | R | Structure of R |
|---|---|---|---|---|---|---|
| Example 22 (24) | MPT0L099 | 19-1712A-2 | Cl | CH₂ | 3-amino-5-methylpyrazole | 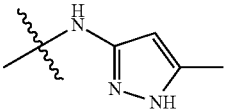 |
| Example 23 (25) | MPT0L100 | 19-1712B | Cl | CH₂ | (N1-)3-amino-5-methylpyrazole | 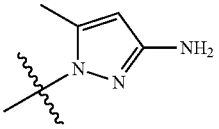 [SMILES: *n1nc(N)cc1C] |
| Example 24 (26) | MPT0L103 | 19-1716B | Cl | CH₂ | 4-amino-3-nitropyridine | 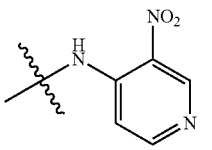 [SMILES: *Nc1ccncc1[N+](=O)[O-]] |
| Example 26 (28) | MPT0L108 | 19-1830-2 | Cl | CH₂ | 6-aminoquinoline | 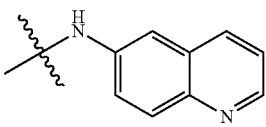 [SMILES: *Nc1ccc2ncccc2c1] |
| Example 27 (29) | MPT0L109 | 19-1831 | Cl | CH₂ | 8-aminoquinoline | 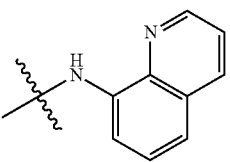 [SMILES: *Nc1cccc2cccnc12] |
| Example 28 (30) | MPT0L110 | 19-1834 | Cl | CH₂ | 3-aminoquinoline |  |
| Example 29 (31) | MPT0L111 | 19-1835 | Cl | CH₂ | 5-aminoquinoline | 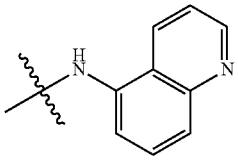 [SMILES: *Nc1cccc2ncccc12] |
| Example 30 (32) | MPT0L112 | 19-1854-2 | Cl | CH₂ | 4-amino-2-methylquinoline | 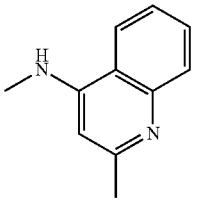 |
| Example 31 (33) | MPT0L113 | 19-1858-2 | Cl | CH₂ | 5-aminoindole | 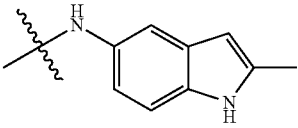 [SMILES: *Nc1ccc2[nH]c(C)cc2c1] |
| Example 32 (34) | MPT0L114 | 19-1859B | Cl | CH₂ | 5-amino-2-methylindole | 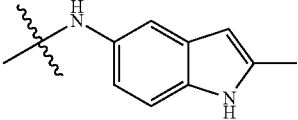 [SMILES: *Nc1ccc2[nH]c(C)cc2c1] |

-continued

| Example (Compound #) | Code | Number | R₁ | (CH₂)ₙ | R | Structure of R |
|---|---|---|---|---|---|---|
| Example 33 (35) | MPT0L115 | 19-1867 | Cl | CH₂ | 7-aminoindole | 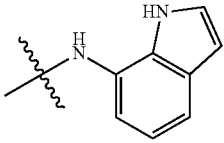 [SMILES: *Nc1cccc2cc[nH]c12] |
| Example 34 (36) | MPT0L116 | 19-1875 | Cl | CH₂ | 4-aminoindole | 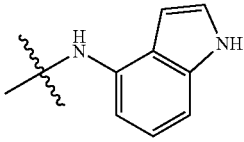 [SMILES: *Nc1cccc2[nH]ccc12] |
| Example 35 (37) | MPT0L117 | 19-1879 | Cl | CH₂ | 4-(N-ethylpiperazine)aniline | 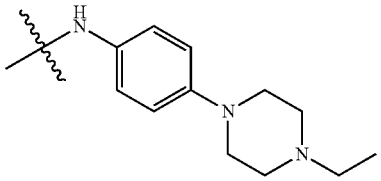 [SMILES: *Nc1ccc(N2CCN(CC)CC2)cc1] |
| Example 36 (38) | MPT0L118 | 19-1887 | Cl | CH₂ | 6-aminoindazole | 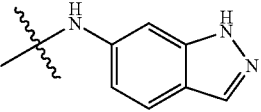 [SMILES: *Nc1ccc2cn[nH]c2c1] |
| Example 37 (39) | MPT0L119 | 19-1890 | Cl | CH₂ | 5-amino-7-azaindole | 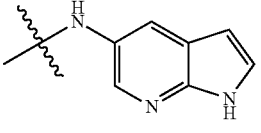 [SMILES: *Nc1cnc2[nH]ccc2c1] |
| Example 38 (40) | MPT0L120 | 19-1891 | Cl | CH₂ | 5-amino-7-azaindazole | 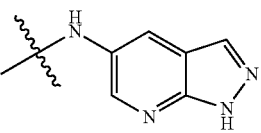 [SMILES: *Nc1cnc2[nH]ncc2c1] |
| Example 39 (41) | MPT0L121 | 19-1898A | Cl | CH₂ | 6-amino-N1-methyl-7-deazapurine | 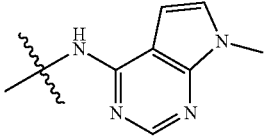 [SMILES: *Nc1ncnc2c1ccn2C] |
| Example 40 (42) | MPT0L124 | 19-1903 | Cl | CH₂ | 4-aminoindan | 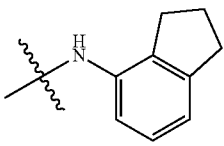 [SMILES: *Nc1cccc2c1CCC2] |

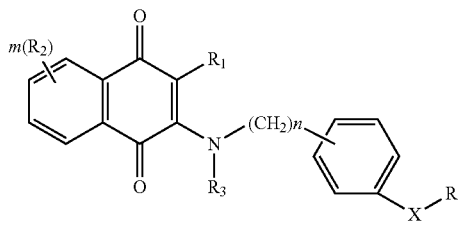

m is 0; $R_3$ is H; n is 0; X is C(O); and R is

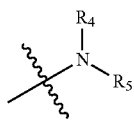

wherein $R_5$ is

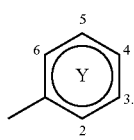

| Example (Compound #) | Code | Number | $R_5$ | $R_4$ | $R_1$ |
|---|---|---|---|---|---|
| Example 57 (51) | MPT0L012 | 19-1284-2 | 2-N | H | Br |
| Example 58 (52) | MPT0L013 | 19-1311B | 2-N | $CH_3$ | Cl |
| Example 59 (53) | MPT0L015 | 19-1286-2 | 2-N | $C_2H_5$ | Cl |
| Example 63 (54) | MPT0L037 | 19-1351A | 2,5-N | H | Cl |
| Example 64 (55) | MPT0L079 | 19-1314A | 2,6-N | H | Cl |
| Example 60 (56) | MPT0L053 | 19-1495A-3 | 2-N | H | i-Pr |

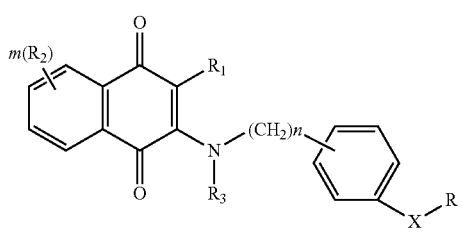

m is O; $R_3$ is H; n is O; X is C(O); and R is

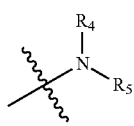

wherein $R_4$ is H and $R_5$ is

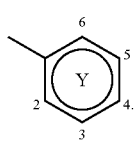

| Example (Compound #) | Code | Number | Y | $R_1$ |
|---|---|---|---|---|
| Example 68 (57) | MPT0L014 | 19-1291A | 2-N | Cl |
| Example 69 (58) | MPT0L036 | 19-1336 | 2,6-N | Cl |
| Example 70 (59) | MPT0L038 | 19-1356 | 2,5-N | Cl |

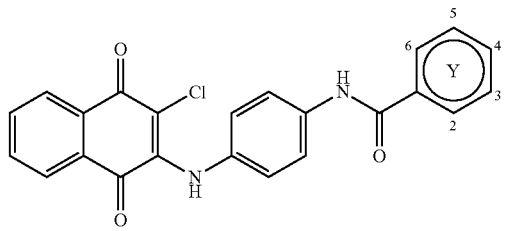

| Example (Compound #) | Code | Number | Y |
|---|---|---|---|
| Example 74 (61) | MPT0L007 | 19-1197B | 4-N |

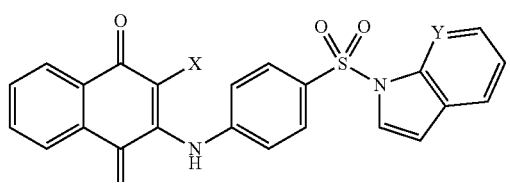

| Example (Compound #) | Code | Number | Y | X |
|---|---|---|---|---|
| Example 78 (63) | MPT0L008 | 24-401-4 | N | Cl |
| Example 77 (62) | MPT0L051 | 19-1473 | C | Cl |
| Example 79 (64) | MPT0L054 | 19-1531-2 | N | i-Pr |

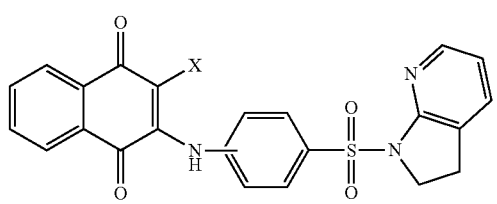

| Example (Compound #) | Code | Number | Position | X |
|---|---|---|---|---|
| Example 82 (65) | MPT0L021 | 21-1042 | Para | Cl |
| Example 83 (66) | MPT0L022 | 21-1041 | Para | Br |
| Example 84 (67) | MPT0L023 | 31-100 | meta | Cl |

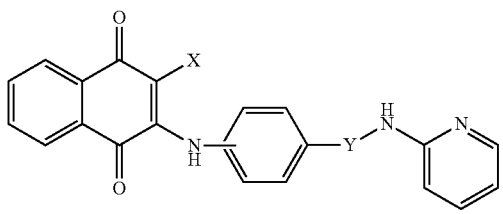

| Example (Compound #) | Code | Number | Y | Position | X |
|---|---|---|---|---|---|
| Example 88 (68) | MPT0L010 | 31-84 | $CH_2$ | meta | Cl |
| Example 89 (69) | MPT0L011 | 31-86 | $CH_2$ | Para | Cl |
| Example 90 (70) | MPT0L024 | 31-98 | $SO_2$ | meta | Cl |

The invention disclosed herein also encompasses prodrugs of the disclosed compounds. Prodrugs are considered to be any covalently bonded carriers that release an active compound of Formula (I) in vivo. Non-limiting examples of prodrugs include esters of compounds of Formula (I), and these may be prepared by reacting such compounds with anhydrides such as succinic anhydride.

The invention disclosed herein also encompasses pharmaceutically acceptable salts of the disclosed compounds. In one embodiment, the present invention includes any and all non-toxic, pharmaceutically acceptable salts of the disclosed compounds, comprising inorganic and organic acid addition salts and basic salts. The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (See Pharmaceutical salts, Birge, S. M. et al., J. Pharm. Sci., (1977), 66, 1-19.)

The invention disclosed herein also encompasses solvates of the disclosed compounds. One type of solvate is a hydrate. Solvates typically do not contribute significantly to the physiological activity or toxicity of the compounds and as such can function as pharmacological equivalents.

The invention disclosed herein also encompasses tautomers and isomers of the disclosed compounds. A given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as, for instance, hydrates including solvates of the free compounds or solvates of a salt of the compound.

Preparation of the Compounds of the Invention

The compounds of the present invention can be prepared using methods known to those skilled in the art in view of this disclosure. For example, the preferred compounds of the invention can be prepared as shown in the following schemes:

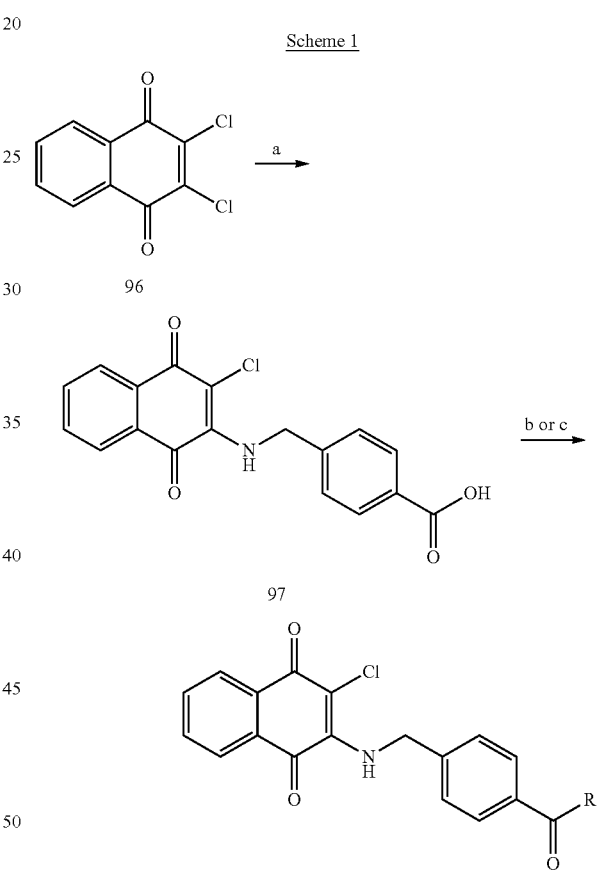

Scheme 1

20 R = cyclopropylamine
21 R = cyclopentylamine
22 R = 5-aminoindazole
23 R = 2-amino-5-methylthiazole
24 R = 3-amino-5-methylpyrazole
25 R = (N1)-3-amino-5-methylpyrazole
26 R = 4-amino-3-nitropyridine
28 R = 6-aminoquinoline
29 R = 8-aminoquinoline
30 R = 3-aminoquinoline
31 R = 5-aminoquinoline
32 R = 4-amino-2-methylquinoline
33 R = 5-aminoindole
34 R = 5-amino-2-methylindole
35 R = 7-aminoindole
36 R = 4-aminoindole
37 R = 4-(N-ethylpiperazine)aniline
38 R = 6-aminoindazole
39 R = 5-amino-7-azaindole
40 R = 5-amino-7-azaindazole
41 R = 6-amino-N1-methyl-7-deazapunne
42 R = 4-aminoindan

*Reagents and condition
(a) 4-aminomethylbenzoic acid, TEA, EtOH, reflux
(b) EDC·HCl, HOBt, NMM, DMF, NH$_2$OTHP, r.t. then 10% TFA(aq.), MeOH, r.t. for 1
(c) substituted amine, HBTU, DIPEA, DMF, r.t. for 2-5, 9-44

Scheme 2

98

6

*Reagents and condition
(a) 4-(aminomethyl)-N-(pyridin-2-yl)benzamide, EtOH, reflux Scheme 3

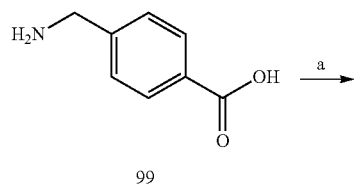

99

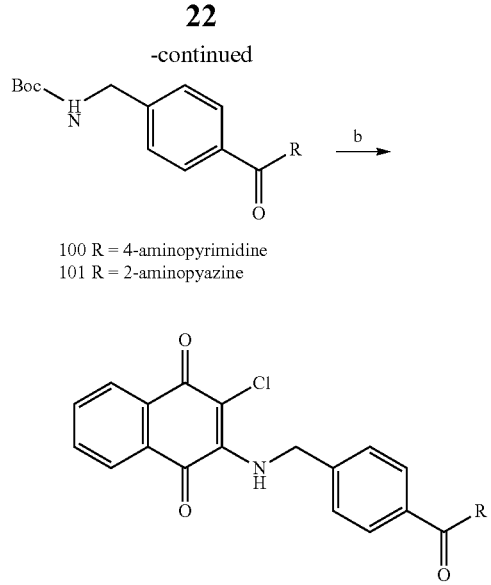

100 R = 4-aminopyrimidine
101 R = 2-aminopyazine

7 R = 4-aminopyrimidine
8 R = 2-aminopyazine

*Reagents and condition
(a) i. Boc$_2$O, NaOH, H$_2$O, THF, rt,
ii. pyridine, DMF, oxalyl chloride, rt then substituted amine, pyridine, rt
(b) TFA, r.t. then 96, reflux.

Scheme 4

102

104 R = CH$_3$
105 R = C$_2$H$_5$

51 R = H, X = Br
52 R = CH$_3$, X = Cl
53 R = C$_2$H$_5$, X = Cl
56 R = H, X = i-Pr

*Reagents and condition
(a) i. 4-nitrobenzoyl chloride, pyr, CH$_2$Cl$_2$, r.t. then alkyl iodide, NaH, DMF, r.t
ii. 10% Pd/C, MeOH, H$_2$, r.t. for 104-105
(b) substituted 1,4-naphthaquinone, EtOH, reflux for 51-53
(c) Pd(PPh$_3$)$_4$, EtOH, toluene, K$_2$CO$_3$(aq.), isopropylboronic acid for 56

Scheme 5

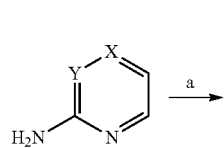

106 X = N, Y = C
107 X = C, Y = N

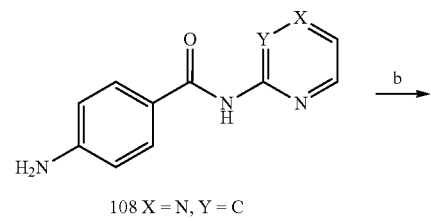

108 X = N, Y = C
109 X = C, Y = N

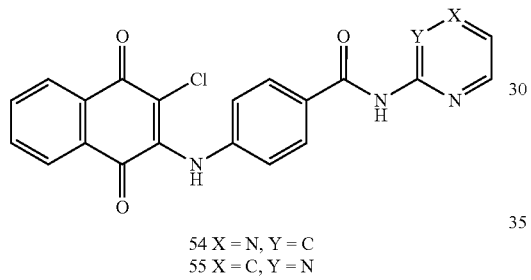

54 X = N, Y = C
55 X = C, Y = N

*Reagents and condition
(a) 4-nitrobenzoyl chloride, pyr, CH$_2$Cl$_2$, r.t. then 10% Pd/C, MeOH, H$_2$, r.t.
(b) 96, EtOH, reflux Scheme 6

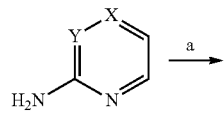

102 X = C, Y = C
107 X = C, Y = N
106 X = N, Y = C

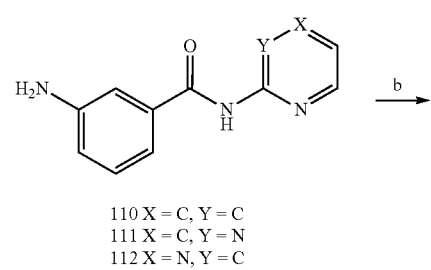

110 X = C, Y = C
111 X = C, Y = N
112 X = N, Y = C

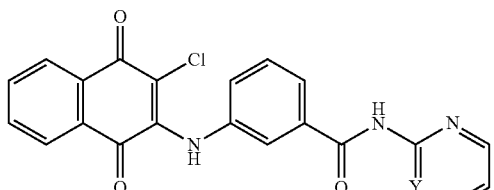

57 X = C, Y = C
58 X = C, Y = N
59 X = N, Y = C

*Reagents and condition
(a) 4-nitrobenzoyl chloride, pyr, CH$_2$Cl$_2$, r.t. then 10% Pd/C, MeOH, H$_2$, r.t.
(b) 96, EtOH, reflux Scheme 7

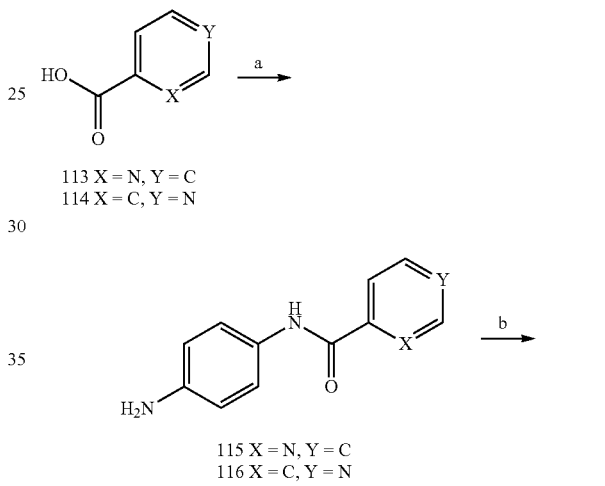

113 X = N, Y = C
114 X = C, Y = N

115 X = N, Y = C
116 X = C, Y = N

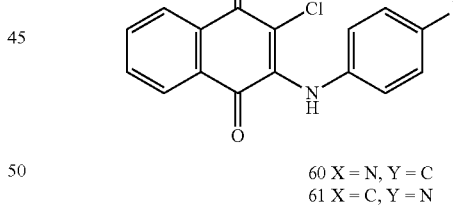

60 X = N, Y = C
61 X = C, Y = N

*Reagents and condition
(a) SOCl$_2$, CH$_2$Cl$_2$, 4-nitroaniline, r.t. then 10% Pd/C, MeOH, H$_2$, r.t.
(b) 96, EtOH, reflux Scheme 8

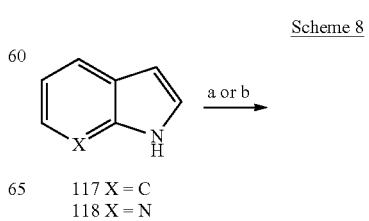

117 X = C
118 X = N

Scheme 10

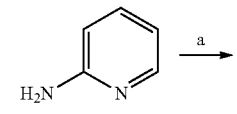

102

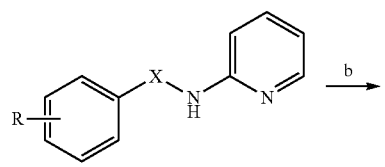

124 R = 3-NO₂, X = CH
125 R = 4-NO₂, X = CH
126 X = 3-NO₂, X = SO₂

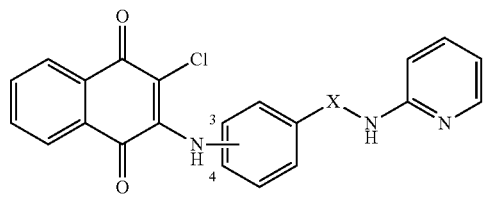

68 bond = position 3, X = CH
69 bond = position 4, X = CH
70 bond = position 3, X = SO₂

*Reagents and condition
(a) substituted benzyl chloride or sulfonyl chloride, toluene, reflux
(b) Fe powder, NH₄Cl, IPA/H₂O, reflux then 96, EtOH, reflux -continued

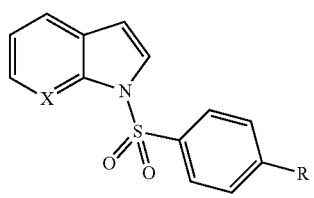

119 X = C, R = NO₂
120 X = N, R = NH₂

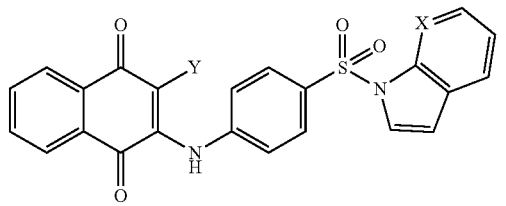

62 X = C, Y = Cl
63 X = N, Y = Cl
64 X = N, Y = i-Pr

*Reagents and condition
(a) NaH, 4-nitrobenzenesulfonyl chloride, DMF, r.t. for 119
(b) NaH, 4-nitrobenzenesulfonyl chloride, DMF, r.t. then Fe powder, NH₄Cl, IPA, H₂O, reflux for 120
(c) Fe powder, NH₄Cl, IPA, H₂O, reflux then 96, EtOH, reflux for 62
(d) 96, EtOH, reflux for 63
(e) 98, EtOh, reflux then Pd(PPh₃)₄, toluene, EtOH, K₂CO₃(aq.), isopropylboronic acid for 64

Scheme 9

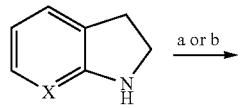

121

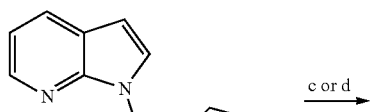

122 R = 4-NO₂
123 R = 3-NO₂

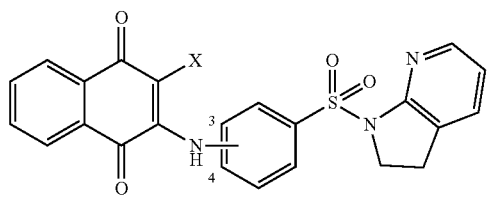

65 bond = position 4, X = Cl
66 bond = position 4, X = Br
67 bond = position 3, X = Cl

*Reagents and condition
(a) NaH, 4-nitrobenzenesulfonyl chloride, DMF, r.t. for 122
(b) 3-nitrobenzenesulfinyl chloride, pyridine, 50° C. for 123
(c) 10% Pd/C, H₂, MeOH, r.t. then substituted 1,4-naphthquinone, EtOH, reflux for 65-66
(d) Fe powder, NH₄Cl, IPA/H₂O, reflux then 96, EtOH, reflux for 67

Pharmaceutical Compositions and Treatments of the Methods of the Invention

The compounds and compositions of the invention can inhibit PCTK1, ROCK2, CSNK1D, JNK 1, JNK3, RIOK2 and DYRK1B, suggesting that the compounds of the invention are potential targets in treatment and/or prevention of neoplastic diseases, neurodegenerative diseases, autoimmune and inflammatory diseases and/or metabolic disorders.

PCTK1 belongs to the cdc2/cdkx subfamily of the serine/threonine family of protein kinases. Cdc2 p34 is essential for the G2 to M transition in vertebrate cells. A potential role for the gene product is the control of neurite outgrowth (Graeser R, Gannon J, Poon R Y, Dubois T, Aitken A, Hunt T. (2002) *Regulation of the CDK-related protein kinase PCTAIRE-1 and its possible role in neurite outgrowth in Neuro-2A cells. J. Cell. Sci.,* 115: 3479-90).

ROCK2 belongs to the AGC (PKA/PKG/PKC) family of serine/threonine kinases. It is involved mainly in regulating the shape and movement of cells by acting on the cytoskeleton. Recent research has shown that ROCK signaling plays an important role in many diseases including diabetes, neurodegenerative diseases such as Parkinson's disease and amyotrophic lateral sclerosis, pulmonary hypertension and cancer (Tönges L, Frank T et al. (2012) *Inhibition of rho kinase enhances survival of dopaminergic neurons and attenuates axonal loss in a mouse model of Parkinson's disease. Brain,* 135 (11): 3355-70; Lin Yao, Surabhi Chandra, Haroldo A. Toque, Anil Bhatta, Modesto Rojas, Ruth B. Caldwell, R. William Caldwell, (2013) *Prevention of diabetes-induced arginase activation and vascular dysfunction by Rho kinase (ROCK) knockout. Cardiovascular Research,* 97, 509-519; Ferrer, Isidre; Mohan, Pooja; Chen, Helen; Castellsague, Joan; Gómez-Baldó, Laia; Carmona, Marga; Garcia, Nadia; Aguilar, Helena; Jiang, Jihong; Skowron, Margaretha; Nellist, Mark; Ampuero, Israel; Russi, Antonio; Lázaro, Conxi; Maxwell, Christopher A; Pujana, Miguel Angel. (2014). *Tubers from patients with tuberous sclerosis complex are characterized by changes in microtubule biology through ROCK2 signalling. The Journal of Pathology,* 233(3): 247-57; and Kim-Ann Saal, Jan C. Koch, Lars Tatenhorst, Éva M. Szegö, Vinicius Toledo Ribas, Uwe Michel, Mathias Bähr, Lars Tönges, Paul Lingor. (2015) *AAV.shRNA-mediated downregulation of ROCK2 attenuates degeneration of dopaminergic neurons in* toxin-*induced models of Parkinson's disease in vitro* and *in vivo. Neurobiology of Disease,* (73):150-162).

CSNK1D is essential serine/threonine-protein kinase that regulates diverse cellular processes including DNA replication and repair. The encoded protein may also be involved in the regulation of apoptosis, circadian rhythm, microtubule dynamics, chromosome segregation, and p53-mediated effects on growth. Recent research has also identified a link between mutations in the CK1 delta gene and familial migraine and advanced sleep phase. CK1 Delta was also found to phosphorylate Tau and disrupts its binding to microtubules and may contribute to degeneration in AD and other dementias (Lee H, Chen R, Lee Y, Yoo S, Lee C. (2009) *Essential roles of CK1 and CK1 in the mammalian circadian clock. PNAS,* 106 (50): 21359-64; and Biswas A, Mukherjee S, Das S, Shields D, Chow C W, Maitra U. (2011) *Opposing action of casein kinase 1 and calcineurin in nucleo-cytoplasmic shuttling of mammalian translation initiation factor eIF6. Journal of Biological Chemistry,* 286 (4): 3129-38).

c-Jun N-terminal kinases (JNKs) belong to the mitogen-activated protein kinase (MAPK) family, and are responsive to stress stimuli, such as cytokines, ROS, UV irradiation, heat shock, and osmotic shock, and contribute to inflammatory responses. They also play a role in T cell differentiation and the cellular apoptosis pathway. JNK1 has been found to regulate Jun protein turnover by phosphorylation and activation of the ubiquitin ligase Itch. JNK1 is necessary for normal activation and differentiation of CD4 helper T (TH) cells into TH1 and TH2 effector cells. JNK1/JNK2 are found in all cells and tissues while JNK3 is found mainly in the brain, but is also found in the heart and the testes (Lufen Chang, Hideaki Kamata, Giovanni Solinas, Jun-Li Luo, Shin Maeda, K. Venuprasad, Yun-Cai Liu, Michael Karin. (2006) *The E3 Ubiquitin Ligase Itch Couples JNK Activation to TNFα-induced Cell Death by Inducing c-FLIPL Turnover. Cell,* 124(3):601-13; Bode A M, Dong Z. (2007) *The Functional Contrariety of JNK. Mol. Carcinog.* 46 (8): 591-8; Eun Kyung Kim, Eui-Ju Choi. (2010) *Pathological roles of MAPK signaling pathways in human diseases. Biochimica et Biophysica Acta.* 1802: 396-405).

RIOK2 is a serine/threonine-protein kinase and plays an important role in ribosome biogenesis (Liu T, Deng M, Li J, Tong X, Wei Q, Ye X. (2011) *Phosphorylation of right open reading frame 2 (Rio2) protein kinase by polo-like kinase 1 regulates mitotic progression. J Biol Chem,* 286(42):36352-60; and Read R D, Fenton T R, Gomez G G, Wykosky J, Vandenberg S R, Babic I, Iwanami A, Yang H, Cavenee W K, Mischel P S, Furnari F B, Thomas J B. (2013) *A kinome-wide RNAi screen in Drosophila Glia reveals that the RIO kinases mediate cell proliferation and survival through TORC2-Akt signaling in glioblastoma. PLoS Genet,* 9(2):e1003253).

DYRK1B is found mainly in muscle and testes and involved in the regulation of nuclear functions. The encoded protein participates in the regulation of the cell cycle. Expression of this gene may be altered in tumor cells, and mutations in this gene were found to cause abdominal obesity-metabolic syndrome 3 (Ali R. Keramati, M.D., Mohsen Fathzadeh, Ph.D., Gwang-Woong Go, Ph.D., Rajvir Singh, Ph.D., Murim Choi, Ph.D., Saeed Faramarzi, M.D., Shrikant Mane, Ph.D., Mohammad Kasaei, M.D., Kazem Sarajzadeh-Fard, M.D., John Hwa, M.D., Ph.D., Kenneth K. Kidd, Ph.D., Mohammad A. Babaee Bigi, M.D., Reza Malekzadeh, M.D., Adallat Hosseinian, M.D., Masoud Babaei, M.D., Richard P. Lifton, M.D., Ph.D., and Arya Mani, M.D. (2014) *A Form of the Metabolic Syndrome Associated with Mutations in DYRK1B. N Engl J Med,* 370:1909-1919).

Accordingly, the compounds of the invention are potential targets in treatment and/or prevention of neoplastic diseases, neurodegenerative diseases, inflammatory diseases and/or metabolic disorders. In some embodiments, the neoplastic disease includes but is not limited to benign tumor and cancer. In some embodiments, neurodegenerative disease includes but is not limited to ALS, Parkinson's disease, Alzheimer's disease, and Huntington's disease. In some embodiments, autoimmune and inflammatory disease includes but is not limited to insulin-dependent diabetes mellitus (IDDM), diabetes mellitus, multiple sclerosis, experimental autoimmune encephalomyelitis, acute disseminated encephalomyelitis, arthritis, rheumatoid arthritis, experimental autoimmune arthritis, myasthenia gravis, thyroiditis, Hashimoto's disease, primary myxedema, thyrotoxicosis, pernicious anemia, autoimmune atrophic gastritis, Addison's disease, premature menopause, male infertility, juvenile diabetes, goodpasture's syndrome, pemphigus vulgaris, pemphigoid, sympathetic ophthalmia, phacogenic uveitis, autoimmune haemolyticanaemia, idiopathic leucophenia, primary biliary cirrhosis, active chronic hepatitis Hb.sub.s-ve, cryptogenic cirrhosis, ulcerative colitis, Sjogren's syndrome, scleroderma, Wegener's granulomatosis, poly/dermatomyositis, discoid LE, systemic lupus erythematosus, chron's disease, psoriasis, ankylosingspondylitisis, antiphospholipid antibody syndrome, aplastic anemia, autoimmune hepatitis, coeliac disease, graves' disease, guillain-barre syndrome (GBS), Idiopathic thrombocytopenic purpura, opsoclonus myoclonus syndrome (OMS), optic neuritis, ORd's thyroiditis, pemphigus, polyarthritis, primary biliary cirrhosis, Reiter's syndrome, Takayasu's, temporal arteritis, warm autoimmune hemolytic anemia, wegener's granulomatosis, alopecia universalis, behcet's disease, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, inflammatory skin diseases, allergic contact dermatitis, *H. pylory* gastritis, chronic nasal inflammatory disease, arteriosclerosis and graft versus host disease. In some embodiments, metabolic disorder includes but is not limited to diabetes, high blood pressure, cholesterol, elevated triglyceride level, impaired fasting glucose and insulin resistance.

The compound of the invention is present in the composition in an amount which is effective to treat a particular disorder, including cancers, Parkinson's disease, Alzheimer's disease, and Huntington's disease, restenosis, inflammation, rheumatoid arthritis, inflammatory disorder, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection and proliferation.

The compound of the present invention may be administered to a mammal in the form of a raw chemical without any other components present. The compound is preferably administered as part of a pharmaceutical composition containing the compound combined with a suitable pharmaceutically acceptable carrier. Such a carrier can be selected from pharmaceutically acceptable excipients, diluents and auxiliaries.

Pharmaceutical compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to a mammal, e.g. a human, orally at a dose of from about 5 to about 100 mg per kg body weight of the mammal, or an equivalent amount of a pharmaceutically acceptable salt, prodrug or solvate thereof, per day to treat, prevent or ameliorate the particular disorder. A useful oral dose of a compound of the present invention administered to a mammal is from about 5 to about 100 mg per kg body weight of the mammal, or an equivalent amount of the pharmaceutically acceptable salt, prodrug or solvate thereof. For intramuscular injection, the dose is typically about one-half of the oral dose.

A unit oral dose may comprise from about 5 to about 100 mg, and preferably about 5 to about 100 mg of a compound. The unit dose can be administered one or more times daily, e.g. as one or more tablets or capsules, each containing from about 0.01 mg to about 50 mg of the compound, or an equivalent amount of a pharmaceutically acceptable salt, prodrug or solvate thereof.

The compounds of the present invention may be useful in combination with one or more second therapeutic agents, particularly therapeutic agents suitable for the treatment and/or prevention of the conditions and diseases presented previously.

For example in cancer treatment, the second therapeutic agent can be a mitotic inhibitor (such as a taxane (preferably paclitaxel or docetaxel), vinca alkaloid (preferably, vinblastine, vincristine, vindesine or vinorelbine) or vepesid; an anthracycline antibiotic (such as doxorubicin, daunorubicin, daunorubicin, epirubicin, idarubicin, valrubicin or mitoxantrone); a nucleoside analog (such as gemcitabine); an EGFR inhibitor (such as gefitinib or erlotinib); a folate antimetabolite (such as trimethoprim, pyrimethamine or pemetrexed); cisplatin or carboplatin. Examples of the second therapeutic agent include but are not limited to tamoxifen, taxol, vinblastine, etoposide (VP-16), adriamycin, 5-fluorouracil (5FU), camptothecin, actinomycin-D, mitomycin C, combretastatin(s), more particularly docetaxel (taxotere), cisplatin (CDDP), cyclophosphamide, doxorubicin, methotrexate, paclitaxel and vincristine, and derivatives and prodrugs thereof.

Further useful second therapeutic agents include compounds that interfere with DNA replication, mitosis, chromosomal segregation and/or tubulin activity. Such compounds include adriamycin, also known as doxorubicin, etoposide, verapamil, podophyllotoxin(s), combretastatin(s) and the like. Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting neoplastic cells.

The term "angiogenesis" refers to the generation of new blood vessels, generally in a tissue or organ. Under normal physiological conditions, humans or animals undergo angiogenesis only in specific restricted situations. Uncontrolled (persistent and/or unregulated) angiogenesis is related to various disease states, and occurs during tumor development and metastasis. Accordingly, the anti-angiogenesis agent also can be used as the second anti-cancer agent. Other second anti-cancer agents include but are not limited to alkylators such as cyclophosphamide, edelfosine, estramustine and melphalan; antimetabolites such as fluorouracil, methotrexate, mercaptopurine, UFT, tegafur, uracil and cytarabine; anti-tumor Bleomycin, daunorubicin, doxorubicin and epirubicin; antibiotics such as mitomycin and mitoxantrone; topoisomerase such as camptothecin, irinotecan, etoposide, topotecan; taxanes docetaxel, paclitxael, vinca alkaloids, vinblastine, vincristine, cisplatin and octreotide.

Histone deacetylase inhibitors (HDAC inhibitors) also can be used as the second therapeutic agent. Examples include but are not limited to hydroxamic acids (or hydroxamates), such as trichostatin A, cyclic tetrapeptides (such as trapoxin B), and depsipeptides, benzamides, electrophilic ketones, and aliphatic acid compounds such as phenylbutyrate and valproic acid.

For example in inflammation treatment, the second therapeutic agent includes, but is not limited to, corticosteroid, a lubricant, a keratolytic agent, a vitamin $D_3$ derivative, PUVA and anthralin, $\beta_2$-agonist and a corticosteroid.

For example in autoimmune disease treatment, the second therapeutic agent includes, but is not limited to, immunosuppressants, NSAIDs, COX-2 inhibitors, biologics, non-steroidal calcineurin inhibitors, steroidal anti-inflammatory agents, 5-amino salicylic acid, DMARDs, hydroxychloroquine sulfate, inflammatory modulators, agents that interfere with B cell action, and penicillamine.

Pharmaceutically acceptable carriers and diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of the invention, diluents, dispersing and surface active agents, binders, and lubricants. One skilled in this art may further formulate the compound of the invention in an appropriate manner, and in accordance with accepted practices, such as those disclosed in Remington's Pharmaceutical Sciences, Gennaro, Ed., Mack Publishing Co., Easton, Pa. 1990.

In one aspect, the present invention provides a method for treating a disease in association with block of ubiquitination-proteasome system in a subject, comprising administering to the subject an effective amount of the compound of the invention. The disease includes but is not limited to cancer and related conditions as discussed above. Accordingly, first, the invention provides a method for treating a cancer in a subject, comprising administering to the subject an effective amount of the compound of the invention. Such method includes administering a compound of the present invention to a subject in an amount sufficient to treat the condition. For example, the cancers include but are not limited to the group consisting of: neuroblastoma; lung cancer; bile duct cancer; non small cell lung carcinoma; hepatocellular carcinoma; head and neck squamous cell carcinoma; squamous cell cervical carcinoma; lymphoma; nasopharyngeal carcinoma; gastric cancer; colon cancer; uterine cervical carcinoma; gall bladder cancer; prostate cancer; breast cancer; testicular germ cell tumors; colorectal cancer; glioma; thyroid cancer; basal cell carcinoma; gastrointestinal stromal cancer; hepatoblastoma; endometrial cancer; ovarian cancer; pancreatic cancer; renal cell cancer, Kaposi's sarcoma, chronic leukemia, sarcoma, rectal cancer, throat cancer, melanoma, colon cancer, bladder cancer, mastocytoma, mammary carcinoma, mammary adenocarcinoma, pharyngeal squamous cell carcinoma, testicular cancer, gastrointestinal cancer, or stomach cancer and urothelial cancer.

In a further aspect, the present invention provides a method for treating inflammatory disorders and autoimmune disorders and related conditions as discussed above. Such methods include administering a compound of the present invention to a subject in an amount sufficient to treat the condition. Preferably, the disorders are restenosis, inflammation, rheumatoid arthritis, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection or proliferation.

The dose range of the compounds of general formula (I) applicable per day is usually from 5 to 100 mg, preferably from 5 to 100 mg per kg body weight of the patient. Each dosage unit may conveniently contain from 5 to 100 mg of a compound according to the invention.

The actual therapeutically effective amount or therapeutic dosage will of course depend on factors known by those skilled in the art such as age and weight of the patient, route of administration and severity of disease. In any case, the combination will be administered at dosages and in a manner which allow a therapeutically effective amount to be delivered based upon subject's unique condition.

For oral administration, suitable pharmaceutical compositions of the invention include powders, granules, pills, tablets, lozenges, chews, gels, and capsules as well as liquids, syrups, suspensions, elixirs, and emulsions. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the compound of the invention, buffers, antioxidants, bacteriostats, salts, carbohydrates, and other additives commonly employed in such solutions. Parenteral administrations may be immediate release or modified release (such as an injected or implanted depot).

Compounds of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds of the present invention may also be administered via inhalation or intranasal administration, such as with a dry powder, an aerosol spray or as drops. Additional routes of administration for compounds of the present invention include intravaginal and rectal (by means of a suppository, pessary or enema), and ocular and aural.

Biological Assay
Blocking of ITCH Self-Ubiquitination

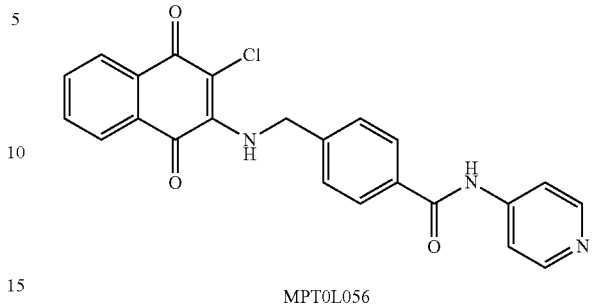

MPT0L056

MPT0L056 of the invention was used to test the blocking of ITCH self-ubiquitination. The results show that MPT0L056 of the invention blocks ITCH self-ubiquitination (Lys-dependent) efficiently (see FIG. 1: In vitro assay and FIG. 2: In vivo assay). [Reference for in vitro assay: Scialpi F, Malatesta M, Peschiaroli A, Rossi M, Melino G, and Bernassola F. Itch self-polyubiquitylation occurs through lysine-63 linkages. Biochem Pharmacol. 2008 Dec. 1; 76(11):1515-21. Reference for in vivo assay: Chang L, Kamata H, Solinas G, Luo J L, Maeda S, Venuprasad K, Liu Y C, and Karin M. The E3 ubiquitin ligase itch couples JNK activation to TNFalpha-induced cell death by inducing c-FLIP(L) turnover. Cell. 2006 Feb. 10; 124(3):601-13.]

Protein Kinase Assay (Kinome Assay).

The compounds of the invention were subjected to protein kinase assay. The results show that the Kd value of MPT0L056 to PCTK1, ROCK2, CSNK1D, JNK1, JNK3, RIOK2 and DYRK1B are >10 µM, 580 nM, 2 µM, 4.2 µM, 430 nM, 6.6 µM and 1.4 µM, respectively, suggesting that the compounds of the invention are potential targets in treatment and/or prevention of neoplastic diseases, neurodegenerative diseases, autoimmune and inflammatory diseases and/or metabolic disorders.

MPT0L056 of the invention was subjected to growth inhibition assay.

Cells were seeded in 96-well plastic plates and exposed to MPT0L056 for 48 hours. Cell viability was assessed using the 3-(4,5-dimethylthiazol-2-yl)-2,5-diphenyltetrazolium bromide assay. Growth inhibition was expressed as the percentage of surviving cells in drug-treated versus DMSO-treated control cells.

| Cell Types | $GI_{50}$ (M) |
|---|---|
| Normal cells | |
| Hepatocytes | $3.0 \times 10^{-5}$ |
| HUVECs | $1.6 \times 10^{-5}$ |
| NHDF | $6.3 \times 10^{-6}$ |
| Pancreas cancer | |
| AsPC1 | $4.6 \times 10^{-6}$ |
| BxPC3 | $1.2 \times 10^{-6}$ |
| Colorectal cancer | |
| HT-29 | $3.8 \times 10^{-6}$ |
| HCT-116 | $4.3 \times 10^{-6}$ |
| Breast cancer | |
| MCF-7 | $9.0 \times 10^{-7}$ |
| MDA-MB-231 | $2.9 \times 10^{-6}$ |
| ZR-75 | $>5 \times 10^{-6}$ |

-continued

| Cell Types | $GI_{50}$ (M) |
|---|---|
| Head and neck cancer | |
| KB | $4.0 \times 10^{-6}$ |
| Skin cancer | |
| A431 | $1.2 \times 10^{-6}$ |
| Stomach cancer | |
| KATO III | $2.4 \times 10^{-6}$ |
| Liver cancer | |
| Hep 3B | $1.4 \times 10^{-6}$ |
| HepG2 | $3.6 \times 10^{-6}$ |
| Kidney cancer | |
| A-498 | $3.5 \times 10^{-6}$ |
| ACHN | $2.7 \times 10^{-6}$ |
| Melanoma | |
| SK-MEL-5 | $2.1 \times 10^{-7}$ |
| B cell leukemia | |
| REH | $2.8 \times 10^{-6}$ |
| Ramos | $8.9 \times 10^{-7}$ |
| T cell lymphoma | |
| H33HJ-JA1 | $1.8 \times 10^{-6}$ |
| Lung cancer | |
| A549 | $>5 \times 10^{-6}$ |
| NCI-H460 | $2.9 \times 10^{-6}$ |
| PC-6 | $1.8 \times 10^{-6}$ |
| Ovarian cancer | |
| OVCAR4 | $1.4 \times 10^{-6}$ |
| OVCAR3 | $1.9 \times 10^{-6}$ |
| Prostate cancer | |
| PC-3 | $2.5 \times 10^{-6}$ |
| Brain cancer | |
| U-87 MG | $2.5 \times 10^{-6}$ |
| T98 | $5.7 \times 10^{-6}$ |
| Leukemia | |
| MOLT4 | $4.0 \times 10^{-6}$ |
| HL-60 | $1.6 \times 10^{-6}$ |
| K562 | $1.7 \times 10^{-6}$ |

The compounds of the invention were subjected to growth inhibition assay.

| Compounds | HL-60 $IC_{50}$ (μM) Mean ± S.E. | HCT-116 | MDA-MB-231 $GI_{50}$ (μM) Mean ± S.E. | Hep3B |
|---|---|---|---|---|
| MPT0L018 | 10~30 | 10~30 | 10~30 | 10~30 |
| MPT0L055 | 10~30 | 10~30 | 10~30 | 10~30 |
| MPT0L076 | 7.27 ± 2.98 | 5.52 ± 0.66 | 9.19 ± 0.4 | 8.77 ± 0.9 |
| MPT0L082 | 10~30 | 10~30 | 10~30 | 10~30 |
| MPT0L083 | 10~30 | 10~30 | 10~30 | 10~30 |
| MPT0L085 | 8.53 ± 0.55 | 10~30 | 10~30 | 10~30 |
| MPT0L086 | 10~30 | 10~30 | 8.88 ± 1.04 | 10~30 |
| MPT0L093 | 10~30 | 10~30 | 10~30 | 10~30 |
| MPT0L094 | 10~30 | 10~30 | 10~30 | 10~30 |
| MPT0L097 | 10~30 | 10~30 | 10~30 | 10~30 |
| MPT0L098 | 7.06 ± 0.73 | 10~30 | 10~30 | 10~30 |
| MPT0L099 | 10~30 | 10~30 | 10~30 | 10~30 |
| MPT0L100 | 10~30 | 10~30 | 10~30 | 10~30 |
| MPT0L103 | 5.42 ± 0.70 | 6.12 ± 1.17 | 10~30 | 10~30 |
| MPT0L108 | 8.09 ± 0.57 | 6.82 ± 0.35 | 10~30 | 10~30 |
| MPT0L109 | 6.43 ± 2.44 | 10~30 | 10~30 | 10~30 |
| MPT0L110 | 7.93 ± 1.14 | 10~30 | 10~30 | 10~30 |
| MPT0L111 | 2.23 ± 0.27 | 10~30 | 10~30 | 10~30 |
| MPT0L112 | 2.68 ± 0.03 | 10~30 | 8.12 ± 1.32 | 10~30 |
| MPT0L113 | 8.92 ± 0.39 | 10~30 | 10~30 | 10~30 |
| MPT0L114 | 10~30 | 10~30 | 10~30 | 10~30 |
| MPT0L116 | 4.06 ± 1.82 | 10~30 | 10~30 | 10~30 |
| MPT0L118 | 7.39 ± 3.49 | 10~30 | 10~30 | 10~30 |
| MPT0L119 | 10~30 | 10~30 | 10~30 | 10~30 |
| MPT0L120 | 7.31 ± 1.94 | 10~30 | 10~30 | 10~30 |
| MPT0L121 | 2.68 ± 0.17 | 10~30 | 10~30 | 10~30 |

Evaluation of MPT0L056 Against Human RPMI8226 Multiple Myeloma in Female Nude Mice MPT0L056 was given orally (1.0% carboxyl methyl cellulose (CMC) and 0.5% Tween 80) to 8-week old female nude mice that had been implanted with PRMI8226 multiple myeloma cell line ($1.0 \times 10^7$ cells in suspension). Mean tumor size on day 1 was ~85 mm³; the study ended when mean tumor volume in the control group approached 400 mm³. Tumor size, in mm³, was calculated as:

$$\text{Tumor Volume} = \frac{w^2 \times l}{2}$$

where w=width and l=length in mm of the tumor. Tumor weight can be estimated with the assumption that 1 mg is equivalent to 1 mm³ of tumor volume. The study design is depicted below (Text Table 1).

TEXT TABLE 1

Study Design

| | | Treatment Regimen | | |
|---|---|---|---|---|
| Group | n | Agent | mg/kg | Schedule |
| 1 | 6 | 1.0% CMC + 0.5% Tween 80 | — | QDx~42 |
| 2 | 6 | SAHA | 100 | QDx~42 |
| 3 | 6 | MPT0L056 | 50 | QDx~42 |
| 4 | 6 | MPT0L056 | 25 | QDx~42 |

Figure 2:
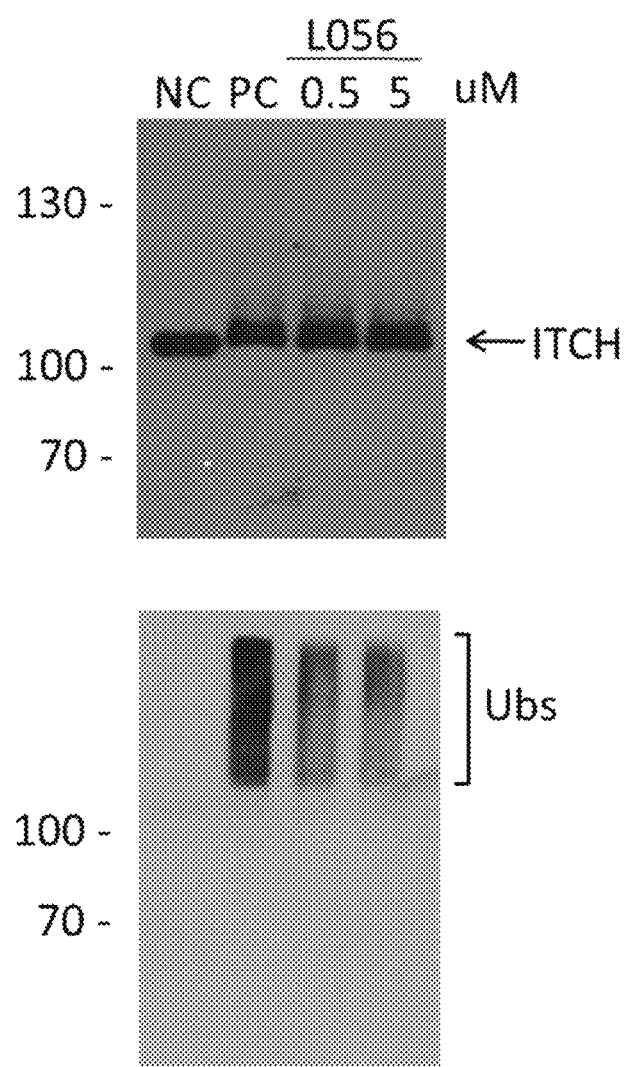
FIG. 2 shows that MPT0L056 blocks ITCH's in vivo self-ubiquitination at a concentration of 0.5 um and 5 um.
Figure 3:
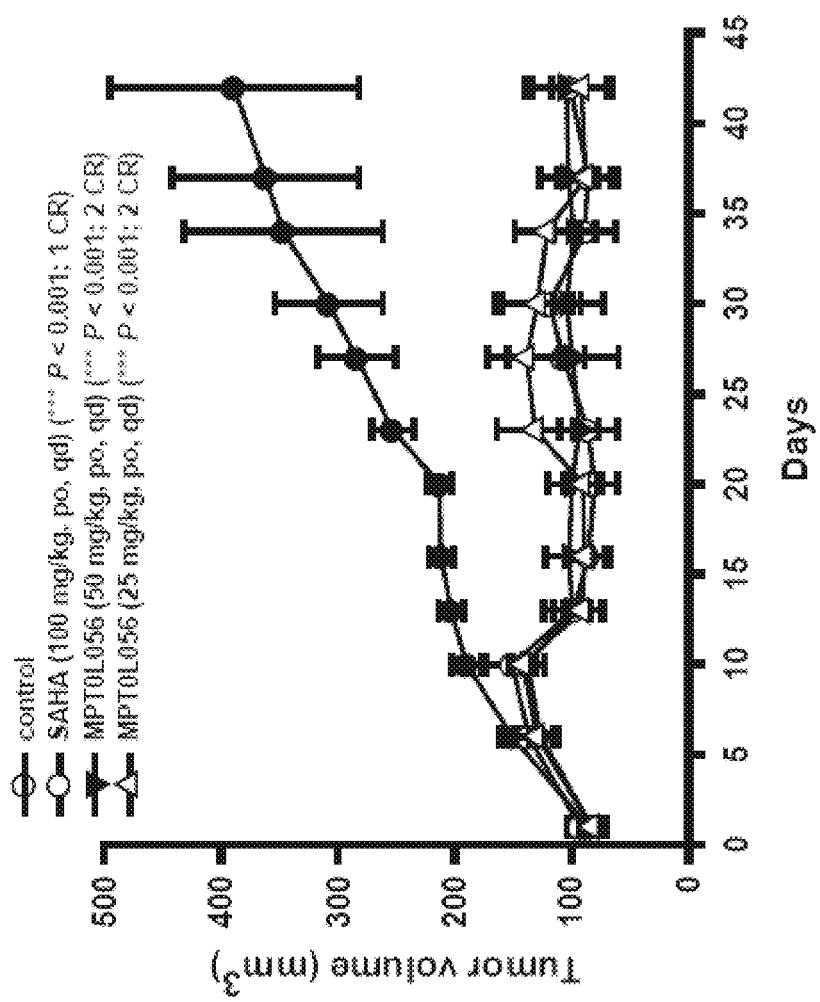
FIG. 3 shows anti-cancer activity of MPT0L056 in human PRMI8226 multiple myeloma xenograft model.
Figure 4:
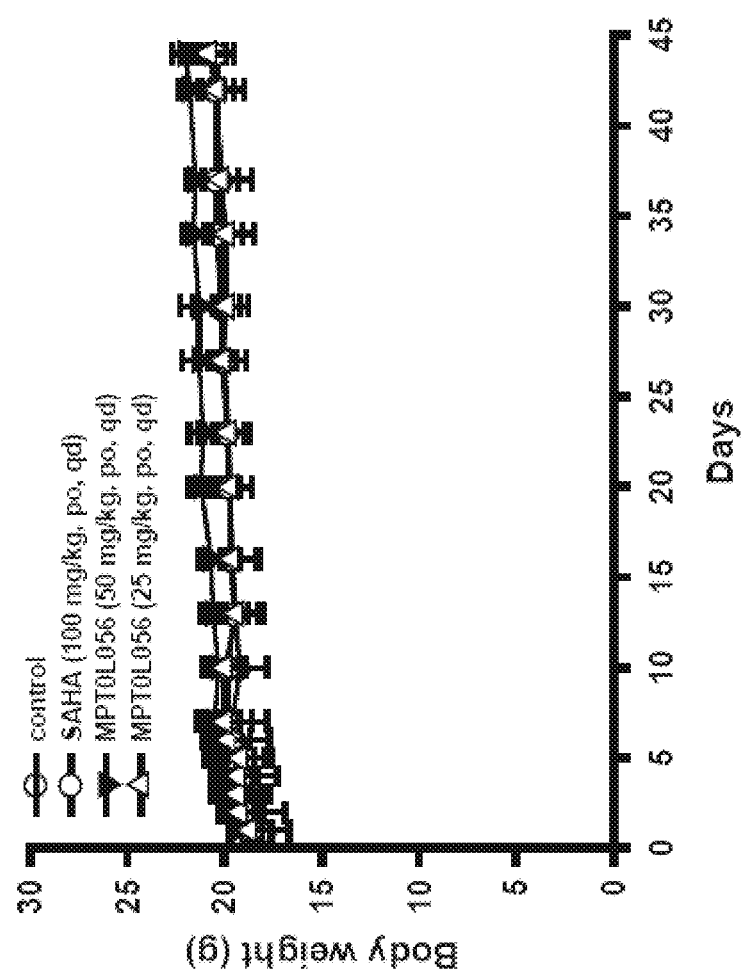
FIG. 4 shows that MPT0L056 did not significantly affect the animal body weight.

The TMU-RPMI8226-e0001 study was performed according to the protocol in Table 1. The 42-day study utilized five groups of mice (n=6) bearing established human PRMI8226 multiple myeloma with mean volumes of ~85 mm³ on D1. The tumor growth curve and animal body weight change for each treatment group are shown in FIG. 1 and FIG. 2, respectively. FIG. 1 shows MPT0L056 p.o. at 50 and 25 mg/kg once every day for 42 days. Based on the Student's t-test analysis, MPT0L056 50 mg/kg (P<0.001) and 25 mg/kg (P<0.001) produced significant antitumor activity. Two of six mice showed complete regression (CR) in both dose groups (FIG. 3). In addition, a positive control SAHA also showed antitumor activity (P<0.001) and one of six mice showed complete regression at 100 mg/kg once every day. (FIG. 3). However, there were no significant changes in body weight at all doses tested (FIG. 4). MPT0L056 showed significant antitumor activity without significantly body weight loss in human RPM18226 multiple myeloma xenograft model.

Evaluation of MPT0L056 Against Human MDA-MB-231 Breast Cancer in Female Nude Mice MPT0L056 was given orally (1.0% carboxyl methyl cellulose (CMC) and 0.5% Tween 80) to 8-week old female nude mice that had been implanted with human MDA-MB-231 breast cell line ($1.0 \times 10^7$ cells in suspension). Mean tumor size on day 1 was ~250 mm³; the study ended when mean tumor volume in the control group approached 2,000 mm³. Tumor size, in mm³, was calculated as:

$$\text{Tumor Volume} = \frac{w^2 \times l}{2}$$

where w=width and l=length in mm of the tumor. Tumor weight can be estimated with the assumption that 1 mg is equivalent to 1 mm³ of tumor volume. The study design is depicted below (Text Table 2).

TEXT TABLE 2

Study Design

| | | Treatment Regimen | | |
|---|---|---|---|---|
| Group | n | Agent | mg/kg | Schedule |
| 1 | 7 | 1.0% CMC + 0.5% Tween 80 | — | QDx~10 |
| 2 | 7 | Bortezomib | 1 | QWK to end |
| 3 | 7 | MPT0L056 | 100 | QDx~10 |
| 4 | 8 | MPT0L056 | 50 | QDx~10 |
| 5 | 7 | MPT0L056 | 25 | QDx~10 |

Figure 5:
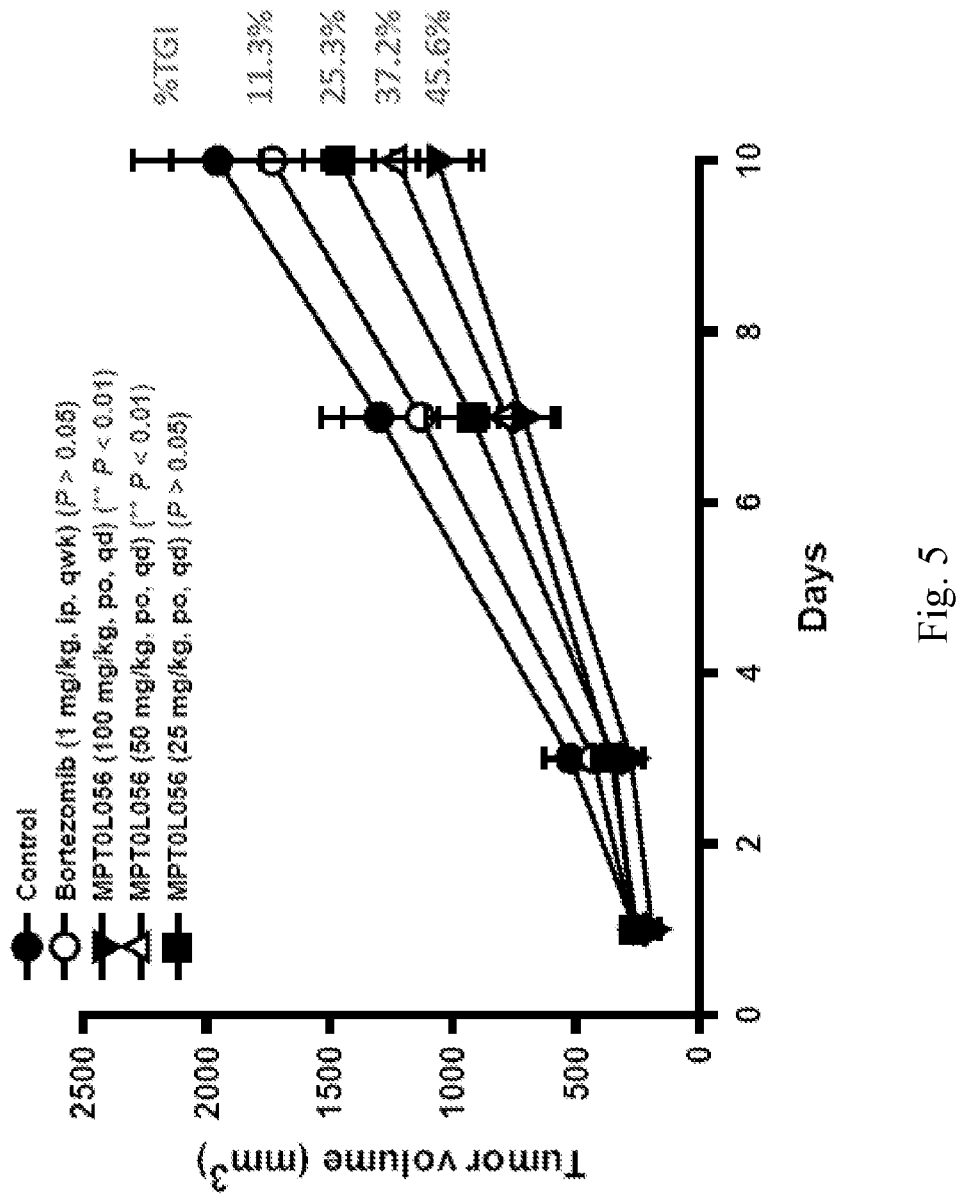
FIG. 5 shows anti-cancer activity of MPT0L056 in human MDA-MB-231 breast adenocarcinoma xenograft model.
Figure 6:
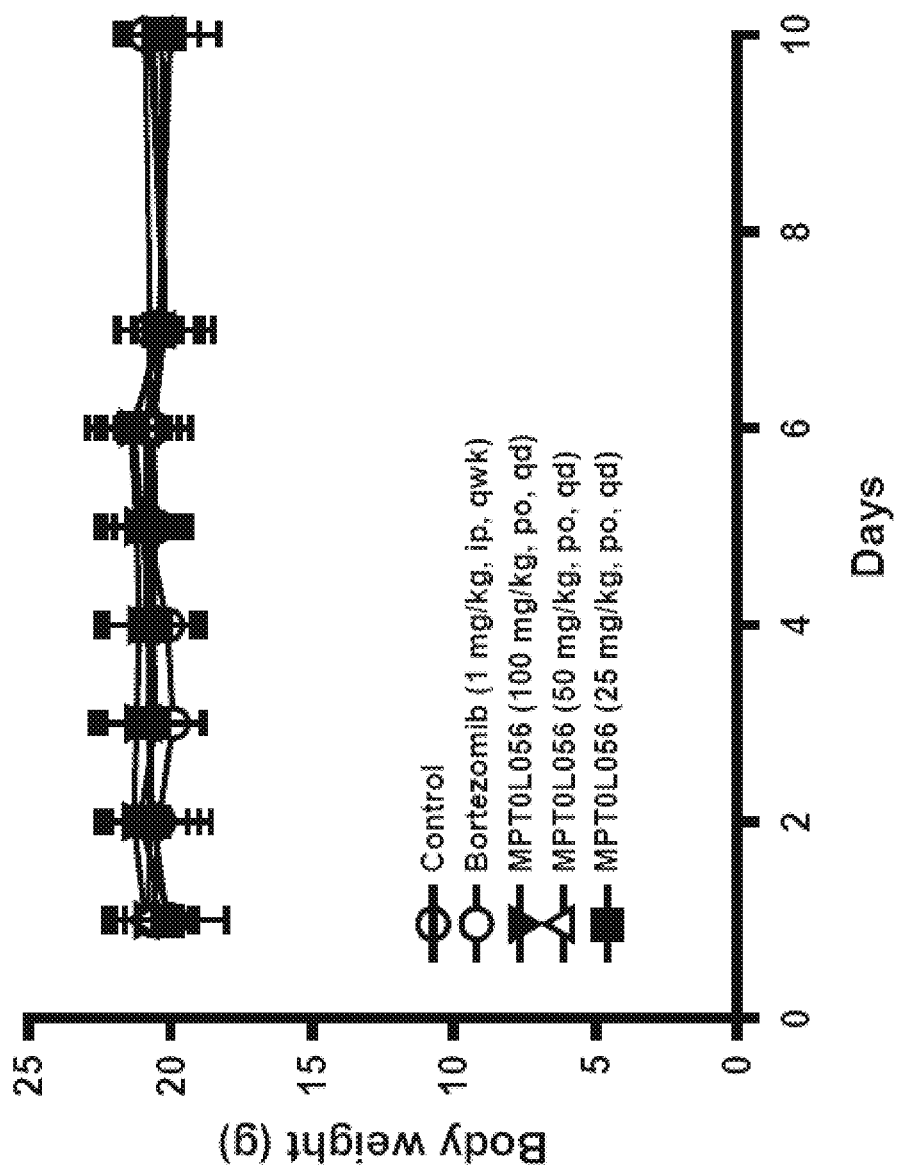
FIG. 6 shows MPT0L056 did not significantly affect the animal body weight.

The TMU-MDA-MB-231-e0002 study was performed according to the protocol in Table 2. This study utilized five groups of mice (n=7-8) bearing established human MDA-MB-231 breast adenocarcinoma with mean volumes of ~250 mm³ on D1. The tumor growth curve and animal body weight change for each treatment group are shown in FIG. 5 and FIG. 6, respectively. FIG. 5 shows MPT0L056 p.o. at 100, 50, and 25 mg/kg once every day for ten days. Based on the Student's t-test analysis, MPT0L056 100 mg/kg ($P<0.01$) and 50 mg/kg ($P<0.01$) produced significant antitumor activity. However, MPT0L056 did not significantly express tumor growth delay at 25 mg/kg (FIG. 5). In addition, a reference group bortezomib did not show antitumor activity ($P>0.05$) (FIG. 5). However, there were no significant changes in body weight at all doses tested (FIG. 6).

Evaluation of MPT0L056 Against Human A2780 Ovarian Cancer in Female Nude Mice

MPT0L056 was given orally (1.0% carboxyl methyl cellulose (CMC) and 0.5% Tween 80) to 8-week old female nude mice that had been implanted with human A2780 ovarian cell line (1.0×10⁷ cells in suspension). Mean tumor size on day 1 was ~150 mm³; the study ended when mean tumor volume in control group approached 4,000 mm³. Tumor size, in mm³, was calculated as:

$$\text{Tumor Volume} = \frac{w^2 \times l}{2}$$

where w=width and l=length in mm of the tumor. Tumor weight can be estimated with the assumption that 1 mg is equivalent to 1 mm³ of tumor volume. The study design is depicted below (Text Table 3).

TEXT TABLE 3

Study Design

| | | Treatment Regimen | | |
|---|---|---|---|---|
| Group | n | Agent | mg/kg | Schedule |
| 1 | 6 | 1.0% CMC + 0.5% Tween 80 | — | QD to end |
| 2 | 5 | Cisplatin | 5 | QWK to end |
| 3 | 6 | Bortezomib | 1 | QWK to end |
| 4 | 6 | MPT0L056 | 100 | QD to end |
| 5 | 6 | MPT0L056 | 200 | QD to end |

Figure 7:
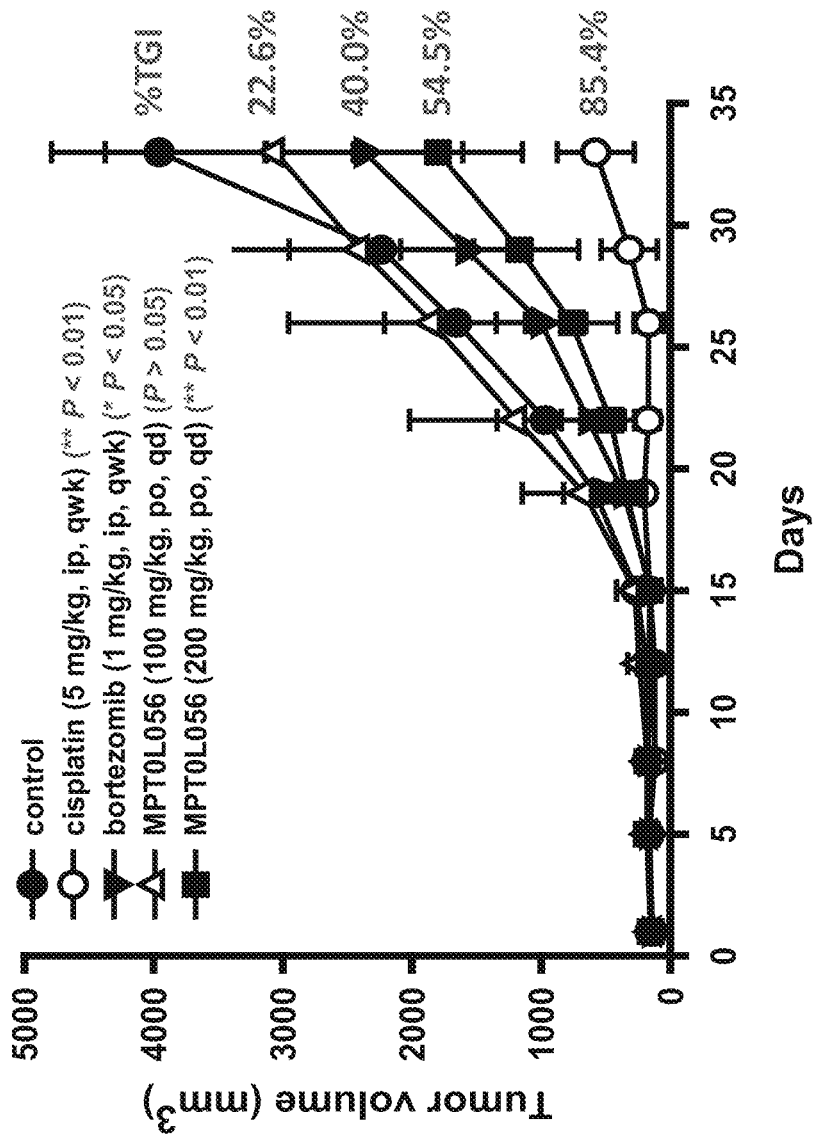
FIG. 7 shows anti-cancer activity of MPT0L056 in human A2780 ovarian adenocarcinoma xenograft model.
Figure 8:
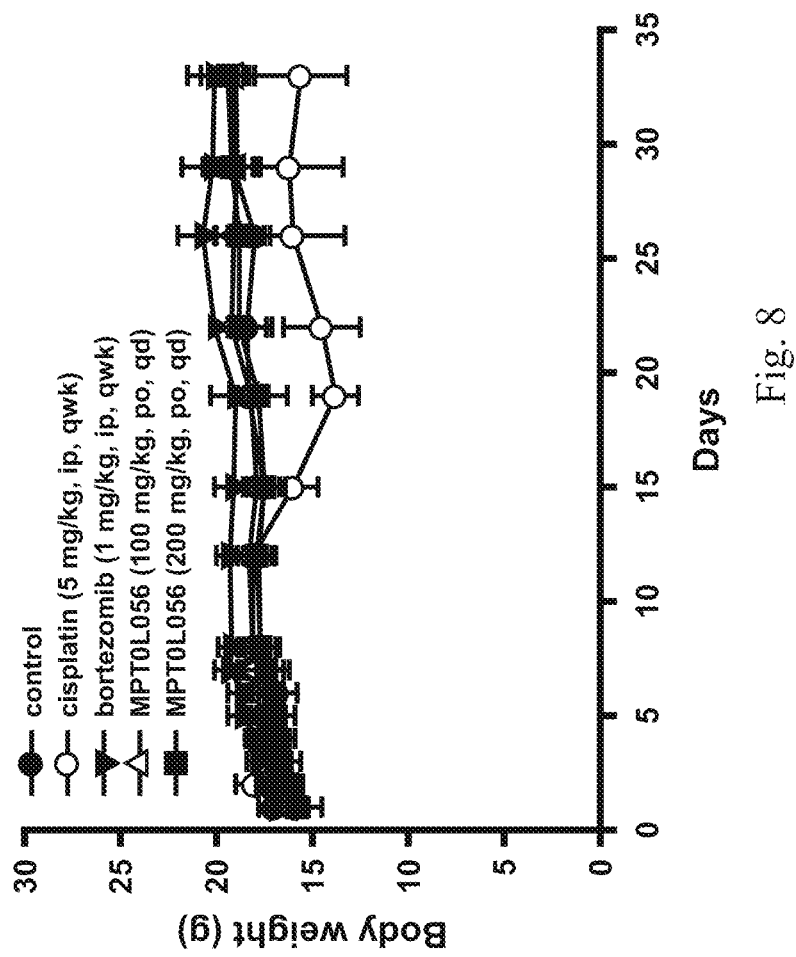
FIG. 8 shows MPT0L056 did not significantly affect the animal body weight.

The TMU-A2780-e0001 study was performed according to the protocol in Table 3. This study utilized five groups of mice (n=5-6) bearing established human 2780 ovarian adenocarcinoma with mean volumes of ~150 mm³ on D1. The tumor growth curve and animal body weight change for each treatment group are shown in FIG. 7 and FIG. 8, respectively. FIG. 7 shows MPT0L056 p.o. at 100 and 200 mg/kg once every day to the end. Based on the Student's t-test analysis, MPT0L056 200 mg/kg ($P<0.01$), but not 50 mg/kg ($P>0.05$) produced significant antitumor activity. In addition, a reference group bortezomib ($P<0.05$) and positive control cisplatin ($P<0.01$) showed antitumor activity (FIG. 7). However, there were no significant changes in body weight at all doses tested (FIG. 8).

Evaluation of MPT0L056 Alone and in Combination with HDAC Inhibitor MPT0E028 Against Human HCT116 Colorectal Adenocarcinoma in Nude Mice MPT0L056 was used to evaluate for activity against the HCT116 human colorectal adenocarcinoma. MPT0L056 was given orally at 50 and 100 mg/kg (1.0% carboxyl methyl cellulose (CMC) and 0.5% Tween 80 in D5W) to 8-week old female nude mice that had been implanted with the HCT116 colorectal cancer cell line (1.0×10⁷ cells in suspension). Mean tumor size on day 1 was ~160 mm³; the study ended when individual tumor volumes approached 1,000 mm³ over ~59 days. Tumor size, in mm³, was calculated as:

$$\text{Tumor Volume} = \frac{w^2 \times l}{2}$$

where w=width and l=length in mm of the tumor. Tumor weight can be estimated with the assumption that 1 mg is equivalent to 1 mm3 of tumor volume. However, MPT0E028 was administered orally (p.o.) in 1.0% CMC and 0.5% Tween 80 and given dose at 25 mg/kg daily to end schedule. In addition, Bortezomib was administered intravenous (i.v.) in D5W and given dose at 1 mg/kg weekly until the end of the scheduled regimen. The study design is depicted below (Text Table 4).

TEXT TABLE 4

Study Design
Protocol Design For The TMU-HCT116-e0001 Study

| | | Treatment Regimen 1 | | | | Treatment Regimen 2 | | | |
|---|---|---|---|---|---|---|---|---|---|
| Group | n | Agent | mg/kg | Route | Schedule | Agent | mg/kg | Route | Schedule |
| 1 | 8 | control | | po | qd to endpoint | | | | |
| 2 | 7 | MPT0E028 | 25 | po | qd to endpoint | | | | |

TEXT TABLE 4-continued

Study Design
Protocol Design For The TMU-HCT116-e0001 Study

| | | Treatment Regimen 1 | | | | Treatment Regimen 2 | | | |
|---|---|---|---|---|---|---|---|---|---|
| Group | n | Agent | mg/kg | Route | Schedule | Agent | mg/kg | Route | Schedule |
| 3 | 8 | bortezomib | 1 | iv | qwk to endpoint | | | | |
| 4 | 8 | MPT0L056 | 100 | po | qd to endpoint | | | | |
| 5 | 8 | MPT0L056 | 50 | po | qd to endpoint | | | | |
| 6 | 8 | bortezomib | 1 | iv | qwk to endpoint | MPT0E028 | 25 | po | qd to endpoint |
| 7 | 8 | MPT0L056 | 100 | po | qd to endpoint | MPT0E028 | 25 | po | qd to endpoint |
| 8 | 8 | MPT0L056 | 50 | po | qd to endpoint | MPT0E028 | 25 | po | qd to endpoint |

Each animal was euthanized when the tumors reached the predetermined endpoint size of 1,000 mm$^3$. The time to endpoint (TTE) for each mouse was calculated by the following equation:

$$TTE = \frac{\log_{10}(\text{endpoint volume}) - b}{m}$$

where TTE is expressed in days, endpoint volume is in mm$^3$, b is the intercept, and m is the slope of the line obtained by linear regression of a log-transformed tumor growth data set. The data set is comprised of the first observation that exceeded the study endpoint volume and the three consecutive observations that immediately preceded the attainment of the endpoint volume. The calculated TTE is usually less than the day on which an animal is euthanized for tumor size. Animals that did not reach the endpoint were euthanized at the end of the study, and assigned a TTE value equal to the last day (59 days). An animal classified as having died from treatment-related (TR) causes or non-treatment-related metastasis (NTRm) causes was assigned a TTE value equal to the day of death. An animal classified as having died from non-treatment-related (NTR) causes was excluded from TTE calculations.

Treatment efficacy was determined from tumor growth delay (TGD), which is defined as the increase in the median TTE for a treatment group compared to the control group:

TGD=T-C, expressed in days, or as a percentage of the median TTE of the control group:

$$\% \, TGD = \frac{T-C}{C} \times 100$$

where:
T=median TTE for a treatment group,
C=median TTE for control Group 1.

Treatment efficacy was also determined from the tumor volumes of animals remaining in the study on the last day, and from the number of regression responses. The MTV(n) is defined as the median tumor volume on D59 in the number of animals remaining, n, whose tumors have not attained the endpoint volume.

Treatment may cause a partial regression (PR) or a complete regression (CR) of the tumor in an animal. A PR indicates that the tumor volume was 50% or less of its D1 volume for three consecutive measurements during the course of the study, and equal to or greater than 50 mm$^3$ for one or more of these three measurements. A CR indicates that the tumor volume was less than 50 mm$^3$ for three consecutive measurements during the course of the study. An animal with a CR at the termination of a study is additionally classified as a tumor-free survivor (TFS).

Animals were weighed daily for the first five days, then twice weekly until the completion of the study. The mice were examined frequently for overt signs of any adverse, drug-related side effects. Acceptable toxicity for the MTD of cancer drugs is defined as a group mean BW loss of 20% or less during the test, and not more than one TR death among ten animals. A death is classified as TR if there is evidence of treatment side effects from clinical signs and/or necropsy or from unknown causes during dosing period or within 10 days of the last dose. A death is classified as NTR if there is no evidence that the death was related to treatment side effects. A death is classified as NTRm if necropsy indicates that it may have resulted from tumor dissemination by invasion and/or metastasis.

The logrank test was used to determine the statistical significance of the difference between the TTE values of two groups, except any NTR deaths. Statistical and graphical analyses were performed with Prism 3.03 (GraphPad) for Windows. The two-tailed statistical analyses were conducted at P=0.05. Kaplan-Meier plots show the percentage of animals remaining in the study versus time. The Kaplan-Meier plots use the same data set as the logrank test. The tumor growth curves show the group median tumor volume, on a log scale as a function of time. When an animal exits the study due to tumor size or TR death, the final tumor volume recorded for the animal is included with the data used to calculate the median at subsequent time points. Therefore, the final median tumor volume shown by the curve may differ from the MTV, which is the median tumor volume for mice remaining in the study on the last day (excluding all with tumors that have attained the endpoint). If more than one TR death occurs in a group, the tumor growth curves are truncated at the time of the last measurement that precedes the second TR death. Tumor growth curves are also truncated when the tumors in more than 50% of the assessable animals in a group have grown to the endpoint volume.

Figure 9:
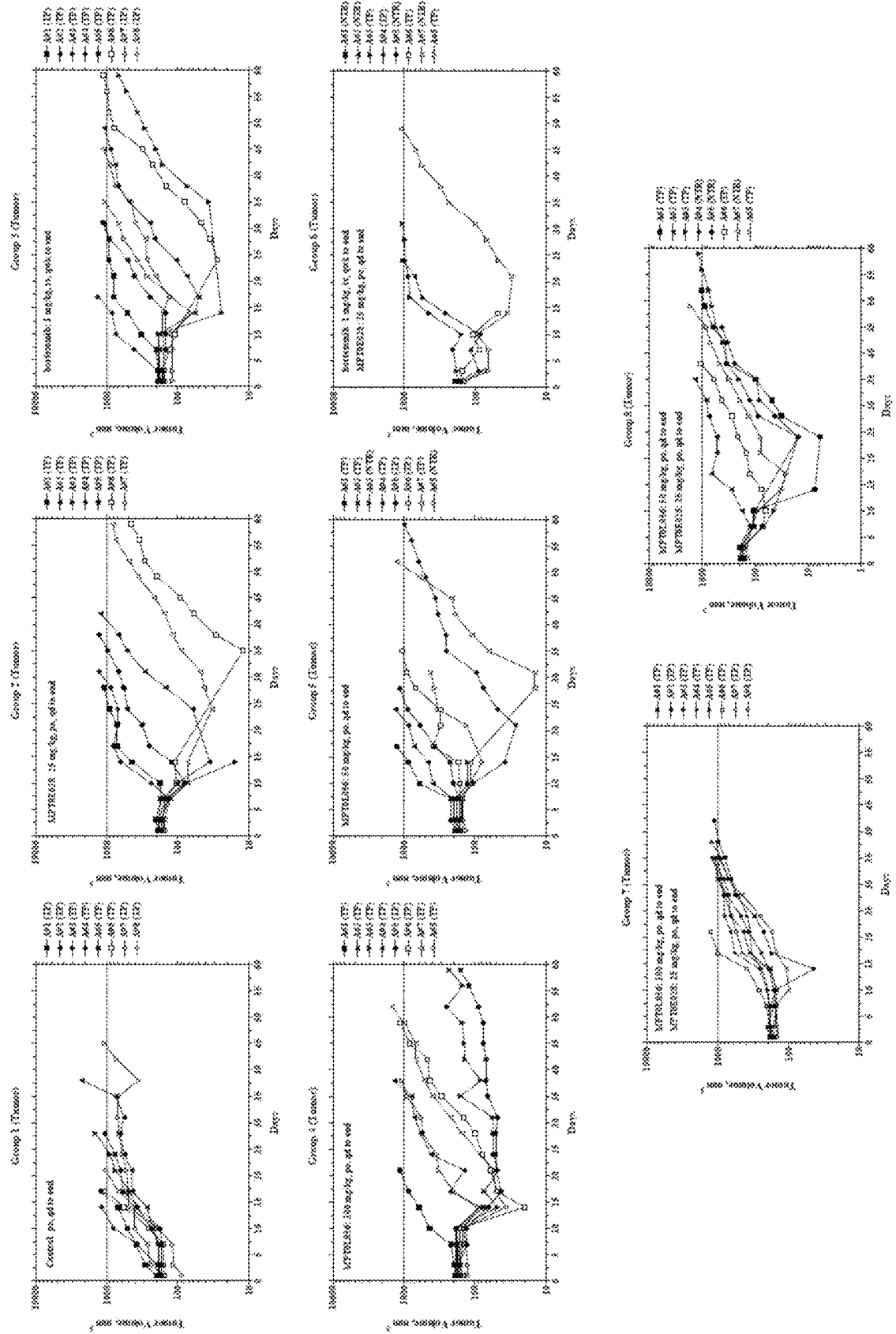
FIG. 9 shows individual tumor growth curve in the study.
Figure 10:
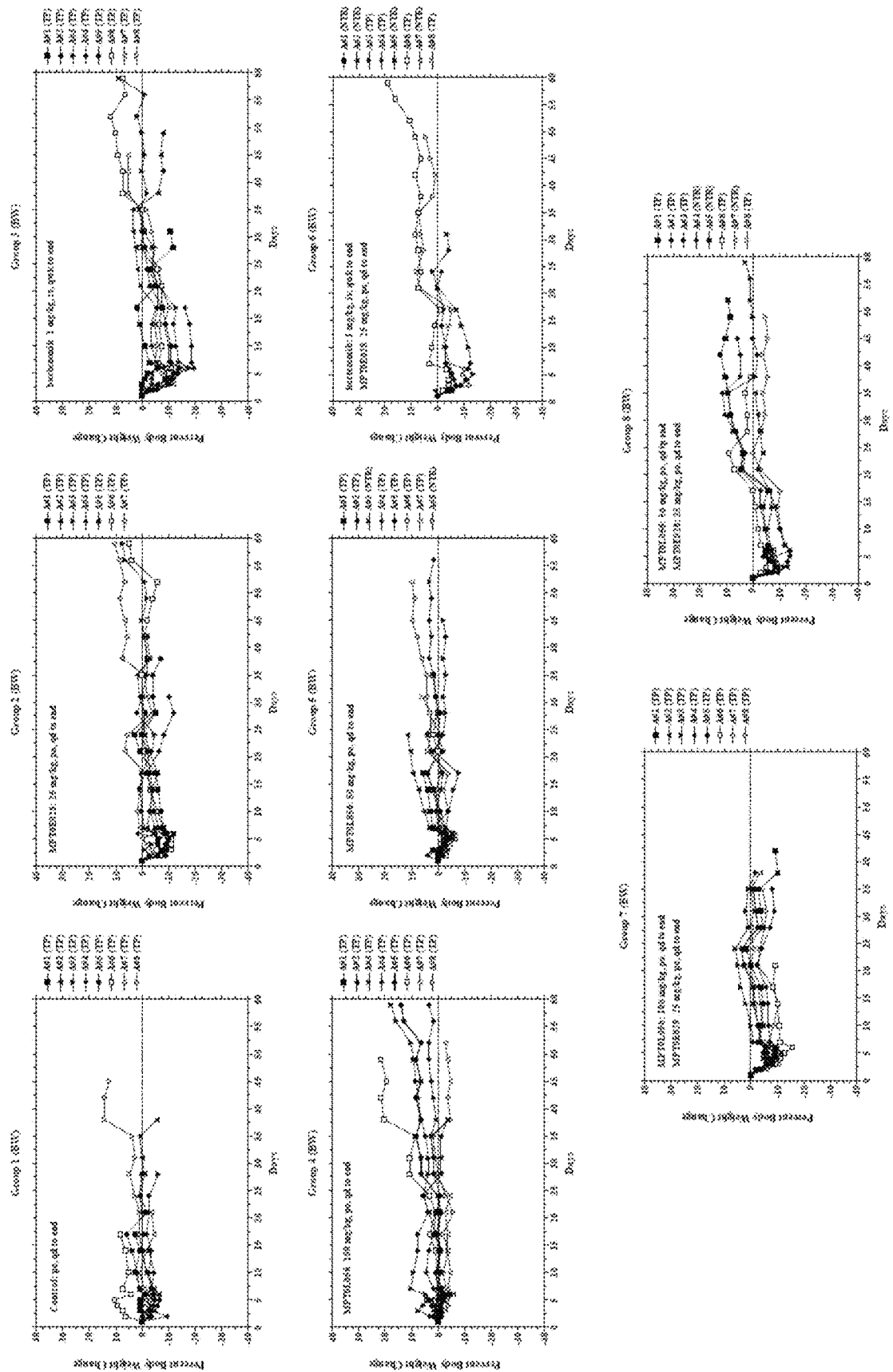
FIG. 10 shows individual animal body weight change in the study.
Figure 11:
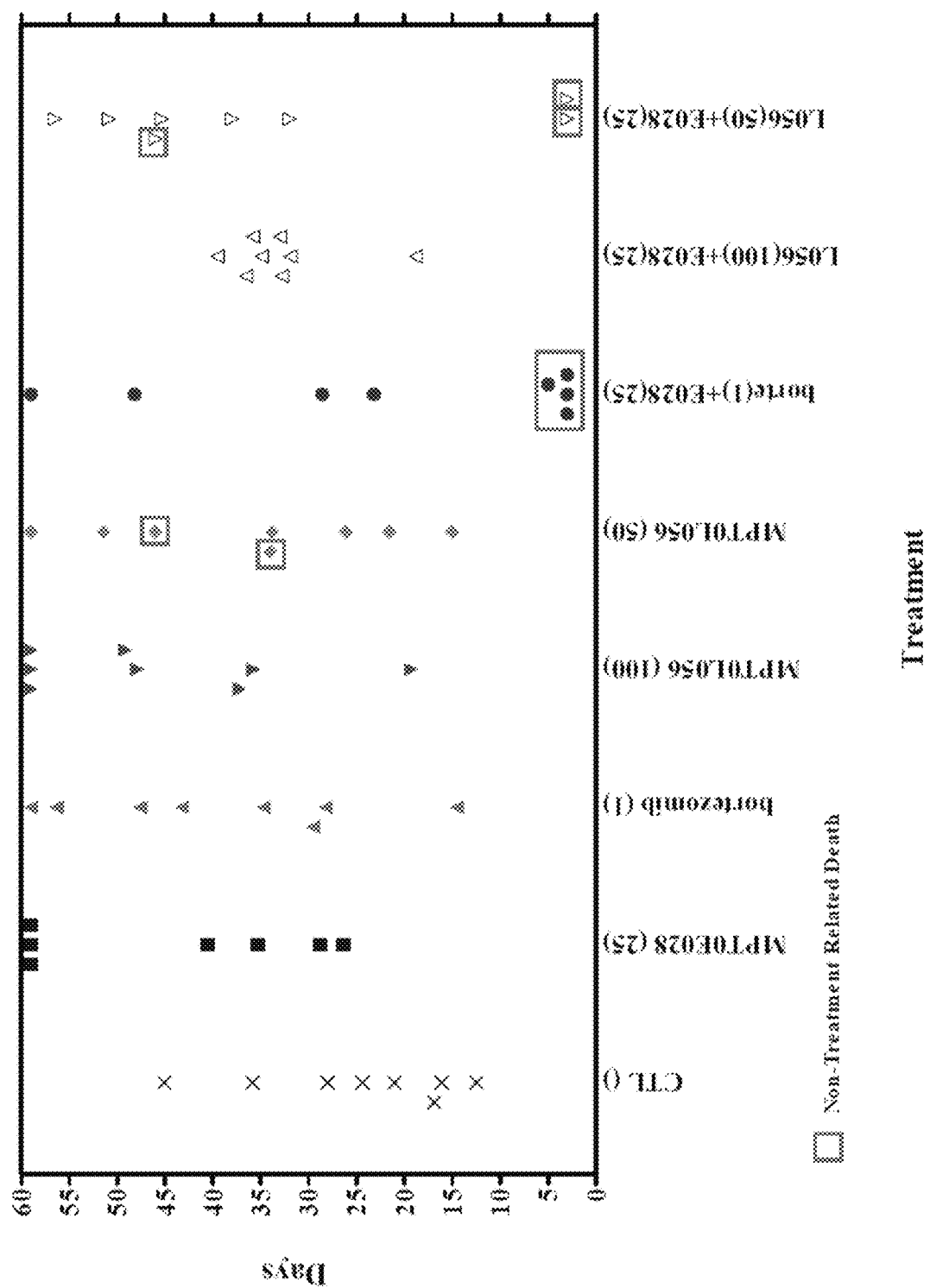
FIG. 11 shows individual times to endpoint for mice in the study.
Figure 12:
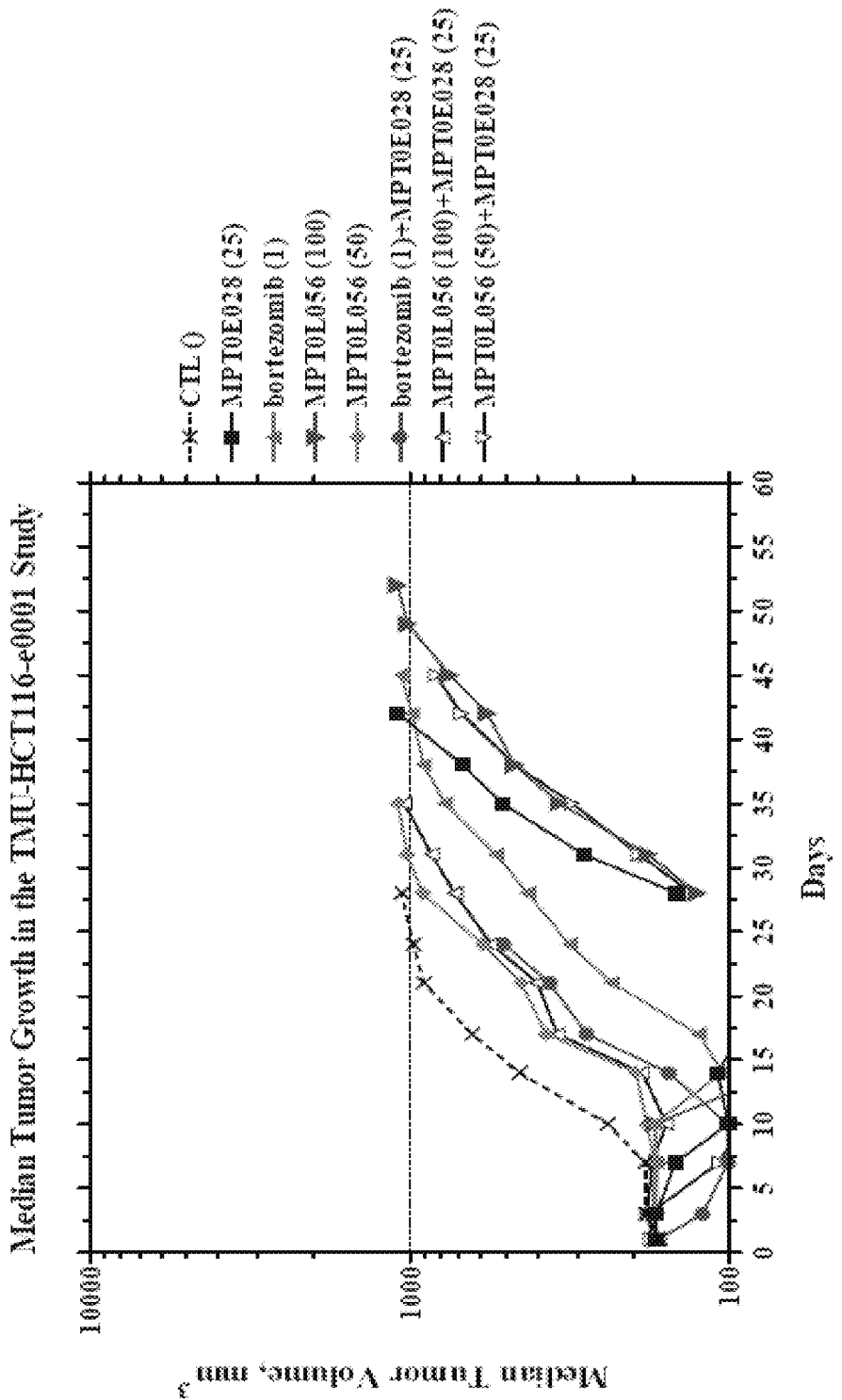
FIG. 12 shows median tumor growth in the TMU-HCT-116-e0001 study.

The 59-day study utilized eight groups of mice (n=7-8) bearing established HCT116 human colorectal adenocarcinoma cells with mean volumes of ~160 mm$^3$ on D1. Table 5 summarizes the treatment response and the statistical results. The complete statistical analysis data from the logrank analysis is shown in Table 6. The individual tumor growth curve and individual animal body weight change for each treatment group are shown in FIG. 9 and FIG. 10, respectively. FIG. 11 shows the TTE values for individual mice in each treatment group in a scatterplot. The median tumor growth and Kaplan-Meier curves, for each group, are included in the upper and lower panels, respectively, in FIG. 12.

Growth of Human HCT116 Colorectal Adenocarcinoma in Control Mice

Group 1 mice received vehicle and served as the control for all treatment groups. All tumors in the control mice grew to the 1,000 mm$^3$ endpoint volume (FIG. 9). The median TTE for Group 1 mice was 22.7 days (Table 6).

Response of Human HCT116 Colorectal Adenocarcinoma to MPT0E028

MPT0E028 (Group 2) p.o. at 25 mg/kg once every day to end produced a median TTE of 40.5 days, corresponding to a 17.8-day T–C and a % TGD of 78. Based on the logrank analysis, MPT0E028 produced significant antitumor activity (P=0.0197, logrank test, Tables 5 and 6). Median tumor volume (MTV) was 454 mm$^3$ for three mice at the end of the study. There were two PR mice and two CR mice in this study. However, there was one mouse to show the tumor-free survivor (TFS) during the study.

Response of Human HCT116 Colorectal Adenocarcinoma to Bortezomib

Bortezomib (Group 3) i.v. at 1.0 mg/kg once every week to end produced a median TTE of 38.9 days, corresponding to a 16.2-day T–C and a % TGD of 71. Based on the logrank analysis, bortezomib produced significant antitumor activity (P=0.0389, logrank test, Tables 5 and 6). Median tumor volume (MTV) was 683 mm$^3$ for one mouse at the end of the study. There were one PR mice and two CR mice in this study.

Response of Human HCT 116 Colorectal Adenocarcinoma to MPT0L056

MPT0L056 (Groups 4 and 5) p.o. at 100 and 50 mg/kg once every day to endpoint, produced a median TTE of 48.5 and 30.0 days, respectively, corresponding to 25.8- and 7.3-day T–C, and % TGD of 114 and 32 for the 100 and 50 mg/kg treated group (Groups 4 and 5). Based on the logrank analysis, MPT0L056 at 100 mg/kg, but not 50 mg/kg (P=0.2087), produced significant antitumor activity (P=0.0033, logrank test, Tables 3 and 4). Median tumor volume (MTV) was 160 mm3 for three mice in 100 mg/kg-treated group, and 975 mm$^3$ for one mouse in 50 mg/kg-treated group at the end of the study. There were four PR mice and one CR mouse in 100 mg/kg-treated group, and one PR mouse and two CR mice in 50 mg/kg-treated group. However, there was one mouse to show the tumor-free survivor (TFS) during the 100 mg/kg-treated study.

Response of Human HCT116 Colorectal Adenocarcinoma to Combine Bortezomib with MPT0E028

Bortezomib (Group 6) i.v. at 1.0 mg/kg once every week to endpoint, combined with MPT0E028 p.o. at 25 mg/kg once every day to endpoint, produced a median TTE of 38.4 days, respectively, corresponding to 15.7-day T–C, and % TGD of 69. Based on the logrank analysis, bortezomib at 1.0 mg/kg combined with MPT0E028 did not produce significant synergistic effects of antitumor activity (Tables 5 and 6). Median tumor volume (MTV) was 0 mm$^3$ for one mouse at the end of the study. There were one PR mouse and one CR mouse in this study. However, there was also one mouse to show the tumor-free survivor (TFS) during the study.

Response of Human HCT116 Colorectal Adenocarcinoma to Combine MPT0L056 with MPT0E028

MPT0L056 (Groups 7 and 8) p.o. at 100 and 50 mg/kg once every day to endpoint, combined with MPT0E028 p.o. at 25 mg/kg once every day to endpoint, produced a median TTE of 34.0 and 45.3 days, respectively, corresponding to 11.3- and 22.6-day T–C, and % TGD of 50 and 100 for the 100 and 50 mg/kg treated group (Group 7 and 8). Based on the logrank analysis, MPT0L056 at 50 mg/kg (P=0.0096), but not 100 mg/kg (P=0.4348), combined with MPT0E028 to produce significant synergistic effect of antitumor activity (Tables 5 and 6). However, there were one PR mouse and three CR mice in the 50 mg/kg-treated group.

TABLE 5

Treatment Response Summary For The TMU-HCT116-e0001 Study

| Group | n | Treatment Regimen 1 | | | | Treatment Regimen 2 | | | | Median TTE |
|---|---|---|---|---|---|---|---|---|---|---|
| | | Agent | mg/kg | Route | Schedule | Agent | mg/kg | Route | Schedule | |
| 1 | 8 | control | | po | qd to endpoint | | | | | 22.7 |
| 2 | 7 | MPT0E028 | 25 | po | qd to endpoint | | | | | 40.5 |
| 3 | 8 | bortezomib | 1 | iv | qwk to endpoint | | | | | 38.9 |
| 4 | 8 | MPT0L056 | 100 | po | qd to endpoint | | | | | 48.5 |
| 5 | 8 | MPT0L056 | 50 | po | qd to endpoint | | | | | 30.0 |
| 6 | 8 | bortezomib | 1 | iv | qwk to endpoint | MPT0E028 | 25 | po | qd to endpoint | 38.4 |
| 7 | 8 | MPT0L056 | 100 | po | qd to endpoint | MPT0E028 | 25 | po | qd to endpoint | 34.0 |
| 8 | 8 | MPT0L056 | 50 | po | qd to endpoint | MPT0E028 | 25 | po | qd to endpoint | 45.3 |

| Group | T-C | % TGD | MTV (a) Day 59 | No. of PR | No. of CR | No. of LTTFS | Logrank Significance | Max % BW Loss Day | No. of TR | No. of NTR |
|---|---|---|---|---|---|---|---|---|---|---|
| 1 | — | — | —(0) | 0 | 0 | 0 | | −2.3%, Day 6 | 0 | 0 |
| 2 | 17.8 | 78% | 454 (3) | 2 | 2 | 1 | * | −7.7%, Day 5 | 0 | 0 |
| 3 | 16.2 | 71% | 683 (1) | 1 | 2 | 0 | * | −13.0%, Day 6 | 0 | 0 |
| 4 | 25.8 | 114% | 160 (3) | 4 | 1 | 1 | ** | −2.3%, Day 6 | 0 | 0 |
| 5 | 7.3 | 32% | 975 (1) | 1 | 2 | 0 | ns | −3.8%, Day 5 | 0 | 2 |
| 6 | 15.7 | 69% | 0 (1) | 1 | 1 | 1 | ns | −6.6%, Day 3 | 0 | 4 |

TABLE 5-continued

Treatment Response Summary For The TMU-HCT116-e0001 Study

| 7 | 11.3 | 50%  | —(0) | 0 | 0 | 0 | ns | −8.4%, Day 5 | 0 | 0 |
| 8 | 22.6 | 100% | —(0) | 1 | 3 | 0 | ** | −9.5%, Day 3 | 0 | 3 |

Study Endpoint = 1000 mm$^3$, Days in Progress = 59
n = number of minerals in a group not dead 8 cm accidental or unknown causes, or enthanized for sampling
TTE = time to endpoint;
T-C = difference between median TTE (days) of treated versus control group;
% TGD = [(T-C)/C] × 100
MTV (a) = median tumor volume (mm$^3$) for the number of animals on the day of TGD analysis (excludes animals with tumor volume at endpoint)
PR = partial regression;
CR = complete regression;
TFS = tumor-free survivor
Statistical Significance = Logrank test;
ne = not evaluable
ns = not significant,
* = P < 0.05;
** = P < 0.01;
*** = P < 0.001, compared with Group 1
Mean BW Nadir = lowest group mean body weight, as % change from Day 1;
— indicates no decrease in mean body weight was observed
TR = treatment-related death;
NTR = non-treatment-related death

TABLE 6

| Groups Compared | control po:qd to endpoint Group 1 vs 2 MPT0E028 po:qd to endpoint 25 mg/kg | control po:qd to endpoint Group 1 vs 3 bortezomib iv:qwk to endpoint 1 mg/kg | control po:qd to endpoint Group 1 vs 4 MPT0L056 po:qd to endpoint 100 mg/kg | control po:qd to endpoint Group 1 vs 5 MPT0L056 po:qd to endpoint 50 mg/kg | control po:qd to endpoint Group 1 vs 6 bortezomib iv:qwk to endpoint MPT0E028 po:qd to endpoint 1/25 mg/kg | control po:qd to endpoint Group 1 vs 7 MPT0L056 po:qd to endpoint MPT0E028 po:qd to endpoint 100/25 mg/kg | control po:qd to endpoint Group 1 vs 8 MPT0L056 po:qd to endpoint MPT0E028 po:qd to endpoint 50/25 mg/kg |
|---|---|---|---|---|---|---|---|
| Logrank Test | | | | | | | |
| Chi square | 5.441 | 4.227 | 8.631 | 1.58 | 3.124 | 0.6099 | 6.699 |
| df | 1 | 1 | 1 | 1 | 1 | 1 | 1 |
| P value | 0.0197 | 0.0398 | 0.0033 | 0.2087 | 0.0772 | 0.4348 | 0.0096 |
| P value summary | * | * | ** | ns | ns | ns | ** |
| Are the survival curves sig. differences | Yes | Yes | Yes | No | No | No | Yes |
| Median survival | | | | | | | |
| Column A | 22.7 | 22.7 | 22.7 | 22.7 | 22.7 | 22.7 | 22.7 |
| Column B | 40.5 | 38.95 | 48.55 | 29.95 | 38.4 | 33.95 | 45.3 |
| Ratio | 0.5605 | 0.5828 | 0.4676 | 0.7579 | 0.5911 | 0.6686 | 0.5011 |
| 95% CI of ratio | 2.2594 to 0.8616 | 0.2202 to 0.9454 | 0.1404 to 0.7947 | 0.4308 to 1.085 | 0.3259 to 0.8564 | 0.2933 to 1.044 | 0.1740 to 0.8282 |
| Hazard Ratio | | | | | | | |
| Ratio | 3.677 | 2.625 | 4.155 | 1.959 | 2.906 | 1.43 | 3.433 |
| 95% CI of ratio | 1.259 to 14.22 | 1.059 to 10.95 | 1.925 to 26.60 | 0.6036 to 6.532 | 0.8830 to 11.10 | 0.5217 to 4.538 | 1.523 to 20.98 |

Effects of MPT0L056 on IL-6 Production in Murine RAW264.7 Macrophage Cells

Cell Culture.

The RAW264.7 mouse macrophage cells were purchased from the Bioresource Collection and Research Center (Hsinchu, Taiwan) and the cells cultured at 37° C. in 5% CO2/95% air in, respectively, 90% Ham's F-12 or Dulbecco's modified Eagle medium, both containing 10% heat-inactivated fetal bovine serum (FBS) (Invitrogen Life Technologies, Carlsbad, Calif.) and 1% penicillin/streptomycin (Biological Industries, Israel).

IL-6 Determination.

Figure 13:
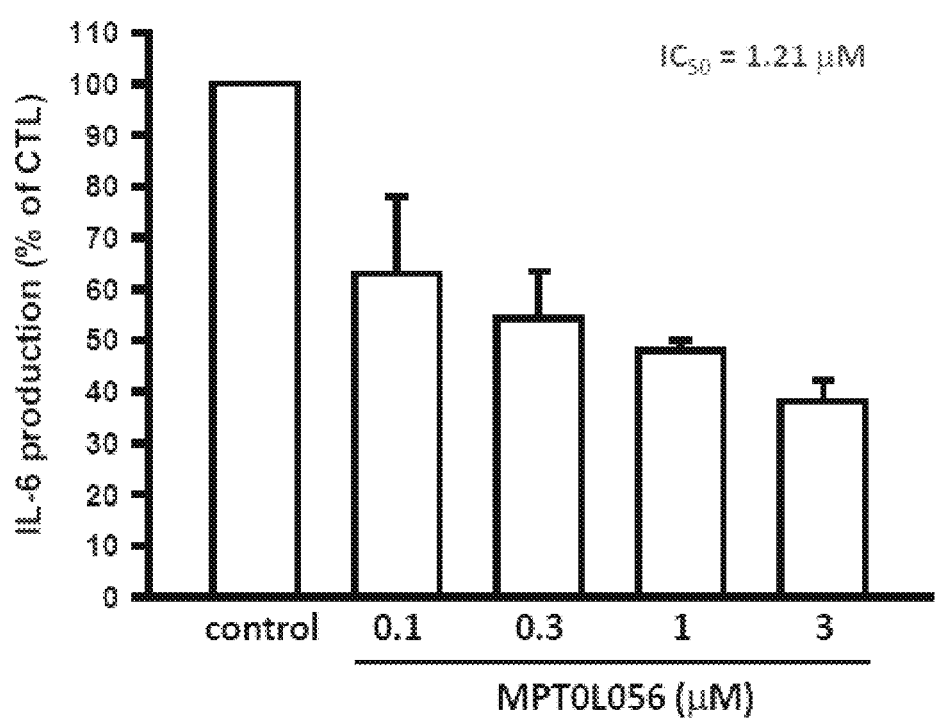
FIG. 13 shows effects of MPT0L056 on IL-6 production in murine RAW264.7 macrophage cells.

To determine the effect of MPT0L056 on the production of cytokine IL-6 from LPS-stimulated cells, RAW 264.7 cells (1×10$^6$) were plated and pretreated in the presence or absence of MPT0L056 for 1 h, and then stimulated with LPS (25 ng/mL) for 24 h at 37° C. Supernatants were collected and the concentration of cytokines IL-6 was measured by ELISA kit. The results are shown in FIG. 13. FIG. 13 shows that MPT0L056 inhibits IL-6 production in murine RAW264.7 macrophage cells (IC50 value is 1.21 μM).

Effects of MPT0L056 on IL-6 Production in Human RAFLS (Rheumatoid Arthritis Fibroblast-Like Synoviocyte) Cells Cell Culture.

Human rheumatoid arthritis fibroblast-like synoviocytes (RAFLS) from Cell Application Inc. (San Diego, Calif., USA) were grown in synoviocyte growth medium from the same supplier.

IL-6 Determination.

Figure 14:
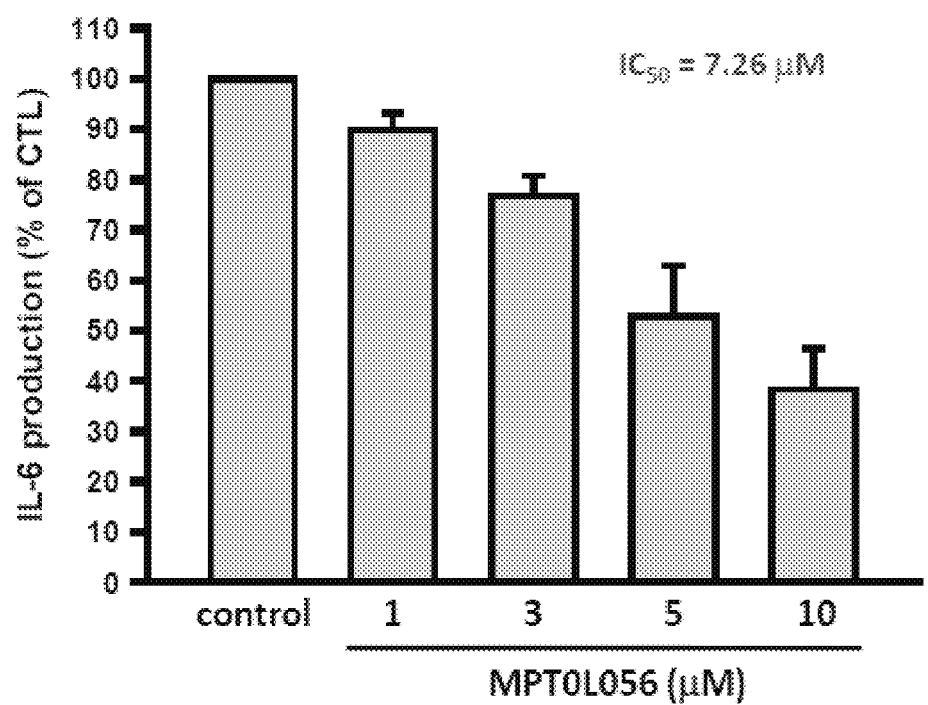
FIG. 14 shows effects of MPT0L056 on IL-6 production in human RAFLS (rheumatoid arthritis fibroblast-like synoviocyte) cells.

RA-FLS (2.5×10$^4$) was treated with various concentrations of MPT0L056 for 24 h, then the medium was collected and assayed for IL-6 using commercial ELISA kit. The results are shown in FIG. 14. As shown in FIG. 14, MPT0L056 inhibits IL-6 production in human rheumatoid arthritis fibroblast-like synoviocyte cells (IC50 value is 7.26 μM).

MPT0L056 Inhibits Development of Arthritis in an Adjuvant-Induced Arthritis (AIA) Model In Vivo Adjuvant-Induced Arthritis (AIA) Model.

Figure 15:
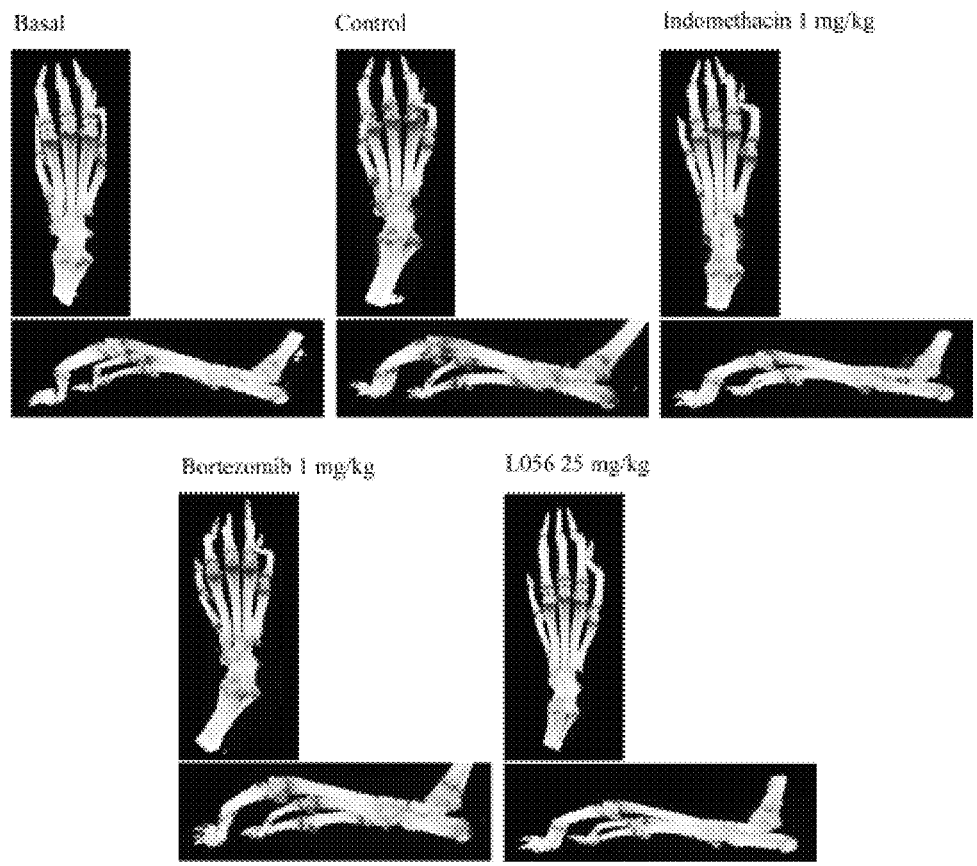
FIG. 15 shows that MPT0L056 inhibits development of arthritis in an adjuvant-induced arthritis (AIA) model using micro-CT scanning.
Figure 16:
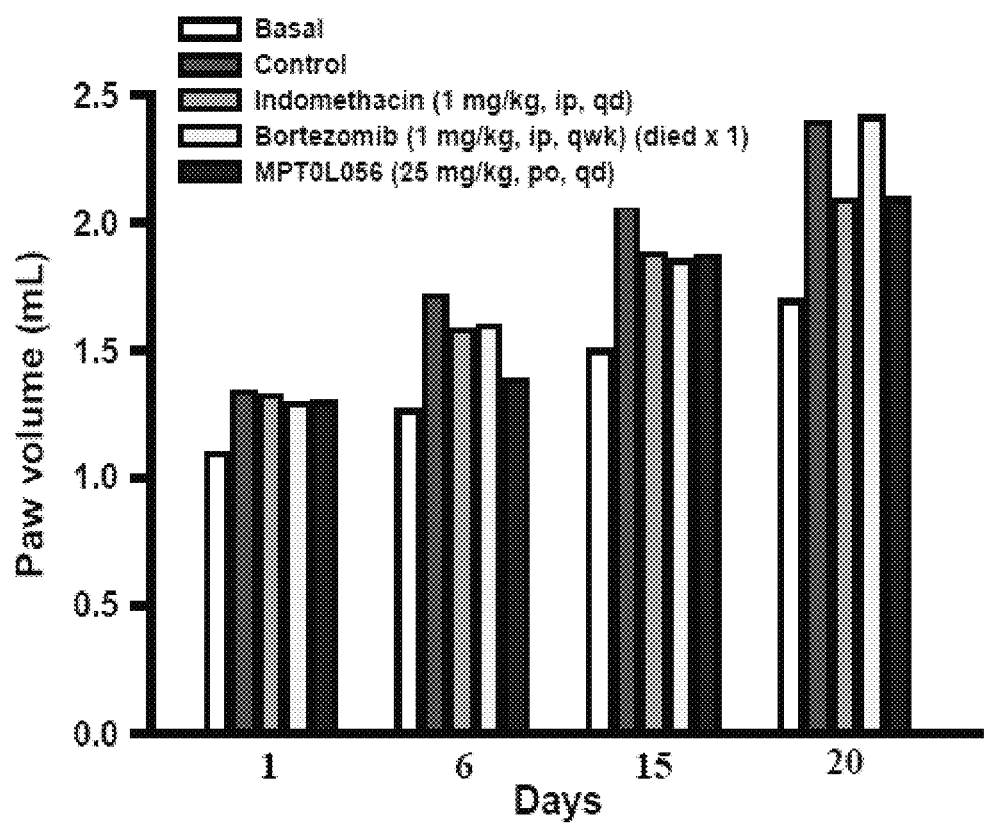
FIG. 16 shows that MPT0L056 exhibits a significant reduction in paw swelling.

Five-week-old male Lewis rats were obtained from the National Laboratory Animal Center (Taipei, Taiwan). Complete Freund's adjuvant (CFA) was prepared by suspending heat-killed *Mycobacterium butyricum* (Difco) in mineral oil at 3 mg/mL. CFA-induced arthritis was induced by intradermal injection of 100 μL of the CFA emulsion into the base of the right hind paw on day 0. MPT0L056 (25 mg/kg, po, qd), Bortezomib (1 mg/kg, ip, qwk), positive control indomethacin (1 mg/kg, po, qwk), or vehicle was given by gavage from day 2 to day 21. On days 0, 2, 6, 9, 13, 17, and 21, the animals were weighed and both hind paw volumes measured using a digital plethysmometer (Diagnostic & Research Instruments Co. Ltd, Taipei, Taiwan). On day 21, micro-computed tomography (micro-CT) of the paws was performed by the Core Facilities Center of the National Research Program for Biopharmaceuticals using an in vivo micro-CT scanner (Skyscan 1176, Bruker Corp., Kontich, Belgium) at 18 μm resolution and 180° scanning with a rotation step of 0.8o per image, 300 msec integration time, 70 keV photon energy, and 350 μA current. The results are shown in FIGS. 15 and 16. As shown in FIG. 15, MPT0L056 inhibits development of arthritis in adjuvant-induced arthritis. FIG. 16 shows that MPT0L056 significantly reduces paw swelling.

Figure 17:
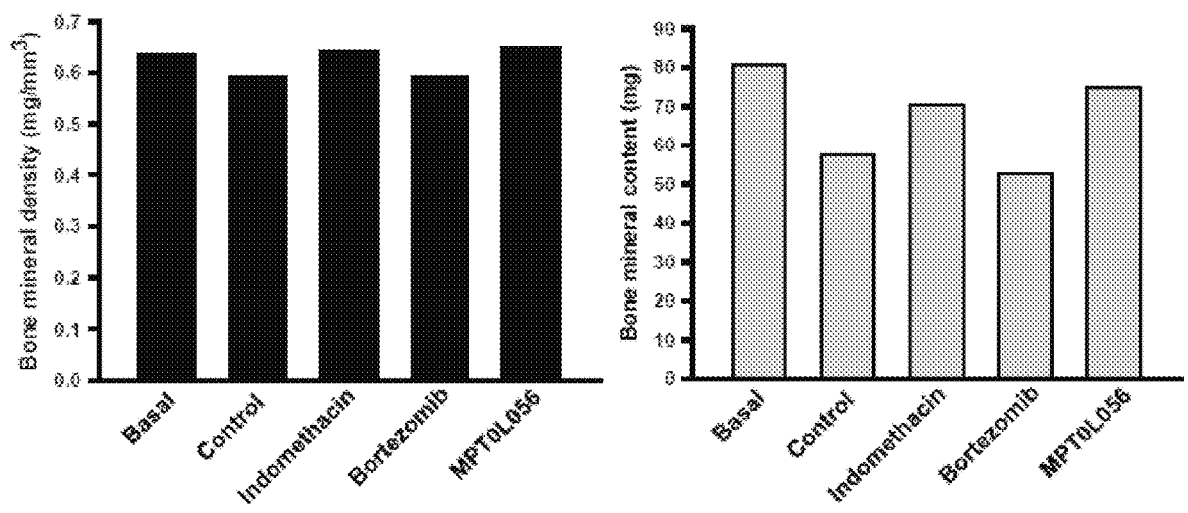
FIG. 17 shows treatment with MPT0L056 to prevent bone mineral density (BMD) and bone mineral content (BMC) loss in AIA model.

Treatment with MPT0L056 to Prevent Bone Mineral Density (BMD and Bone Mineral Content (BMC) Loss in AIA Model Quantification of volumetric bone mineral density (BMD) and bone volume (BV) was performed in a defined bone area ranging 12 mm from tarsals to the end of the calcaneus. The bone mineral content (BMC) was described by the product of BV and BMD. The results are shown in FIG. 17. FIG. 17 shows that treatment with MPT0L056 can prevent bone mineral density (BMD) and bone mineral content (BMC) loss.

EXAMPLES

Example 1 4-(((3-chloro-1,4-dioxo-1,4-dihydronaphthalen-2-yl)amino)methyl)benzoic acid (97)

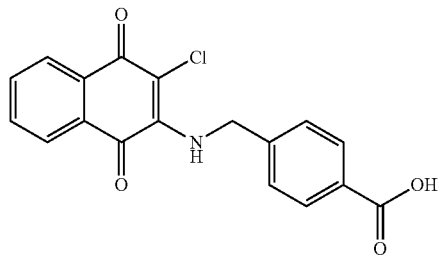 [SMILES: O=C(O)c1ccc(CNC2=C(Cl)C(=O)c3ccccc3C2=O)cc1]

A mixture of 2,3-dichloro-1,4-naphthaquinone (0.49 g, 2.18 mmol), 4-aminomethylbenzoic acid (0.30 g, 1.98 mmol) and TEA (1 ml) was dissolved in EtOH (10 ml) and stirred and refluxed overnight. The residue was filtered by suction filtration to yield a red product. The residue was filtered without further purification to afford 97 (0.36 g, 53.20%) as a red solid. $^1$H-NMR (500 MHz, DMSO-d$_6$): δ 5.01 (d, J=7.0 Hz, 2H), 7.39 (d, J=8.5 Hz, 2H), 7.75 (m, 1H), 7.81 (m, 1H), 7.88 (d, J=8.0 Hz, 2H), 7.96 (d, J=7.5 Hz, 2H), 8.05 (t, J=6.5 Hz, 1H).

Example 2 4-(((3-chloro-1,4-dioxo-1,4-dihydronaphthalen-2-yl)amino)methyl)-N-hydroxybenzamide (1)

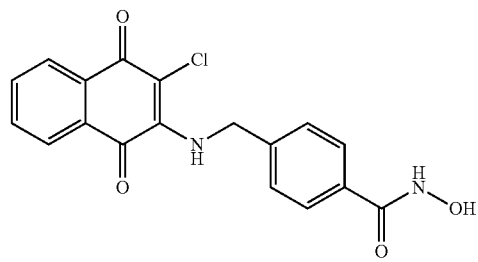 [SMILES: O=C(NO)c1ccc(CNC2=C(Cl)C(=O)c3ccccc3C2=O)cc1]

A mixture of 97 (0.36 g, 1.05 mmol), EDC.HCl (0.30 g, 1.58 mmol), HOBt (0.17 g, 1.26 mmol), NMM (0.28 ml, 2.52 mmol) and DMF (2.5 ml) was stirred for a while, to which was then added the o-(tetrahydro-2H-pyran-2-yl)hydroxylamine (0.15 g, 1.26 mmol) at room temperature, and the mixture was stirred overnight. The residue was purified by flash column over silica gel (ethyl acetate:n-hexane=2:1, Rf=0.45) to obtain the oily product. The oily product was then dissolved in MeOH (3 ml) and 10% TFA (aq.) (3 ml) added at room temperature and the mixture was stirred overnight. H$_2$O was added to the reaction to produce the precipitant. The residue was filtered without further purification to afford 1 (0.24 g, 98.93%) as a red solid. $^1$H-NMR (500 MHz, DMSO-d$_6$): δ 4.98 (s, 2H), 7.35 (d, J=8.5 Hz, 2H), 7.68 (d, J=8.5 Hz, 2H), 7.73 (m, 1H), 7.81 (m, 1H), 7.96 (m, 2H), 8.03 (s, 1H).

Example 3 4-(((3-chloro-1,4-dioxo-1,4-dihydronaphthalen-2-yl)amino)methyl)-N-(pyridin-2-yl)benzamide (2)

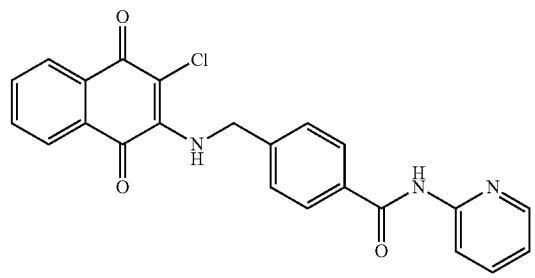 [SMILES: O=C(Nc1ccccn1)c1ccc(CNC2=C(Cl)C(=O)c3ccccc3C2=O)cc1]

A mixture of 97 (0.25 g, 0.73 mmol), EDC.HCl (0.21 g, 1.10 mmol), HOBt (0.12 g, 0.88 mmol), NMM (0.19 ml, 1.75 mmol) and DMF (2.0 ml) was stirred for a while, to which was then added 2-aminopyridine (0.08 g, 0.88 mmol) at room temperature and the mixture was stirred overnight. The residue was purified by flash column over silica gel (dichloromethane:methanol=30:1, Rf=0.50) to afford 2 (0.04 g, 13.11%) as a red solid. ¹H-NMR (300 MHz, CDCl₃): δ 5.15 (d, J=6.6 Hz, 2H), 6.33 (s, 1H), 7.08-7.12 (m, 1H), 7.49 (d, J=8.4 Hz, 2H), 7.67 (m, 1H), 7.77 (m, 2H), 7.97 (d, J=8.4 Hz, 2H), 8.08 (m, 1H), 8.18 (m, 1H), 8.33 (m, 1H), 8.40 (d, J=8.4 Hz, 1H), 8.59 (br, 1H).

Example 4 N-(2-aminophenyl)-4-(((3-chloro-1,4-dioxo-1,4-dihydronaphthalen-2-yl)amino)methyl)benzamide (3)

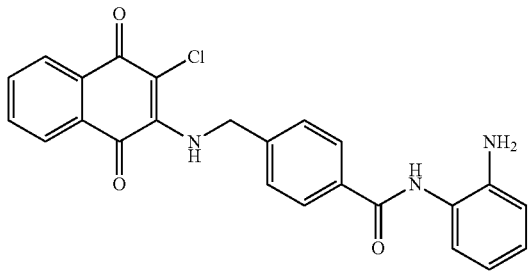 [SMILES: Nc1ccccc1NC(=O)c1ccc(CNC2=C(Cl)C(=O)c3ccccc3C2=O)cc1]

A mixture of 97 (0.25 g, 0.73 mmol), EDC.HCl (0.21 g, 1.10 mmol), HOBt (0.12 g, 0.88 mmol), NMM (0.19 ml, 1.75 mmol) and DMF (2.0 ml) was stirred for a while, to which was then added o-Phenylenediamine (0.08 g, 0.88 mmol) at room temperature and the mixture was stirred overnight. The residue was purified by flash column over silica gel (dichloromethane:methanol=30:1, Rf=0.50) to afford 3 (0.06 g, 19.03%) as a red solid. ¹H-NMR (300 MHz, DMSO-d₆): δ 4.86 (s, 2H), 5.03 (s, 2H), 6.57 (t, J=7.8 Hz, 1H), 6.75 (d, J=6.6 Hz, 1H), 6.95 (t, J=7.8 Hz, 1H), 7.14 (d, J=6.6 Hz, 1H), 7.42 (d, J=7.8 Hz, 2H), 7.74 (t, J=7.2 Hz, 1H), 7.82 (t, J=7.2 Hz, 1H), 7.95 (m, 4H), 8.10 (br, 1H), 9.59 (s, 1H).

Example 5 4-(((3-chloro-1,4-dioxo-1,4-dihydronaphthalen-2-yl)amino)methyl)-N-(pyridin-3-yl)benzamide (4)

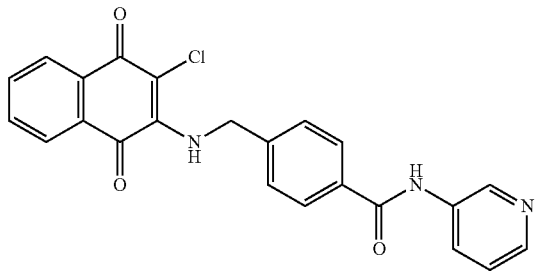 [SMILES: O=C(Nc1cccnc1)c1ccc(CNC2=C(Cl)C(=O)c3ccccc3C2=O)cc1]

A mixture of 97 (0.10 g, 0.29 mmol), HBTU (0.11 g, 0.29 mmol), DIPEA (0.06 ml, 0.35 mmol) and DMF (1.0 ml) was stirred for a while, to which was then added 3-aminopyridine (0.03 g, 0.35 mmol). The reaction was stirred for 16 h at room temperature. The residue was filtered without further purification to afford 4 (0.08 g, 66.02%). ¹H NMR (300 MHz, DMSO-d₆): δ 5.03 (d, J=7.2 Hz, 2H), 7.37 (q, J=4.8 Hz, 1H), 7.46 (d, J=8.1 Hz, 2H), 7.74-7.82 (m, 2H), 7.91 (d, J=8.1 Hz, 2H), 7.95-7.98 (m, 2H), 8.13-8.17 (m, 2H), 8.27-8.29 (m, 1H), 10.42 (s, 1H).

Example 6 4-(((3-chloro-1,4-dioxo-1,4-dihydronaphthalen-2-yl)amino)methyl)-N-(pyridin-3-yl)benzamide (5)

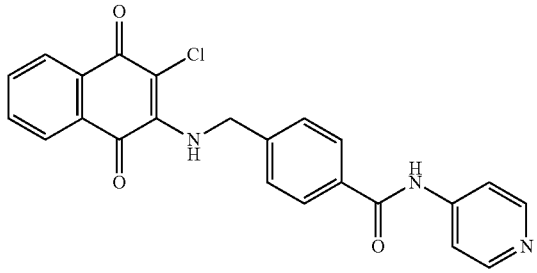 [SMILES: O=C(Nc1ccncc1)c1ccc(CNC2=C(Cl)C(=O)c3ccccc3C2=O)cc1]

A mixture of 97 (0.10 g, 0.29 mmol), HBTU (0.11 g, 0.29 mmol), DIPEA (0.06 ml, 0.35 mmol) and DMF (1.0 ml) was stirred for a while, to which was then added 4-aminopyridine (0.03 g, 0.35 mmol). The reaction was stirred for 16 h at room temperature. The residue was filtered without further purification to afford 5 (0.08 g, 66.02%). ¹H NMR (300 MHz, DMSO-d₆): δ 5.03 (d, J=7.2 Hz, 2H), 7.37 (d, J=8.4 Hz, 2H), 7.73-7.76 (m, 3H), 7.79-7.84 (m, 1H), 7.90 (d, J=8.4 Hz, 2H), 7.95-7.98 (m, 2H), 8.08-8.13 (m, 1H), 8.43-8.45 (m, 2H), 10.53 (s, 1H).

Example 7 4-(((3-chloro-1,4-dioxo-1,4-dihydronaphthalen-2-yl)amino)methyl)-N-(3-fluorophenyl)benzamide (9)

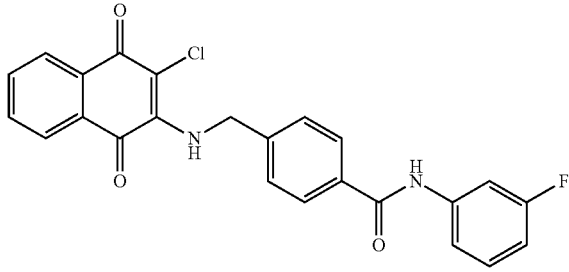 [SMILES: O=C(Nc1cccc(F)c1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-fluoroaniline (0.13 g, 1.32 mmol) at room temperature and the mixture was stirred overnight. The residue was purified by flash column over silica gel (ethyl acetate:n-hexane=1:2, Rf=0.30) to afford 9 (0.04 g, 10.45%) as a red solid. ¹H-NMR (300 MHz, DMSO-d₆): δ 5.03 (s, 2H), 6.92 (m, 1H), 7.36 (m, 1H), 7.45 (d, J=8.1 Hz, 2H), 7.52 (m, 1H), 7.72 (m, 2H), 7.80 (m, 1H), 7.88 (d, J=8.4 Hz, 2H), 7.97 (m, 2H), 8.11 (br, 1H), 10.37 (s, 1H).

Example 8 4-(((3-chloro-1,4-dioxo-1,4-dihydronaphthalen-2-yl)amino)methyl)-N-(4-fluorophenyl)benzamide (10)

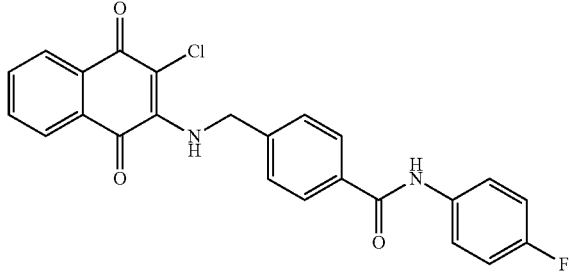 [SMILES: O=C(Nc1ccc(F)cc1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-fluoroaniline (0.13 g, 1.32 mmol) at room temperature and the mixture was stirred overnight. The residue was purified by flash column over silica gel (ethyl acetate:n-hexane=1:2, Rf=0.35) to afford 10 (0.02 g, 5.23%) as a red solid. $^1$H-NMR (300 MHz, DMSO-$d_6$): δ 5.02 (s, 2H), 7.16 (t, J=9.0 Hz, 2H), 7.43 (d, J=8.1 Hz, 2H), 7.75 (m, 3H), 7.82 (m, 1H), 7.88 (d, J=8.4 Hz, 2H), 7.97 (m, 2H), 8.08 (br, 1H), 10.24 (s, 1H).

Example 9 4-(((3-chloro-1,4-dioxo-1,4-dihydronaphthalen-2-yl)amino)methyl)-N-phenylbenzamide (11)

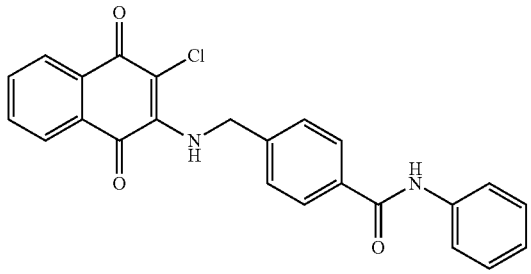 [SMILES: O=C(Nc1ccccc1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added aniline (0.12 g, 1.32 mmol) at room temperature and the mixture was stirred overnight. The residue was filtered by suction filtration to yield a red product. The residue was filtered without further purification to afford 11 (0.28 g, 76.33%) as a red solid. $^1$H-NMR (300 MHz, DMSO-$d_6$): δ 5.02 (s, 2H), 7.07 (t, J=7.5 Hz, 1H), 7.32 (d, J=7.5 Hz, 2H), 7.44 (d, J=8.4 Hz, 2H), 7.75 (m, 3H), 7.83 (m, 1H), 7.88 (d, J=8.4 Hz, 2H), 7.97 (m, 2H), 8.10 (br, 1H); 10.18 (s, 1H).

Example 10 4-(((3-chloro-1,4-dioxo-1,4-dihydronaphthalen-2-yl)amino)methyl)-N-(2-fluorophenyl)benzamide (12)

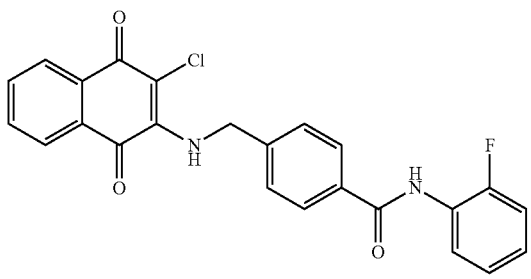 [SMILES: O=C(Nc1ccccc1F)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-fluoroaniline (0.13 g, 1.32 mmol) at room temperature and the mixture was stirred overnight. The residue was purified by flash column over silica gel (ethyl acetate:n-hexane=1:2, Rf=0.25) to afford 12 (0.02 g, 5.23%) as a red solid. $^1$H-NMR (300 MHz, DMSO-$d_6$): δ 5.03 (s, 2H), 7.23 (m, 3H), 7.44 (d, J=8.1 Hz, 2H), 7.56 (t, J=7.5 Hz, 1H), 7.74 (m, 1H), 7.80 (m, 1H), 7.91 (d, J=8.1 Hz, 2H), 7.97 (m, 2H), 8.10 (br, 1H), 10.05 (s, 1H).

Example 11 4-(((3-chloro-1,4-dioxo-1,4-dihydronaphthalen-2-yl)amino)methyl)-N-(thiazol-2-yl)benzamide (13)

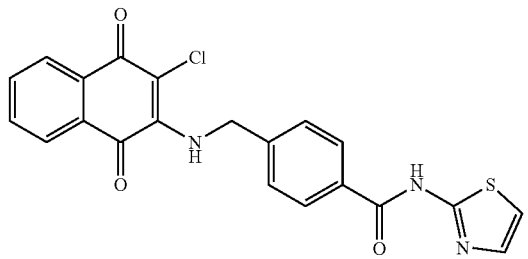 [SMILES: O=C(Nc1nccs1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-aminothiazole (0.13 g, 1.32 mmol) at room temperature and the mixture was stirred overnight. The residue was filtered by suction filtration to yield a red product. The residue was filtered without further purification to afford 13 (0.15 g, 40.21%) as a red solid. $^1$H-NMR (300 MHz, DMSO-$d_6$): δ 5.03 (d, J=7.2 Hz, 2H), 7.26 (d, J=3.6 Hz, 1H), 7.45 (d, J=8.4 Hz, 2H), 7.53 (d, J=3.6 Hz, 1H), 7.75 (m, 1H), 7.82 (m, 1H), 7.97 (m, 2H), 8.04 (d, J=8.4 Hz, 2H), 8.10 (t, J=7.5 Hz, 1H), 12.55 (s, 1H).

Example 12 N-(1H-benzo[d]imidazol-2-yl)-4-(((3-chloro-1,4-dioxo-1,4-dihydronaphthalen-2-yl)amino)methyl)benzamide (14)

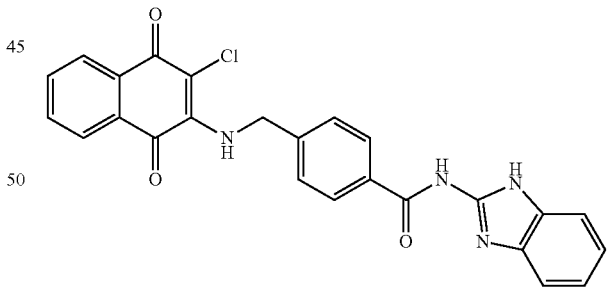

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-aminobenzimidazole (0.18 g, 1.32 mmol) at room temperature and the mixture was stirred overnight. The residue was filtered by suction filtration to yield a red product. The residue was filtered without further purification to afford 14 (0.27 g, 67.16%) as a red solid. $^1$H-NMR (300 MHz, DMSO-$d_6$): δ 5.03 (d, J=6.9 Hz, 2H), 7.11 (m, 2H), 7.43 (d, J=9.0 Hz, 4H), 7.74 (m, 1H), 7.82 (m, 1H), 7.96 (d, J=5.7 Hz, 2H), 8.07 (d, J=8.4 Hz, 3H), 12.22 (s, 1H).

Example 13 4-(((3-chloro-1,4-dioxo-1,4-dihydronaphthalen-2-yl)amino)methyl)-N-(4-hydroxyphenyl)benzamide (15)

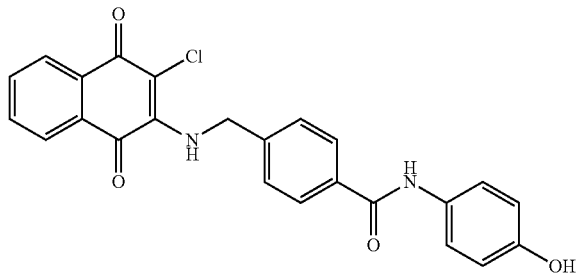 [SMILES: O=C(Nc1ccc(O)cc1)c1ccc(CNC2=C(Cl)C(=O)c3ccccc3C2=O)cc1]

A mixture of 97 (0.15 g, 0.44 mmol), HBTU (0.25 g, 0.66 mmol), DIPEA (0.11 ml, 0.66 mmol) and DMF (2.5 ml) was stirred for a while, to which was then added 4-aminophenol (0.07 g, 0.66 mmol) at room temperature and the mixture was stirred overnight. The residue was purified by flash column over silica gel (ethyl acetate:n-hexane=1:2, Rf=0.30) to afford 15 (0.02 g, 10.50%) as a brown solid. $^1$H-NMR (300 MHz, DMSO-$d_6$): δ 5.01 (d, J=6.3 Hz, 2H), 6.70 (d, J=9.0 Hz, 2H), 7.41 (d, J=8.4 Hz, 2H), 7.48 (d, J=8.7 Hz, 2H), 7.74 (m, 1H), 7.80 (m, 1H), 7.85 (d, J=8.4 Hz, 2H), 7.98 (m, 2H), 8.09 (br, 1H), 9.25 (br, 1H), 9.95 (s, 1H).

Example 14 4-(((3-chloro-1,4-dioxo-1,4-dihydronaphthalen-2-yl)amino)methyl)-N-(3-ethynylphenyl)benzamide (16)

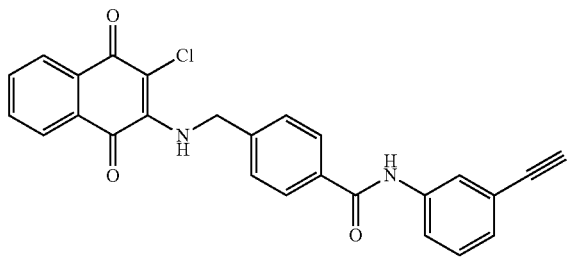 [SMILES: C#Cc1cccc(NC(=O)c2ccc(CNC3=C(Cl)C(=O)c4ccccc4C3=O)cc2)c1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-ethynylaniline (0.15 g, 1.32 mmol) at room temperature and the mixture was stirred overnight. The residue was purified by flash column over silica gel (ethyl acetate:n-hexane=1:4, Rf=0.25) to afford 16 (0.12 g, 30.93%) as a red solid. $^1$H-NMR (300 MHz, DMSO-$d_6$): δ 4.17 (s, 1H), 5.03 (s, 2H), 7.18 (d, J=7.5 Hz, 1H), 7.34 (t, J=8.1 Hz, 1H), 7.45 (d, J=8.4 Hz, 2H), 7.87 (m, 8H), 8.11 (br, 1H), 10.27 (s, 1H).

Example 15 4-(((3-chloro-1,4-dioxo-1,4-dihydronaphthalen-2-yl)amino)methyl)-N-(2-fluoro-4-iodophenyl)benzamide (17)

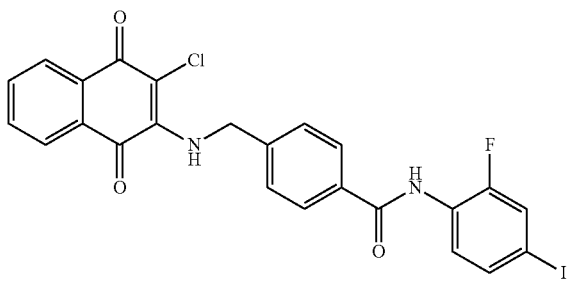 [SMILES: O=C(Nc1ccc(I)cc1F)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-fluoro-4-iodoaniline (0.31 g, 1.32 mmol) at room temperature and the mixture was stirred overnight. The residue was purified by flash column over silica gel (ethyl acetate:n-hexane=1:2, Rf=0.45) to afford 17 (0.02 g, 4.05%) as a red solid. $^1$H-NMR (300 MHz, CDCl$_3$): δ 5.03 (d, J=6.9 Hz, 2H), 7.41 (m, 3H), 7.56 (m, 1H), 7.73 (m, 1H), 7.81 (m, 1H), 7.90 (d, J=8.4 Hz, 2H), 7.96 (m, 2H), 8.10 (m, 1H), 10.09 (s, 1H).

Example 16 N-(1H-benzo[d]imidazol-5-yl)-4-((3-chloro-1,4-dioxo-1,4-dihydronaphthalen-2-ylamino)methyl)benzamide (18)

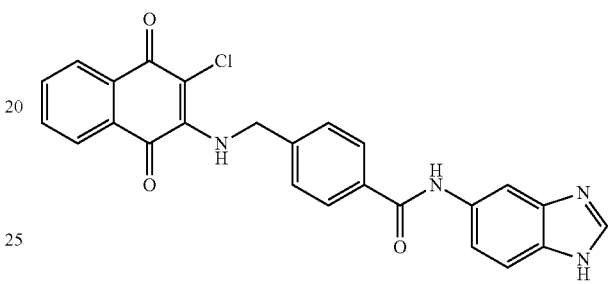

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 5-aminobenzimidazole (0.18 g, 1.32 mmol) at room temperature and the mixture was stirred overnight. The residue was filtered by suction filtration to yield a red product. The residue was filtered without further purification to afford 18 (0.26 g, 64.67%) as a red solid. $^1$H-NMR (300 MHz, DMSO-$d_6$): δ 5.03 (d, J=7.2 Hz, 2H), 7.43-7.48 (m, 3H), 7.54 (d, J=8.7 Hz, 1H), 7.72-7.77 (m, 1H), 7.80-7.85 (m, 1H), 7.91 (d, J=8.4 Hz, 2H), 7.96-7.99 (m, 2H), 8.09-8.15 (m, 2H), 8.20 (s, 1H), 10.20 (s, 1H).

Example 17 2-(4-(3-amino-1H-pyrazole-1-carbonyl)benzylamino)-3-chloronaphthalene-1,4-dione (19)

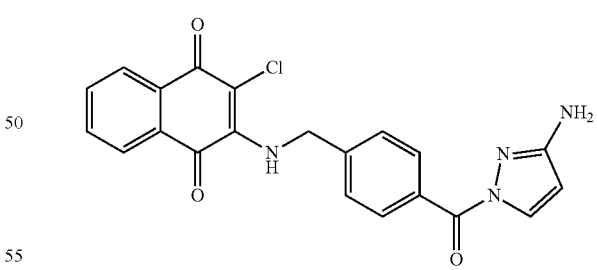

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-aminopyrazole (0.11 g, 1.32 mmol) at room temperature and the mixture was stirred overnight. The residue was filtered by suction filtration to yield a red product. The residue was filtered without further purification to afford 19 (0.17 g, 47.49%) as a red solid. $^1$H-NMR (300 MHz, DMSO-$d_6$): δ 5.03 (s, 2H), 5.64 (s, 2H), 5.99 (d, J=3.0 Hz, 1H), 7.42 (d, J=8.4 Hz, 2H), 7.71-7.77 (m, 1H), 7.79-7.85 (m, 1H), 7.92-7.98 (m, 4H), 8.11 (s, 1H), 8.15 (d, J=3.0 Hz, 1H).

Example 18 4-((3-chloro-1,4-dioxo-1,4-dihydronaphthalen-2-ylamino)methyl)-N-cyclopropylbenzamide (20)

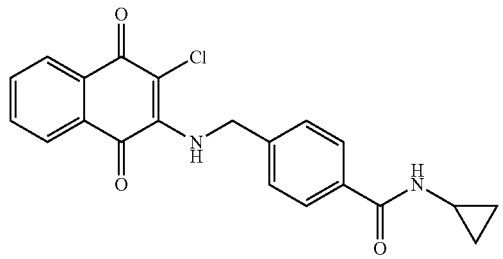 [SMILES: O=C(NC1CC1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added cyclopropylamine (0.09 ml, 1.32 mmol) at room temperature and the mixture was stirred overnight. The residue was filtered by suction filtration to yield a red product. The residue was filtered without further purification to afford 20 (0.12 g, 35.81%) as a red solid. $^1$H-NMR (300 MHz, DMSO-$d_6$): δ 0.52-0.55 (m, 2H), 0.63-0.69 (m, 2H), 2.77-2.83 (m, 1H), 4.98 (s, 2H), 7.34 (d, J=8.4 Hz, 2H), 7.72-7.75 (m, 3H), 7.82 (t, J=7.5 Hz, 1H), 7.96 (d, J=7.8 Hz, 2H), 8.05 (s, 1H), 8.36 (d, J=4.2 Hz, 1H).

Example 19 4-((3-chloro-1,4-dioxo-1,4-dihydronaphthalen-2-ylamino)methyl)-N-cyclopentylbenzamide (21)

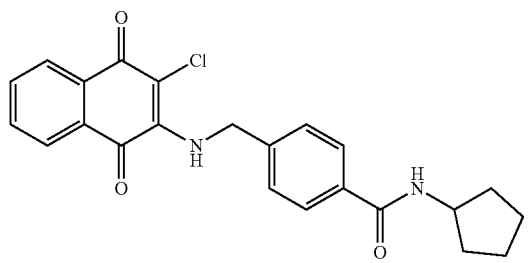 [SMILES: O=C(NC1CCCC1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added cyclopentylamine (0.13 ml, 1.32 mmol) at room temperature and the mixture was stirred overnight. The residue was filtered by suction filtration to yield a red product. The residue was filtered without further purification to afford 21 (0.25 g, 69.48%) as a red solid. $^1$H-NMR (300 MHz, DMSO-$d_6$): δ 1.50-1.56 (m, 4H), 1.66 (br, 2H), 1.80-1.89 (m, 2H), 4.15-4.22 (m, 1H), 4.98 (s, 2H), 7.35 (d, J=8.4 Hz, 2H), 7.71-7.84 (m, 4H), 7.96 (d, J=7.8, 2H), 8.06 (s, 1H), 8.19 (d, J=7.2 Hz, 1H).

Example 20 4-((3-chloro-1,4-dioxo-1,4-dihydronaphthalen-2-ylamino)methyl)-N-(1H-indazol-5-yl)benzamide (22)

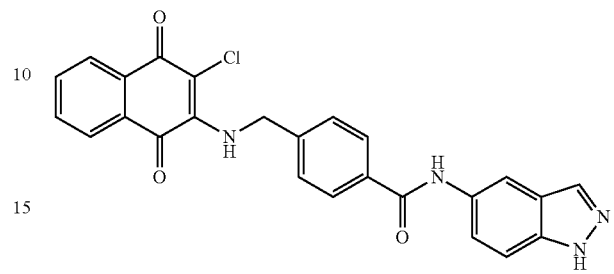

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 5-aminobenzindazole (0.18 g, 1.32 mmol) at room temperature and the mixture was stirred overnight. The residue was filtered by suction filtration to yield a red product. The residue was filtered without further purification to afford 22 (0.20 g, 49.74%) as a red solid. $^1$H-NMR (300 MHz, DMSO-$d_6$): δ 5.04 (d, J=7.2 Hz, 2H), 7.43-7.51 (m, 3H), 7.59-7.62 (m, 1H), 7.72-7.77 (m, 1H), 7.80-7.85 (m, 1H), 7.90-7.99 (m, 4H), 8.03 (s, 1H), 8.13 (t, J=7.2 Hz, 1H), 8.21 (s, 1H), 10.20 (s, 1H), 12.99 (s, 1H).

Example 21 4-((3-chloro-1,4-dioxo-1,4-dihydronaphthalen-2-ylamino)methyl)-N-(5-methylthiazol-2-yl)benzamide (23)

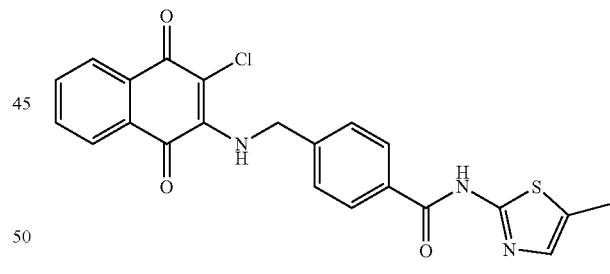

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-amino-5-methylthiazole (0.15 g, 1.32 mmol) at room temperature and the mixture was stirred overnight. The residue was filtered by suction filtration to yield a red product. The residue was filtered without further purification to afford 23 (0.38 g, 98.61%) as a red solid. $^1$H-NMR (300 MHz, DMSO-$d_6$): δ 2.36 (s, 3H), 5.03 (d, J=7.2 Hz, 2H), 7.20 (s, 1H), 7.45 (d, J=8.1 Hz, 2H), 7.72-7.78 (m, 1H), 7.80-7.85 (m, 1H), 7.50-7.99 (m, 2H), 8.03 (d, J=8.1 Hz, 2H), 8.10 (t, J=8.1 Hz, 1H), 12.21 (br, 1H).

Example 22 4-((3-chloro-1,4-dioxo-1,4-dihydronaphthalen-2-ylamino)methyl)-N-(5-methyl-3H-pyrazol-3-yl)benzamide (24)

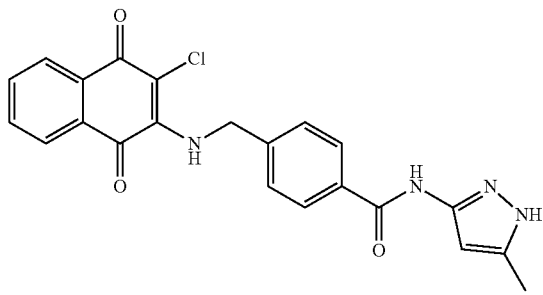 [SMILES: Cc1cc(NC(=O)c2ccc(CNC3=C(Cl)C(=O)c4ccccc4C3=O)cc2)n[nH]1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-amino-5-methylpyrazole (0.13 g, 1.32 mmol) at room temperature and the mixture was stirred overnight. The residue was purified by flash column over silica gel (ethyl acetate:n-hexane=1:9, Rf=0.20) to afford 24 (0.05 g, 13.50%) as a red solid. $^1$H-NMR (300 MHz, CDCl$_3$): δ 5.14 (d, J=6.3 Hz, 2H), 5.34 (s, 1H), 5.60 (br, 2H), 6.29 (br, 1H), 7.44 (d, J=8.4 Hz, 2H), 7.64-7.68 (m, 1H), 7.73-7.78 (m, 1H), 8.07 (d, J=7.8 Hz, 1H), 8.12 (d, J=8.4 Hz, 2H), 8.17 (d, J=6.3 Hz, 1H).

Example 23 2-(4-(3-amino-5-methyl-1H-pyrazole-1-carbonyl)benzylamino)-3-chloronaphthalene-1,4-dione (25)

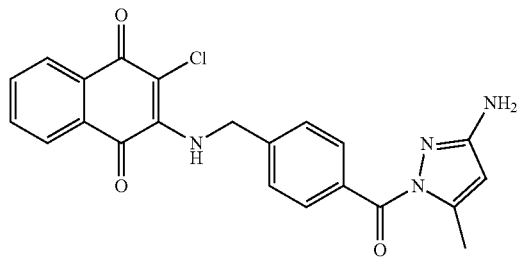 [SMILES: Cc1cc(N)nn1C(=O)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 mil) was stirred for a while, to which was then added 3-amino-5-methylpyrazole (0.13 g, 1.32 mmol) at room temperature and the mixture was stirred overnight. The residue was purified by flash column over silica gel (ethyl acetate:n-hexane=1:4, Rf=0.25) to afford 25 (0.04 g, 10.80%) as a red solid. $^1$H-NMR (300 MHz, DMSO-d$_6$): δ 2.49 (s, 3H), 5.03 (s, 2H), 5.44 (s, 2H), 5.78 (s, 1H), 7.38 (d, J=8.4 Hz, 2H), 7.73-7.86 (m, 4H), 7.98 (d, J=7.8 Hz, 2H), 8.10 (s, 1H).

Example 24 4-((3-chloro-1,4-dioxo-1,4-dihydronaphthalen-2-ylamino)methyl)-N-(3-nitropyridin-4-yl)benzamide (26)

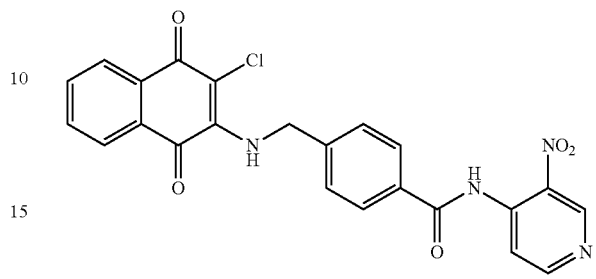

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-amino-3-nitropyridine (0.18 g, 1.32 mmol) at room temperature and the mixture was stirred overnight. The residue was purified by flash column over silica gel (ethyl acetate:n-hexane=1:2, Rf=0.25) to afford 26 (0.06 g, 14.73%) as a red solid. $^1$H-NMR (300 MHz, DMSO-d$_6$): δ 5.05 (d, J=6.9 Hz, 2H), 7.52 (d, J=8.4 Hz, 2H), 7.72-7.78 (m, 1H), 7.80-7.86 (m, 1H), 7.92 (d, J=8.4 Hz, 2H), 7.96-8.00 (m, 4H), 8.13 (t, J=6.9 Hz, 1H), 8.76 (d, J=5.7 Hz, 1H), 9.12 (s, 1H), 11.07 (s, 1H).

Example 26 4-((3-chloro-1,4-dioxo-1,4-dihydronaphthalen-2-ylamino)methyl)-N-(quinolin-6-yl)benzamide (28)

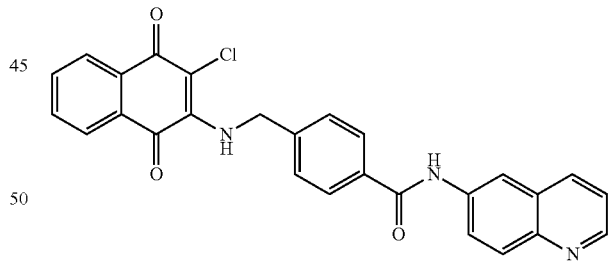

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 6-aminoquinoline (0.19 g, 1.32 mmol) at room temperature and the mixture was stirred overnight. The residue was purified by flash column over silica gel (ethyl acetate:n-hexane=1:2, Rf=0.20) to afford 28 (0.11 g, 26.72%) as a red solid. $^1$H-NMR (300 MHz, DMSO-d$_6$): δ 5.04 (s, 2H), 7.46-7.49 (m, 3H), 7.72-7.77 (m, 1H), 7.80-7.85 (m, 1H), 7.94-8.00 (m, 6H), 8.12 (br, 1H), 8.30 (d, J=8.7 Hz, 1H), 8.51 (s, 1H), 8.78-8.80 (m, 1H), 10.52 (s, 1H).

Example 27 4-((3-chloro-1,4-dioxo-1,4-dihydronaphthalen-2-ylamino)methyl)-N-(quinolin-8-yl)benzamide (29)

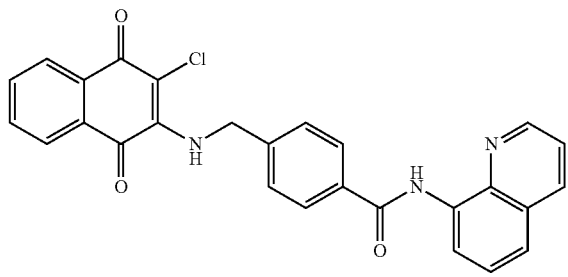 [SMILES: O=C(Nc1cccc2cccnc12)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 8-aminoquinoline (0.19 g, 1.32 mmol) at room temperature and the mixture was stirred overnight. The residue was filtered by suction filtration to yield a red product. The residue was filtered without further purification to afford 29 (0.15 g, 36.43%) as a red solid. $^1$H-NMR (300 MHz, DMSO-$d_6$): δ 5.07 (d, J=6.9 Hz, 2H), 7.55 (d, J=8.4 Hz, 2H), 7.62-7.69 (m, 2H), 7.72-7.78 (m, 2H), 7.81-7.84 (m, 1H), 7.86-8.02 (m, 4H), 8.14 (t, J=6.6 Hz, 1H), 8.44-8.47 (m, 1H), 8.70-8.73 (m, 1H), 8.94-8.95 (m, 1H), 10.62 (s, 1H).

Example 28 4-((3-chloro-1,4-dioxo-1,4-dihydronaphthalen-2-ylamino)methyl)-N-(quinolin-3-yl)benzamide (30)

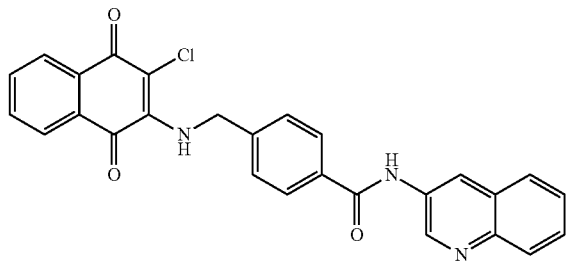 [SMILES: O=C(Nc1cnc2ccccc2c1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 3-aminoquinoline (0.19 g, 1.32 mmol) at room temperature and the mixture was stirred overnight. The residue was purified by flash column over silica gel (ethyl acetate:n-hexane=1:2, Rf=0.43) to afford 30 (0.10 g, 24.29%) as a red solid. $^1$H-NMR (300 MHz, DMSO-$d_6$): δ 5.05 (s, 2H), 7.49 (d, J=8.4 Hz, 2H), 7.55-7.60 (m, 1H), 7.63-7.68 (m, 1H), 7.72-7.85 (m, 2H), 7.93-7.99 (m, 6H), 8.11 (br, 1H), 8.82 (s, 1H), 9.12 (s, 1H), 10.66 (br, 1H).

Example 29 4-((3-chloro-1,4-dioxo-1,4-dihydronaphthalen-2-ylamino)methyl)-N-(quinolin-5-yl)benzamide (31)

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 5-aminoquinoline (0.13 g, 1.32 mmol) at room temperature and the mixture was stirred overnight. The residue was purified by flash column over silica gel (ethyl acetate:n-hexane=1:2, Rf=0.20) to afford 31 (0.10 g, 24.29%) as a red solid. $^1$H-NMR (300 MHz, DMSO-$d_6$): δ 5.06 (s, 2H), 7.47-7.53 (m, 3H), 7.68 (d, J=6.9 Hz, 1H), 7.73-7.83 (m, 3H), 7.92-8.05 (m, 5H), 8.14 (s, 1H), 8.37 (d, J=8.7 Hz, 1H), 8.91 (s, 1H), 10.48 (s, 1H).

Example 30 4-((3-chloro-1,4-dioxo-1,4-dihydronaphthalen-2-ylamino)methyl)-N-(2-methylquinolin-4-yl)benzamide (32)

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 2-aminothiazole (0.13 g, 1.32 mmol) at room temperature and the mixture was stirred overnight. The residue was purified by flash column over silica gel (ethyl acetate:n-hexane=1:1, Rf=0.13) to afford 32 (0.22 g, 51.87%) as a red solid. $^1$H-NMR (300 MHz, DMSO-$d_6$): δ 2.65 (s, 3H), 5.07 (d, J=6.9 Hz, 2H), 7.49-7.52 (m, 3H), 7.70-7.76 (m, 2H), 7.78-7.86 (m, 2H), 7.91-7.80 (m, 3H), 8.03 (d, J=8.4 Hz, 2H), 8.13-8.18 (m, 2H), 10.54 (s, 1H).

Example 31 4-((3-chloro-1,4-dioxo-1,4-dihydronaphthalen-2-ylamino)methyl)-N-(1H-indol-5-yl)benzamide (33)

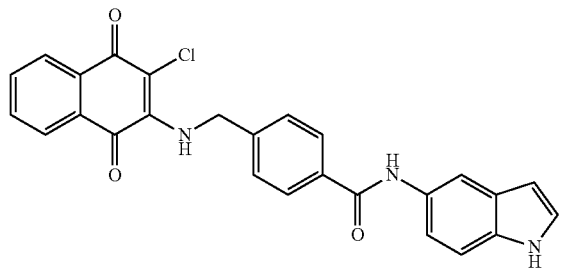 [SMILES: O=C(Nc1ccc2[nH]ccc2c1)c1ccc(CNC2=C(Cl)C(=O)c3ccccc3C2=O)cc1]

A mixture of 97 (0.26 g, 0.76 mmol), HBTU (0.43 g, 1.13 mmol), DIPEA (0.20 ml, 1.13 mmol) and DMF (2.5 ml) was stirred for a while, to which was then added 5-aminoindole (0.15 g, 1.13 mmol) at room temperature and the mixture was stirred overnight. The residue was purified by flash column over silica gel (ethyl acetate:n-hexane=2:3, Rf=0.35) to afford 33 (0.03 g, 8.66%) as a red solid. $^1$H-NMR (300 MHz, DMSO-d$_6$): δ 5.04 (d, J=6.6 Hz, 2H), 6.39 (s, 1H), 7.30-7.38 (m, 3H), 7.44 (d, J=8.1 Hz, 2H), 7.73-7.78 (m, 1H), 7.81-7.86 (m, 1H), 7.91 (d, J=8.4 Hz, 2H), 7.96-8.00 (m, 3H), 8.11 (s, 1H), 10.02 (s, 1H), 11.01 (s, 1H).

Example 32 4-((3-chloro-1,4-dioxo-1,4-dihydronaphthalen-2-ylamino)methyl)-N-(2-methyl-1H-indol-5-yl)benzamide (34)

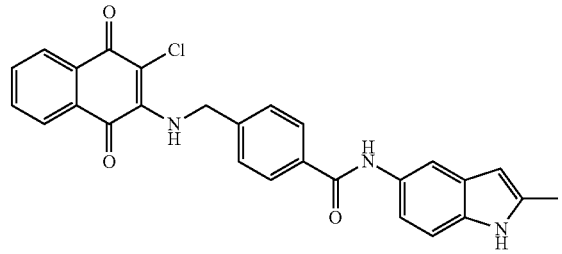 [SMILES: Cc1cc2cc(NC(=O)c3ccc(CNC4=C(Cl)C(=O)c5ccccc5C4=O)cc3)ccc2[nH]1]

A mixture of 97 (0.26 g, 0.76 mmol), HBTU (0.43 g, 1.13 mmol), DIPEA (0.20 ml, 1.13 mmol) and DMF (2.5 ml) was stirred for a while, to which was then added 5-amino2-methylindole (0.17 g, 1.13 mmol) at room temperature and the mixture was stirred overnight. The residue was purified by flash column over silica gel (ethyl acetate:n-hexane=1:1, Rf=0.13) to afford 34 (0.08 g, 22.40%) as a red solid. $^1$H-NMR (300 MHz, DMSO-d$_6$): δ 2.36 (s, 3H), 5.03 (s, 2H), 6.08 (s, 1H), 7.18-7.28 (m, 2H), 7.43 (d, J=8.4 Hz, 2H), 7.73-7.86 (m, 3H), 7.90 (d, J=8.1 Hz, 2H), 7.95-8.00 (m, 2H), 8.11 (br, 1H), 9.96 (s, 1H), 10.82 (s, 1H).

Example 33 4-((3-chloro-1,4-dioxo-1,4-dihydronaphthalen-2-ylamino)methyl)-N-(1H-indol-5-yl)benzamide (35)

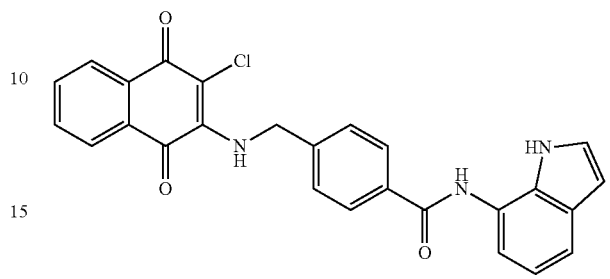

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 7-aminoindole (0.17 g, 1.32 mmol) at room temperature and the mixture was stirred overnight. The residue was purified by flash column over silica gel (ethyl acetate:n-hexane=1:1, Rf=0.13) to afford 35 (0.02 g, 4.99%) as a red solid. $^1$H-NMR (300 MHz, DMSO-d$_6$): δ 5.04 (s, 2H), 6.44 (s, 1H), 6.97 (t, J=7.8 Hz, 1H), 7.30-7.33 (m, 2H), 7.39 (d, J=−7.8 Hz, 1H), 7.46 (d, J=8.1 Hz, 2H), 7.72-7.78 (m, 1H), 7.80-7.86 (m, 1H), 7.86-7.99 (m, 4H), 8.12 (br, 1H), 10.05 (s, 1H), 10.86 (s, 1H).

Example 34 4-((3-chloro-1,4-dioxo-1,4-dihydronaphthalen-2-ylamino)methyl)-N-(1H-indol-4-yl)benzamide (36)

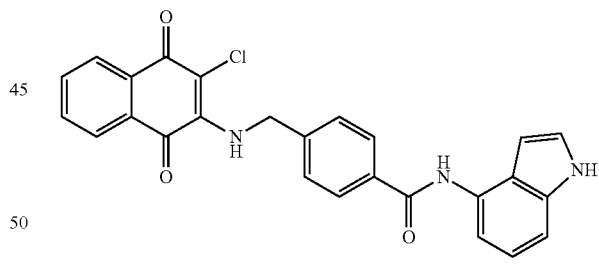

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-aminoindole (0.17 g, 1.32 mmol) at room temperature and the mixture was stirred overnight. The residue was purified by flash column over silica gel (ethyl acetate:n-hexane=1:1, Rf=0.45) to afford 36 (0.30 g, 74.78%) as a red solid. $^1$H-NMR (300 MHz, DMSO-d$_6$): δ 5.04 (s, 2H), 6.56 (s, 1H), 7.04 (t, J=7.8 Hz, 1H), 7.20 (d, J=1.5 Hz, 1H), 7.27 (t, J=3.0 Hz, 1H), 7.35 (d, J=7.2 Hz, 1H), 7.44 (d, J=8.4 Hz, 2H), 7.72-7.77 (m, 1H), 7.80-7.85 (m, 1H), 7.93-7.99 (m, 4H), 8.11 (br, 1H), 9.99 (s, 1H), 11.10 (s, 1H).

Example 35 4-((3-chloro-1,4-dioxo-1,4-dihydronaphthalen-2-ylamino)methyl)-N-(4-(4-ethylpiperazin-1-yl)phenyl)benzamide (37)

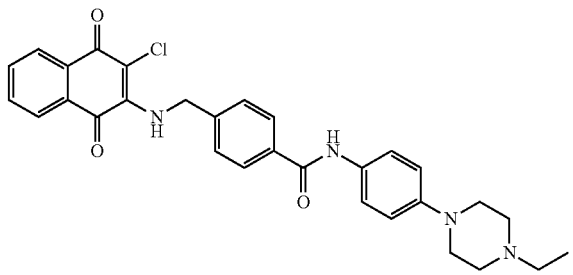 [SMILES: CCN1CCN(c2ccc(NC(=O)c3ccc(CNC4=C(Cl)C(=O)c5ccccc5C4=O)cc3)cc2)CC1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 4-(4-ethylpiperazin-1-yl)aniline (0.27 g, 1.32 mmol) at room temperature and the mixture was stirred overnight. The residue was filtered by suction filtration to yield a red product. The residue was filtered without further purification to afford 37 (0.40 g, 85.92%) as a red solid. $^1$H-NMR (300 MHz, DMSO-d$_6$): δ 1.01 (t, J=7.2 Hz, 3H), 2.34 (q, J=7.2 Hz, 2H), 3.07 (br, 4H), 5.01 (s, 2H), 6.89 (d, J=9.0 Hz, 2H), 7.41 (d, J=8.1 Hz, 2H), 7.56 (d, J=9.0 Hz, 2H), 7.74 (t, J=8.1 Hz, 1H), 7.77-7.88 (m, 3H), 7.95-7.98 (m, 2H), 8.09 (s, 1H), 9.98 (s, 1H).

Example 36 4-((3-chloro-1,4-dioxo-1,4-dihydronaphthalen-2-ylamino)methyl)-N-(1H-indazol-6-yl)benzamide (38)

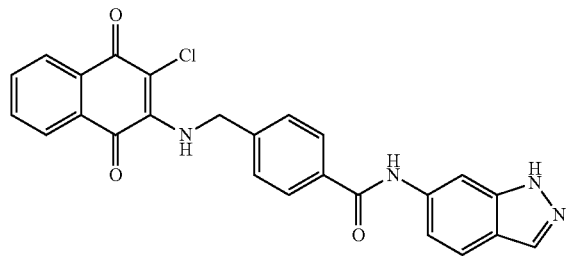 [SMILES: O=C(Nc1ccc2cn[nH]c2c1)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 6-aminoindazole (0.18 g, 1.32 mmol) at room temperature and the mixture was stirred overnight. The residue was filtered by suction filtration to yield a red product. The residue was filtered without further purification to afford 38 (0.13 g, 37.94%) as a red solid. $^1$H-NMR (300 MHz, DMSO-d$_6$): δ 5.05 (s, 2H), 7.36 (d, J=8.4 Hz, 1H), 7.46 (d, J=8.1 Hz, 2H), 7.68 (d, J=8.7 Hz, 1H), 7.75 (t, J=6.9 Hz, 1H), 7.83 (t, J=6.9 Hz, 1H), 7.92 (d, 1=8.1 Hz, 2H), 7.97-7.98 (m, 3H), 8.12 (br, 1H), 8.24 (s, 1H), 10.32 (s, 1H), 12.94 (s, 1H).

Example 37 4-((3-chloro-1,4-dioxo-1,4-dihydronaphthalen-2-ylamino)methyl)-N-(1H-pyrrolo[2,3-b]pyridin-5-yl)benzamide (39)

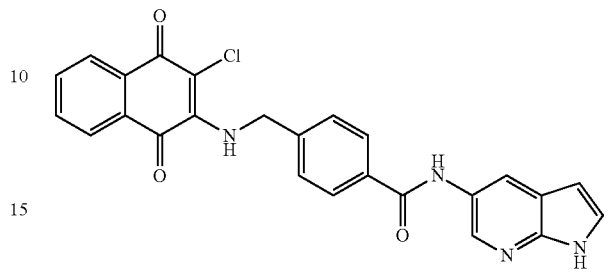

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 5-amino7-azaindole (0.18 g, 1.32 mmol) at room temperature and the mixture was stirred overnight. The residue was filtered by suction filtration to yield a red product. The residue was filtered without further purification to afford 39 (0.31 g, 77.10%) as a red solid. $^1$H-NMR (300 MHz, DMSO-d$_6$): δ 5.05 (d, J=7.2 Hz, 2H), 6.44 (s, 1H), 7.45-7.47 (m, 3H), 7.76 (t, J=8.1 Hz, 1H), 7.84 (t, J=7.8 Hz, 1H), 7.93-8.00 (m, 4H), 8.12 (br, 1H), 8.31 (s, 1H), 8.44 (s, 1H), 10.23 (s, 1H), 11.57 (s, 1H).

Example 38 4-((3-chloro-1,4-dioxo-1,4-dihydronaphthalen-2-ylamino)methyl)-N-(1H-pyrazolo[3,4-b]pyridin-5-yl)benzamide (40)

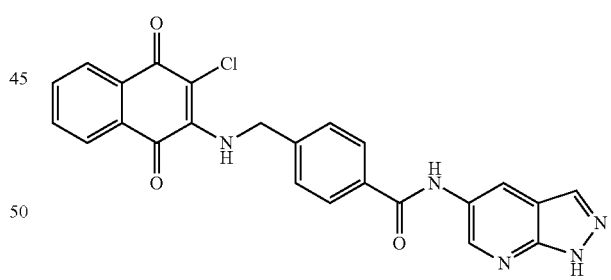

A mixture of 97 (0.28 g, 0.82 mmol), HBTU (0.47 g, 1.23 mmol), DIPEA (0.21 ml, 1.23 mmol) and DMF (2.5 ml) was stirred for a while, to which was then added 5-amino7-azaindazole (0.12 g, 0.90 mmol) at room temperature and the mixture was stirred overnight. The residue was purified by flash column over silica gel (ethyl acetate:n-hexane=2:1, Rf=0.18) to afford 40 (0.09 g, 23.97%) as a red solid. $^1$H-NMR (300 MHz, DMSO-d$_6$): δ 5.05 (s, 2H), 7.48 (d, J=8.4 Hz, 2H), 7.73-7.78 (m, 1H), 7.81-7.86 (m, 1H), 7.94-8.00 (m, 4H), 8.14 (s, 2H), 8.60 (d, J=2.4 Hz, 1H), 8.73 (d, J=2.1 Hz, 1H), 10.44 (s, 1H), 13.59 (br, 1H).

Example 39 4-((3-chloro-1,4-dioxo-1,4-dihydronaphthalen-2-ylamino)methyl)-N-(7-methyl-7H-pyrrolo[2,3-d]pyrimidin-4-yl)benzamide (41)

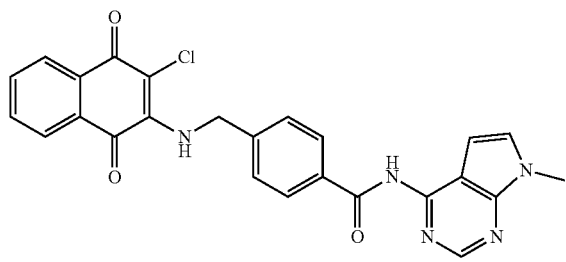 [SMILES: Cn1ccc2c(NC(=O)c3ccc(CNC4=C(Cl)C(=O)c5ccccc5C4=O)cc3)ncnc21]

A mixture of 97 (0.30 g, 0.88 mmol), HBTU (0.50 g, 1.32 mmol), DIPEA (0.23 ml, 1.32 mmol) and DMF (2.5 ml) was stirred for a while, to which was then added 6-amino-1-methyl-7-deazapurine (0.20 g, 1.32 mmol) at room temperature and the mixture was stirred overnight. The residue was purified by flash column over silica gel (ethyl acetate:n-hexane=2:1, Rf=0.45) to afford 41 (0.07 g, 16.86%) as a red solid. $^1$H-NMR (300 MHz, DMSO-$d_6$): δ 3.81 (s, 3H), 5.05 (d, J=7.2 Hz, 2H), 6.61 (d, J=3.6 Hz, 1H), 7.44-7.47 (m, 3H), 7.72-7.78 (m, 1H), 7.81-7.86 (m, 1H), 7.95-8.04 (m, 4H), 8.12 (t, J=7.5 Hz, 1H), 8.57 (s, 1H), 11.00 (s, 1H).

Example 40 4-((3-chloro-1,4-dioxo-1,4-dihydronaphthalen-2-ylamino)methyl)-N-(2,3-dihydro-1H-inden-4-yl)benzamide (42)

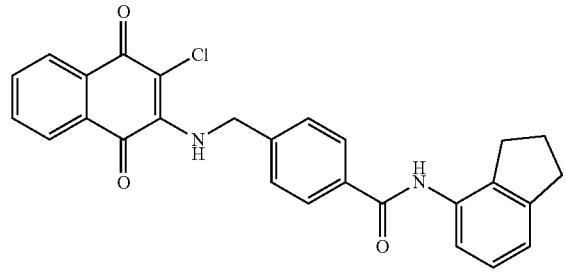 [SMILES: O=C(Nc1cccc2c1CCC2)c1ccc(CNC2=C(Cl)C(=O)c3ccccc3C2=O)cc1]

A mixture of 97 (0.30 g, 0.88 mmol), HBTU (0.50 g, 1.32 mmol), DIPEA (0.13 ml, 1.32 mmol) and DMF (2.5 ml) was stirred for a while, to which was then added 4-aminoindane (0.24 ml, 1.32 mmol) at room temperature and the mixture was stirred overnight. The residue was filtered by suction filtration to yield a red product. The residue was filtered without further purification to afford 42 (0.33 g, 82.07%) as a red solid. $^1$H-NMR (300 MHz, DMSO-$d_6$): δ 1.89-1.98 (m, 2H), 2.81 (t, J=7.5 Hz, 2H), 2.88 (t, J=7.5 Hz, 2H), 5.02 (d, J=7.2 Hz, 2H), 7.05-7.13 (m, 2H), 7.22 (d, J=7.5 Hz, 1H), 7.42 (d, J=8.1 Hz, 2H), 7.71-7.76 (m, 1H), 7.79-7.85 (m, 1H), 7.89 (d, J=8.4 Hz, 2H), 7.95-7.98 (m, 1H), 8.10 (t, J=7.5 Hz, 1H), 9.82 (s, 1H).

Example 48 4-(((3-bromo-1,4-dioxo-1,4-dihydronaphthalen-2-yl)amino)methyl)-N-(pyridin-2-yl)benzamide (6)

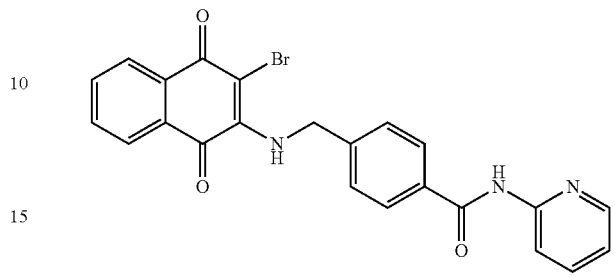

A mixture of 2,3-dibromo-1,4-naphthaquinone (0.31 g, 0.97 mmol), 4-(aminomethyl)-N-(pyridin-2-yl)benzamide (0.20 g, 0.88 mmol) and EtOH (10 ml) was stirred and refluxed overnight. The residue was purified by flash column over silica gel (ethyl acetate:n-hexane=1:2, Rf=0.20) to afford 6 (0.13 g, 31.95%) as a red solid. $^1$H-NMR (300 MHz, DMSO-$d_6$): δ 5.05 (d, J=7.2 Hz, 2H), 7.14 (m, 1H), 7.41 (d, J=8.1 Hz, 2H), 7.73 (t, J=7.5 Hz, 1H), 7.81 (m, 2H), 7.97 (m, 5H), 8.15 (d, J=8.1 Hz, 1H), 8.36 (d, J=4.8 Hz, 1H), 10.69 (s, 1H).

Example 49 tert-butyl 4-(pyrimidin-4-ylcarbamoyl)benzylcarbamate (100)

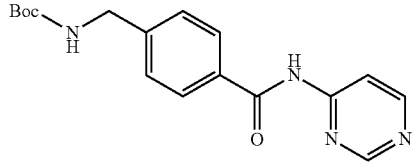 [SMILES: CC(C)(C)OC(=O)NCc1ccc(C(=O)Nc2ccncn2)cc1]

4-(aminomethyl)benzoic acid (5.0 g, 32.95 mmol) was added slowly to the corresponding sodium hydroxide (1.45 g, 36.25 mmole) and di-t-butyl-dicarbonate (7.95 g, 36.25 mmol) in $H_2O$ (62.5 ml) and THF (25 ml) at 0° C. The reaction mixture was warmed to room temperature, and stirring was continued for another 18 h. The solution was evaporated to give a residue. To the residue, DMF (0.36 mL), pyridine (18 mL), oxalyl chloride (6.24 ml) and toluene (144 ml) were added and the mixture was stirred at rt for 6 hrs. The solution was filtered, washed with toluene, and the filtrate evaporated to give a residue. To the residue, pyridine (112 mL), and 4-aminopyrimidine (3.74 g, 39.4 mmol) were added and the mixture was stirred at room temperature for 16 hrs. The solution was evaporated to give a residue, which was purified by flash column over silica gel (EtOAc:n-hexane=2:3) to afford 100 (3.03 g, 28.00%). $^1$H NMR (300 MHz, $CDCl_3$): δ 1.48 (s, 3H), 4.41 (d, J=6.0 Hz, 2H), 5.02 (brs, 1H), 7.45 (d, J=8.4 Hz, 2H), 7.91 (d, J=8.1 Hz, 2H), 8.33-8.36 (m, 1H), 8.69 (d, J=5.7 Hz, 1H), 8.72 (brs, 1H), 8.88 (s, 1H).

Example 50 tert-butyl 4-(pyrazin-2-ylcarbamoyl)benzylcarbamate (101)

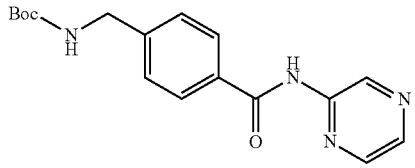 [SMILES: CC(C)(C)OC(=O)NCc1ccc(C(=O)Nc2cnccn2)cc1]

4-(aminomethyl)benzoic acid (5.0 g, 32.95 mmol) was added slowly to the corresponding sodium hydroxide (1.45 g, 36.25 mmol) and di-t-butyl-dicarbonate (7.95 g, 36.25 mmol) in H$_2$O (62.5 ml) and THF (25 mL) at 0° C. The reaction mixture was warmed to room temperature, and stirring was continued for another 18 h. The solution was evaporated to give a residue. To the residue, DMF (0.36 ml), pyridine (18 ml), oxalyl chloride (6.24 ml) and toluene (144 ml) were added and the mixture was stirred at room temperature for 6 hrs. The solution was filtered, washed with toluene, and the filtrate evaporated to give a residue. To the residue, pyridine (112 ml), and 2-aminopyrazine (3.74 g, 39.4 mmol) were added and the mixture was stirred at rt for 16 hrs. The residue was purified by flash column over silica gel (EtOAc:n-hexane=2:3) to afford 101 (3.90 g, 36.05%). $^1$H NMR (300 MHz, DMSO-d$_6$): δ 1.44 (s, 3H), 4.37 (d, J=5.4 Hz, 2H), 4.98 (brs, 1H), 7.41 (d, J=8.4 Hz, 2H), 7.88 (d, J=8.4 Hz, 2H), 8.23-8.25 (m, 1H), 8.34-8.36 (m, 1H), 8.54 (s, 1H), 9.67 (s, 1H).

Example 51 4-(((3-chloro-1,4-dioxo-1,4-dihydronaphthalen-2-yl)amino)methyl)-N-(pyrimidin-4-yl)benzamide (7)

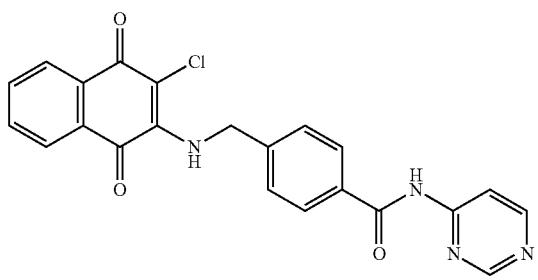 [SMILES: O=C(Nc1ccncn1)c1ccc(CNC2=C(Cl)C(=O)c3ccccc3C2=O)cc1]

A mixture of 2,3-dichloro-1,4-naphthoquinone (0.25 g, 1.10 mmol) and 100 (0.28 g, 1.23 mmol) and ethanol (10 ml) was refluxed for 16 h. The reaction mixture was filtered washed. The residue was filtered without further purification to afford 7 (0.08 g, 17.36%) as a red solid. $^1$H NMR (300 MHz, DMSO-d$_6$): δ 5.04 (d, J=6.6 Hz, 2H), 7.45 (d, J=8.1 Hz, 2H), 7.72-7.85 (m, 2H), 7.97-7.99 (m, 4H), 8.11 (m, 1H), 8.19 (d, J=4.5 Hz, 1H), 8.70 (d, J=5.4 Hz, 1H), 8.93 (s, 1H), 11.18 (s, 1H).

Example 52 4-(((3-chloro-1,4-dioxo-1,4-dihydronaphthalen-2-yl)amino)methyl)-N-(pyrazin-2-yl)benzamide (8)

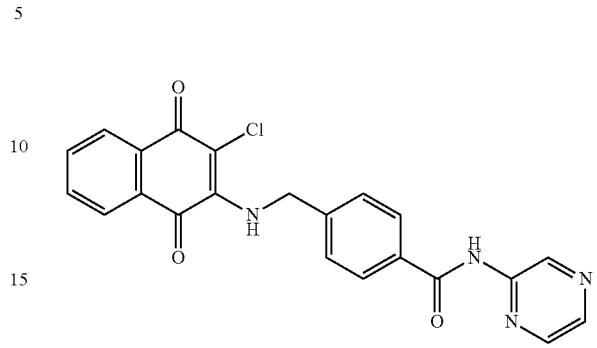

A mixture of 2,3-dichloro-1,4-naphthoquinone (1.19 g, 5.26 mmol) and 101 (1.5 g, 6.57 mmol) and ethanol (20 ml) was refluxed for 16 h. The reaction mixture was filtered and washed. The residue was filtered without further purification to afford 8 (0.48 g, 21.79%) as a red solid. $^1$H NMR (300 MHz, DMSO-d$_6$): δ 5.04 (d, J=7.2 Hz, 2H), 7.45 (d, J=8.4 Hz, 2H), 7.74-7.85 (m, 2H), 7.95-8.01 (m, 4H), 8.11 (t, J=6.9 Hz, 1H), 8.40 (d, J=2.4 Hz, 1H), 8.44-8.46 (m, 1H), 9.39 (d, J=1.5 Hz, 1H), 11.04 (s, 1H).

Example 53 4-amino-N-(pyridin-2-yl)benzamide (103)

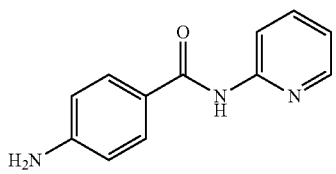

A mixture of 2-aminopyridine (0.50 g, 5.31 mmol), 4-nitrobenzoyl chloride (1.04 g, 5.58 mmol), pyridine (1 ml) and dichloromethane (5 ml) was stirred at room temperature overnight. The reaction was quenched with water and an extraction was conducted with dichloromethane (30 ml*3). The organic layer was collected and dried over anhydrous MgSO$_4$ and concentrated in vacuo to yield a yellow product. The residue was purified by flash column over silica gel (ethyl acetate:n-Hexane=2:1, Rf=0.75) to yield a pale yellow solid. Then the pale yellow solid was dissolved in MeOH (5 ml) and 10% Pd/C added as the catalyst at room temperature and the mixture was stirred under H$_2$ overnight. The 10% Pd/C was filtered via celite and the solvent removed from the filtrate to yield the oil product. The residue was filtered without further purification to afford 103 (0.70 g, 61.82%) as a yellow product. $^1$H-NMR (500 MHz, CDCl$_3$): δ 4.06 (s, 2H), 6.71 (d, J=8.5 Hz, 2H), 7.03 (m, 1H), 7.73 (m, 1H), 7.76 (d, J=8.5 Hz, 2H), 8.28 (d, J=4.0 Hz, 1H), 8.36 (d, J=8.5 Hz, 1H), 8.44 (br, 1H).

Example 54 4-amino-N-methyl-N-(pyridin-2-yl) benzamide (104)

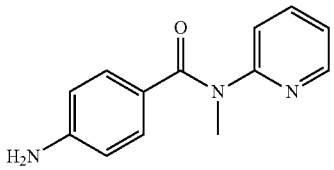 [SMILES: CN(C(=O)c1ccc(N)cc1)c1ccccn1]

A mixture of 2-aminopyridine (0.50 g, 5.31 mmol), 4-nitrobenzoyl chloride (1.04 g, 5.58 mmol), pyridine (1 ml) and dichloromethane (5 ml) was stirred at room temperature overnight. The reaction was quenched with water and an extraction was conducted with dichloromethane (30 ml*3). The organic layer was collected and dried over anhydrous MgSO$_4$ and concentrated in vacuo to yield a yellow product. The residue was purified by flash column over silica gel (ethyl acetate:n-Hexane=2:1, Rf=0.75) to yield a pale yellow solid. Then the pale yellow solid was dissolved in DMF (2 ml) and 60% NaH (0.07 g, 3.09 mmol) added at room temperature and the mixture was stirred for 10 min. Methyl iodide (0.26 ml, 4.12 mmol) was added and the mixture was stirred at room temperature overnight. Water was added to the residue to produce precipitant. The reaction was filtered to obtain the precipitant without further purification. The product was dissolved in IPA/H$_2$O (10 ml) and NH$_4$Cl (0.10 g, 1.86 mmol) and Fe powder (0.16 g, 2.79 mmol) were added and the mixture was stirred and refluxed for 1 h. The Fe powder was filtered via celite and the solvent removed from the filtrate to obtain the oil product. The residue was filtered without further purification to afford 104 (0.21 g, 44.07%) as a white product. $^1$H-NMR (500 MHz, CDCl$_3$): δ 3.83 (s, 3H), 3.89 (s, 2H), 6.41 (t, J=7.0 Hz, 1H), 6.66 (d, J=8.5 Hz, 2H), 7.44 (m, 1H), 7.45 (m, 1H), 8.12 (d, J=9.0 Hz, 2H), 8.25 (d, J=9.0 Hz, 1H).

Example 55 4-amino-N-ethyl-N-(pyridin-2-yl)benzamide (105)

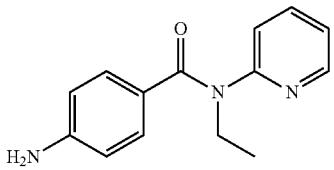 [SMILES: CCN(C(=O)c1ccc(N)cc1)c1ccccn1]

A mixture of 2-aminopyridine (0.50 g, 5.31 mmol), 4-nitrobenzoyl chloride (1.04 g, 5.58 mmol), pyridine (1 ml) and dichloromethane (5 ml) was stirred at room temperature overnight. The reaction was quenched with water and an extraction was conducted with dichloromethane (30 ml*3). The organic layer was collected and dried over anhydrous MgSO$_4$ and concentrated in vacuo to yield a yellow product. The residue was purified by flash column over silica gel (ethyl acetate:n-Hexane=2:1, Rf=0.75) to yield a pale yellow solid. Then the pale yellow solid was dissolved in DMF (2 ml) and 60% NaH (0.07 g, 3.09 mmol) added at room temperature and the mixture was stirred for 10 min. Ethyl iodide (0.33 ml, 4.12 mmol) was added and the mixture was stirred at room temperature overnight. Water was added to the residue to produce precipitant. The reaction was filtered to obtain the precipitant without further purification. The product was dissolved in MeOH (5 ml) and 10% Pd/C added as the catalyst and the mixture was stirred under H$_2$ overnight. The 10% Pd/C was filtered via celite and the solvent removed from the filtrate to obtain the oil product. The residue was purified by flash column over silica gel (dichloromethane:methanol=9:1, Rf=0.40) to afford 105 (0.21 g, 40.59%) as a yellow product. $^1$H-NMR (500 MHz, CDCl$_3$): δ 1.49 (t, J=7.5 Hz, 3H), 3.89 (s, 2H), 4.34 (q, J=7.5 Hz, 2H), 6.43 (m, 1H), 6.66 (d, J=8.5 Hz, 2H), 7.43 (m, 1H), 7.48 (m, 1H), 8.10 (d, J=8.5 Hz, 2H), 8.26 (d, J=9.0 Hz, 1H).

Example 56 4-((3-chloro-1,4-dioxo-1,4-dihydronaphthalen-2-yl)amino)-N-(pyridin-2-yl)benzamide (50)

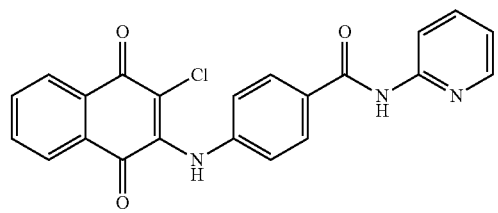 [SMILES: O=C(Nc1ccccn1)c1ccc(NC2=C(Cl)C(=O)c3ccccc3C2=O)cc1]

A mixture of 103 (0.30 g, 1.41 mmol) and 2,3-dichloro-1,4-naphthaquinone (0.35 g, 1.55 mmol) was dissolved in EtOH (20 ml) and the mixture was stirred and refluxed for 3 days. The residue was filtered by suction filtration to yield a red product. The residue was filtered without further purification to afford 50 (0.03 g, 5.27%) as a red solid. $^1$H-NMR (500 MHz, DMSO-d$_6$): δ 7.15 (m, 3H), 7.81 (t, J=8.0 Hz, 2H), 7.87 (t, J=8.0 Hz, 1H), 7.97 (d, J=8.5 Hz, 2H), 8.04 (d, J=7.5 Hz, 2H), 8.16 (d, J=8.5 Hz, 1H), 8.36 (d, J=4.5 Hz, 1H), 9.46 (s, 1H), 10.63 (s, 1H).

Example 57 4-((3-bromo-1,4-dioxo-1,4-dihydronaphthalen-2-yl)amino)-N-(pyridin-2-yl)benzamide (51)

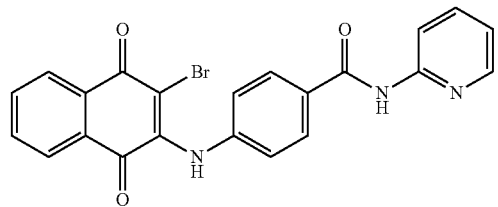 [SMILES: O=C(Nc1ccccn1)c1ccc(NC2=C(Br)C(=O)c3ccccc3C2=O)cc1]

A mixture of 103 (0.35 g, 1.64 mmol) and 2,3-dibromo-1,4-naphthaquinone (0.57 g, 1.80 mmol) was dissolved in EtOH (15 ml) and the mixture was stirred and refluxed for 4 days. The residue was filtered by suction filtration and washed by ethyl acetate to yield a red product. The residue was filtered without further purification to afford 51 (0.03 g, 4.08%) as a red solid. $^1$H-NMR (500 MHz, CDCl$_3$): δ 7.07-7.10 (m, 1H), 7.16 (d, J=8.5 Hz, 2H), 7.76 (m, 4H), 7.93 (d, J=8.0 Hz, 2H), 8.14 (d, J=7.5 Hz, 1H), 8.22 (d, J=7.5 Hz, 1H), 8.31 (d, J=4.5 Hz, 1H), 8.38 (d, J=8.5 Hz, 1H), 8.55 (br, 1H).

Example 58 4-((3-chloro-1,4-dioxo-1,4-dihydronaphthalen-2-yl)amino)-N-methyl-N-(pyridin-2-yl)benzamide (52)

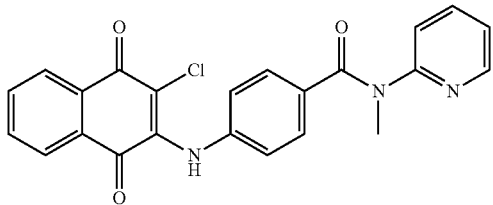 [SMILES: CN(C(=O)c1ccc(NC2=C(Cl)C(=O)c3ccccc3C2=O)cc1)c1ccccn1]

A mixture of 104 (0.24 g, 1.06 mmol) and 2,3-dichloro-1,4-naphthaquinone (0.27 g, 1.17 mmol) was dissolved in EtOH (15 ml) and the mixture was stirred and refluxed for 3 days. The residue was filtered by suction filtration to yield a red product. The residue was purified by flash column over silica gel (dichloromethane:methanol=9:1, Rf=0.50) to afford 52 (0.08 g, 18.06%) as a red solid. $^1$H-NMR (500 MHz, DMSO-d$_6$): δ 3.85 (s, 3H), 6.70 (m, 1H), 7.10 (d, J=8.5 Hz, 2H), 7.70 (m, 1H), 7.80 (t, J=7.5 Hz, 1H), 7.86 (m, 1H), 8.03 (d, J=8.0 Hz, 2H), 8.09 (d, J=8.5 Hz, 2H), 8.11 (m, 1H), 8.27 (d, J=9.0 Hz, 1H), 9.42 (s, 1H).

Example 59 4-((3-chloro-1,4-dioxo-1,4-dihydronaphthalen-2-yl)amino)-N-ethyl-N-(pyridin-2-yl)benzamide (53)

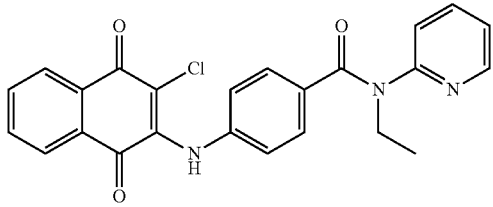 [SMILES: CCN(C(=O)c1ccc(NC2=C(Cl)C(=O)c3ccccc3C2=O)cc1)c1ccccn1]

A mixture of 105 (0.25 g, 0.92 mmol) and 2,3-dichloro-1,4-naphthaquinone (0.23 g, 1.01 mmol) was dissolved in EtOH (15 ml) and the mixture was stirred and refluxed for 4 days. The residue was filtered by suction filtration to yield a red product. The residue was filtered without further purification to afford 53 (0.18 g, 45.30%) as a red solid. $^1$H-NMR (500 MHz, CDCl$_3$): δ 1.53 (m, 3H), 4.41 (d, J=6.5 Hz, 2H), 6.55 (s, 1H), 7.08 (d, J=8.5 Hz, 2H), 7.57 (m, 2H), 7.70 (m, 1H), 7.77 (m, 2H), 8.13 (d, J=7.5 Hz, 1H), 8.20 (d, J=9.0 Hz, 1H), 8.27 (d, J=7.5 Hz, 2H), 8.38 (d, J=9.0 Hz, 1H).

Example 60 4-((3-isopropyl-1,4-dioxo-1,4-dihydronaphthalen-2-yl)amino)-N-(pyridin-2-yl)benzamide (56)

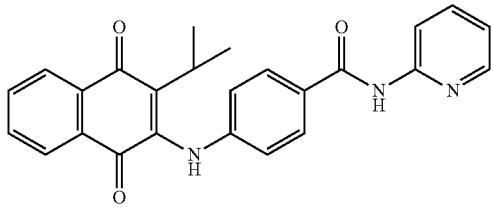 [SMILES: CC(C)C1=C(Nc2ccc(C(=O)Nc3ccccn3)cc2)C(=O)c2ccccc2C1=O]

A mixture of 51 (0.29 g, 0.86 mmol) was dissolved in EtOH (3.3 ml) and toluene (6.5 ml) and added Pd(PPh$_3$)$_4$ (0.08 g, 0.07 mmol), 2M K$_2$CO$_3$(aq.) (1 ml) and isopropylboronic acid (0.07 g, 0.78 mmol). The reaction was filtered via celite and the solvent removed from the filtrate to yield the oil product. The residue was purified by flash column over silica gel (ethyl acetate:n-Hexane=1:2, Rf=0.33) to afford 56 (0.03 g, 11.22%) as a red product. $^1$H-NMR (300 MHz, CDCl$_3$): δ 1.29 (d, J=6.6 Hz, 6H), 2.69 (qui, J=6.9 Hz, 1H), 7.09 (m, 3H), 7.22 (s, 1H), 7.67 (m, 1H), 7.75 (m, 2H), 7.91 (d, J=8.7 Hz, 2H), 8.09 (m, 2H), 8.31 (m, 1H), 8.37 (m, 1H), 8.54 (s, 1H).

Example 61 4-amino-N-(pyrazin-2-yl)benzamide (108)

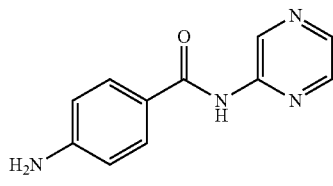 [SMILES: Nc1ccc(C(=O)Nc2cnccn2)cc1]

A mixture of 2-aminopyrazine (0.50 g, 5.26 mmol), 4-nitrobenzoyl chloride (1.02 g, 5.52 mmol), pyridine (1 ml) and dichloromethane (5 ml) was stirred at room temperature overnight. Water was added to produce the precipitant to yield a yellow product. The product was dissolved in IPA/H$_2$O (10 ml) and NH$_4$Cl (0.78 g, 14.61 mmol) and Fe powder (0.54 g, 9.74 mmol) were added and the mixture was stirred and refluxed for 1 h. The Fe powder was filtered via celite and the solvent removed from the filtrate to yield the oil product. The residue was filtered without further purification to afford 108 (0.37 g, 33.14%) as a white product. $^1$H-NMR (500 MHz, CD$_3$O=OD+CDCl$_3$): δ 6.60 (d, J=8.5 Hz, 2H), 7.66 (d, J=8.5 Hz, 2H), 8.18 (s, 2H), 9.49 (s, 1H).

Example 62 4-amino-N-(pyrimidin-2-yl)benzamide (109)

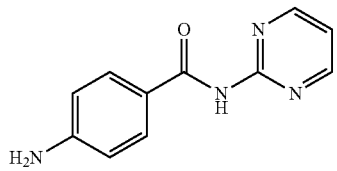 [SMILES: Nc1ccc(C(=O)Nc2ncccn2)cc1]

A mixture of 2-aminopyrimidine (0.50 g, 5.26 mmol), 4-nitrobenzoyl chloride (1.02 g, 5.52 mmol), pyridine (1 ml) and dichloromethane (5 ml) was stirred at room temperature overnight. Water was added to produce the precipitant to yield a yellow product. The product was dissolved in IPA/H$_2$O (10 ml) and NH$_4$Cl (0.78 g, 14.61 mmol) and Fe powder (0.54 g, 9.74 mmol) were added and the mixture was stirred and refluxed for 1 h. The Fe powder was filtered via celite and the solvent removed from the filtrate to yield the oil product. The residue was filtered without further purification to afford 109 (1.04 g, 50.88%) as a white product. $^1$H-NMR (500 MHz, CD$_3$OD+CDCl$_3$): δ 6.58 (d, J=8.5 Hz, 2H), 6.95 (t, J=4.5 Hz, 1H), 7.66 (d, J=8.5 Hz, 2H), 8.50 (d, J=5.0 Hz, 2H).

Example 63 4-((3-chloro-1,4-dioxo-1,4-dihydronaphthalen-2-yl)amino)-N-(pyrazin-2-yl)benzamide (54)

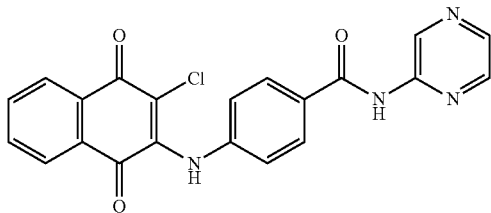 [SMILES: O=C(Nc1cnccn1)c1ccc(NC2=C(Cl)C(=O)c3ccccc3C2=O)cc1]

A mixture of 108 (0.15 g, 0.70 mmol) and 2,3-dichloro-1,4-naphthaquinone (0.17 g, 0.77 mmol) was dissolved in EtOH (15 ml). The reaction was stirred and refluxed overnight. The residue was filtered by suction filtration and washed by ethyl acetate, dichloromethane and methanol to yield a red product. The residue was filtered without further purification to afford 54 (0.16 g, 56.46%) as a red solid. $^1$H-NMR (300 MHz, DMSO-$d_6$): δ 7.19 (d, J=8.7 Hz, 2H), 7.86 (m, 2H), 8.01 (d, J=9.0 Hz, 2H), 8.06 (m, 2H), 8.43 (m, 2H), 9.41 (s, 1H), 9.53 (s, 1H), 11.01 (s, 1H).

Example 64 4-((3-chloro-1,4-dioxo-1,4-dihydronaphthalen-2-yl)amino)-N-(pyrimidin-2-yl)benzamide (55)

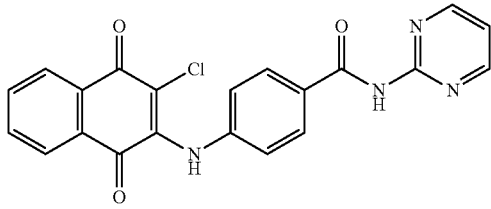 [SMILES: O=C(Nc1ncccn1)c1ccc(NC2=C(Cl)C(=O)c3ccccc3C2=O)cc1]

A mixture of 109 (0.30 g, 1.40 mmol) and 2,3-dichloro-1,4-naphthaquinone (0.35 g, 1.54 mmol) was dissolved in EtOH (15 ml) and the mixture was stirred and refluxed for 3 days. The residue was purified by flash column over silica gel (dichloromethane:methanol=9:1, Rf=0.55) to afford 55 (0.14 g, 24.70%) as a red solid. $^1$H-NMR (300 MHz, DMSO-$d_6$): δ 7.17 (d, J=7.8 Hz, 2H), 7.84 (m, 2H), 8.03 (m, 4H), 8.39 (d, J=2.4 Hz, 1H), 8.46 (m, 1H), 9.40 (d, J=1.5 Hz, 1H), 9.52 (br, 1H), 10.98 (s, 1H).

Example 65 3-amino-N-(pyridin-2-yl)benzamide (110)

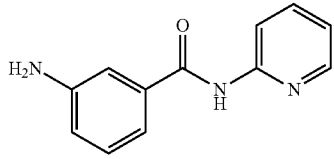 [SMILES: Nc1cccc(C(=O)Nc2ccccn2)c1]

A mixture of 2-aminopyridine (0.50 g, 5.31 mmol), 3-nitrobenzoyl chloride (1.04 g, 5.58 mmol), pyridine (1 ml) and dichloromethane (5 ml) was stirred at room temperature overnight. The reaction was quenched with water and an extraction was conducted with ethyl acetate (30 ml*3). The organic layer was collected and dried over anhydrous MgSO$_4$ and concentrated in vacuo to yield a yellow product. The residue was purified by flash column over silica gel (ethyl acetate:n-Hexane=2:1, Rf=0.60) to yield a pale yellow solid. Then the pale yellow solid was dissolved in MeOH (5 ml) and 10% Pd/C added as the catalyst at room temperature and the mixture was stirred under H$_2$ overnight. The 10% Pd/C was filtered via celite and the solvent removed from the filtrate to yield the oil product. The residue was purified by flash column over silica gel (ethyl acetate:n-Hexane=2:1, Rf=0.38) to afford 110 (0.25 g, 83.31%) as a white product. $^1$H-NMR (500 MHz, CDCl$_3$): δ 3.85 (s, 2H), 6.86 (d, J=8.5 Hz, 1H), 7.07 (m, 1H), 7.25 (m, 3H), 7.75 (m, 1H), 8.30 (d, J=4.5 Hz, 1H), 8.37 (d, J=8.5 Hz, 1H), 8.53 (br, 1H).

Example 66 3-amino-N-(pyrimidin-2-yl)benzamide (111)

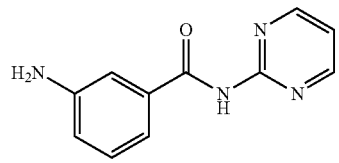 [SMILES: Nc1cccc(C(=O)Nc2ncccn2)c1]

A mixture of 2-aminopyrimidine (0.50 g, 5.26 mmol), 3-nitrobenzoyl chloride (1.02 g, 5.52 mmol), pyridine (1 ml) and dichloromethane (5 ml) was stirred at room temperature overnight. The reaction was quenched with water and an extraction was conducted with dichloromethane (30 ml*3). The organic layer was collected and dried over anhydrous MgSO$_4$ and concentrated in vacuo to yield a yellow product. The residue was purified by flash column over silica gel (dichloromethane:methanol=9:1, Rf=0.48) to yield a pale yellow solid. The product was dissolved in IPA/H$_2$O (10 ml) and NH$_4$Cl (0.54 g, 10.08 mmol) and Fe powder (0.84 g, 15.12 mmol) were added and the mixture was stirred and refluxed for 1 h. The Fe powder was filtered via celite and the solvent removed from the filtrate to yield the oil product. The residue was filtered without further purification to afford 111 (0.99 g, 87.64%) as a white product. $^1$H-NMR (300 MHz, CDCl$_3$): δ 3.89 (s, 2H), 6.86 (m, 1H), 7.05 (t, J=4.8 Hz, 1H), 7.27 (m, 3H), 8.66 (d, J=5.1 Hz, 3H).

Example 67 3-amino-N-(pyrazin-2-yl)benzamide (112)

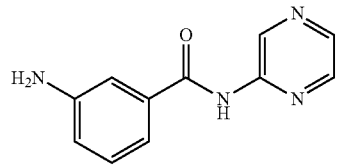 [SMILES: Nc1cccc(C(=O)Nc2cnccn2)c1]

A mixture of 2-aminopyrazine (0.50 g, 5.26 mmol), 3-nitrobenzoyl chloride (1.02 g, 5.52 mmol), pyridine (1 ml) and dichloromethane (5 ml) was stirred at room temperature overnight. Water was added to produce the precipitant. The residue was filtered without further purification to yield a pale yellow solid. The product was dissolved in IPA/H$_2$O (10 ml) and NH$_4$Cl (0.53 g, 9.82 mmol) and Fe powder (0.82 g, 14.73 mmol) were added and the mixture was stirred and refluxed for 1 h. The Fe powder was filtered via celite and the solvent removed from the filtrate to yield the oil product. The residue was filtered without further purification to afford 112 (1.02 g, 90.63%) as a white product. $^1$H-NMR (300 MHz, CDCl$_3$): δ 3.88 (s, 2H), 6.88 (m, 1H), 7.25 (m, 3H), 8.26 (q, J=1.5 Hz, 1H), 8.37 (d, J=2.4 Hz, 1H), 8.48 (s, 1H), 9.70 (d, J=1.5 Hz, 1H).

Example 68 3-((3-chloro-1,4-dioxo-1,4-dihydronaphthalen-2-yl)amino)-N-(pyridin-2-yl)benzamide (57)

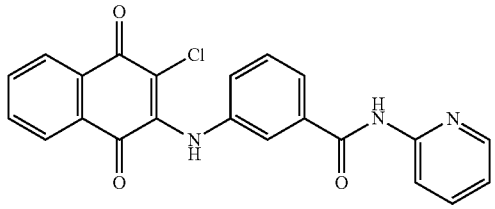 [SMILES: O=C(Nc1ccccn1)c1cccc(NC2=C(Cl)C(=O)c3ccccc3C2=O)c1]

A mixture of 110 (0.59 g, 2.77 mmol) and 2,3-dichloro-1,4-naphthaquinone (0.69 g, 3.05 mmol) was dissolved in EtOH (15 ml) and the mixture was stirred and refluxed for 2 days. The residue was filtered by suction filtration to yield a red product. The residue was filtered without further purification to afford 57 (0.67 g, 59.90%) as a red solid. $^1$H-NMR (500 MHz, CDCl$_3$+DMSO-d$_6$): δ 6.93 (m, 2H), 7.07 (t, J=8.0 Hz, 1H), 7.32 (t, J=7.5 Hz, 1H), 7.38 (t, J=7.5 Hz, 1H), 7.46 (s, 1H), 7.60 (d, J=8.0 Hz, 1H), 7.70 (m, 3H), 8.00 (d, J=5.0 Hz, 1H), 8.03 (d, J=9.0 Hz, 1H), 8.45 (s, 1H).

Example 69 3-((3-chloro-1,4-dioxo-1,4-dihydronaphthalen-2-yl)amino)-N-(pyrimidin-2-yl)benzamide (58)

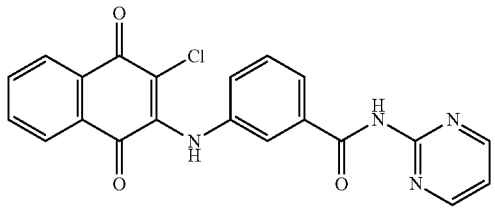 [SMILES: O=C(Nc1ncccn1)c1cccc(NC2=C(Cl)C(=O)c3ccccc3C2=O)c1]

A mixture of 111 (0.35 g, 1.63 mmol) and 2,3-dichloro-1,4-naphthaquinone (0.41 g, 1.79 mmol) was dissolved in EtOH (15 ml) and the mixture was stirred and refluxed for 3 days. The residue was purified by flash column over silica gel (dichloromethane:methanol=9:1, Rf=0.48) to afford 58 (0.04 g, 7.06%) as a red solid. $^1$H-NMR (300 MHz, DMSO-d$_6$): δ 7.24 (t, J=4.8 Hz, 1H), 7.35 (m, 1H), 7.44 (t, J=8.1 Hz, 1H), 7.72 (m, 2H), 7.84 (m, 2H), 8.04 (m, 2H), 8.71 (d, J=4.8 Hz, 2H), 9.42 (s, 1H), 10.90 (s, 1H).

Example 70 3-((3-chloro-1,4-dioxo-1,4-dihydronaphthalen-2-yl)amino)-N-(pyrazin-2-yl)benzamide (59)

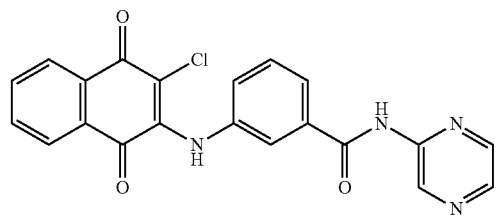 [SMILES: O=C(Nc1cnccn1)c1cccc(NC2=C(Cl)C(=O)c3ccccc3C2=O)c1]

A mixture of 112 (0.25 g, 1.17 mmol) and 2,3-dichloro-1,4-naphthaquinone (0.29 g, 1.29 mmol) was dissolved in EtOH (15 ml) and the mixture was stirred and refluxed overnight. The residue was filtered by suction filtration and without further purification to afford 59 (0.24 g, 50.67%) as a red solid. $^1$H-NMR (300 MHz, DMSO-d$_6$): δ 7.37 (m, 1H), 7.46 (t, J=7.8 Hz, 1H), 7.80 (m, 3H), 7.87 (m, 1H), 8.04 (m, 2H), 8.40 (d, J=2.7 Hz, 1H), 8.45 (m, 1H), 9.39 (d, J=1.5 Hz, 1H), 10.99 (s, 1H).

Example 71 N-(4-aminophenyl)picolinamide (115)

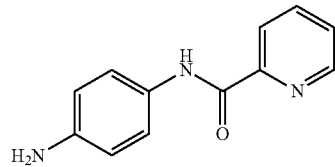 [SMILES: Nc1ccc(NC(=O)c2ccccn2)cc1]

A mixture of picolinic acid (0.50 g, 4.06 mmol), thionyl chloride (0.88 ml, 12.18 mmol), and dichloromethane (5 ml) was stirred and refluxed for 3 h. Then the reaction was added 4-nitroaniline (0.56 g, 4.06 mmol) dissolved in CH$_2$Cl$_2$ (5 ml) and the mixture was stirred and refluxed overnight. The reaction was quenched with water and an extraction was conducted with ethyl acetate (30 ml*3). The organic layer was collected and dried over anhydrous MgSO$_4$ and concentrated in vacuo to yield a yellow product. The residue was purified by flash column over silica gel (ethyl acetate: n-Hexane=1:2, Rf=0.40) to yield a pale yellow solid. Then the pale yellow solid was dissolved in MeOH (5 ml) and 10% Pd/C added as the catalyst at room temperature and the mixture was stirred under H$_2$ overnight. The 10% Pd/C was filtered via celite and the solvent removed from the filtrate to yield the yellow product. The residue was filtered without further purification to afford 115 (0.36 g, 41.64%) as a yellow solid. $^1$H-NMR (500 MHz, CD$_3$OD): δ 6.75 (m, 2H), 7.48 (m, 2H), 7.55 (m, 1H), 7.97 (m, 1H), 8.16 (d, J=2.0 Hz, 1H).

Example 72 N-(4-aminophenyl)isonicotinamide (116)

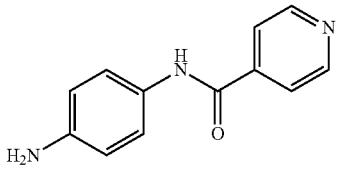 [SMILES: Nc1ccc(NC(=O)c2ccncc2)cc1]

A mixture of isonicotinoyl chloride (0.50 g, 2.81 mmol), cesium carbonate (1.83 g, 5.62 mmol), acetonitrile (10 ml) was stirred and refluxed overnight. Then 4-nitroaniline (0.19 g, 1.41 mmol) was added, and the mixture was stirred at room temperature overnight. The reaction was quenched with water and an extraction was conducted with ethyl acetate (30 ml*3). The organic layer was collected and dried over anhydrous $MgSO_4$ and concentrated in vacuo to yield a yellow product. The residue was purified by flash column over silica gel (ethyl acetate:n-Hexane=3:1, Rf=0.25) to yield a pale yellow solid. Then the pale yellow solid was dissolved in MeOH (5 ml) and 10% Pd/C added as the catalyst at room temperature and the mixture was stirred under $H_2$ overnight. The 10% Pd/C was filtered via celite and the solvent removed from the filtrate to yield the yellow product. The residue was filtered without further purification to afford 116 (0.10 g, 35.29%) as a yellow solid. $^1$H-NMR (500 MHz, $CD_3OD$): δ 6.74 (d, J=9.0 Hz, 2H), 7.39 (d, J=8.5 Hz, 2H), 7.85 (d, J=6.0 Hz, 2H), 8.70 (d, J=6.0 Hz, 2H).

Example 73 N-(4-((3-chloro-1,4-dioxo-1,4-dihydronaphthalen-2-yl)amino)phenyl)picolinamide (60)

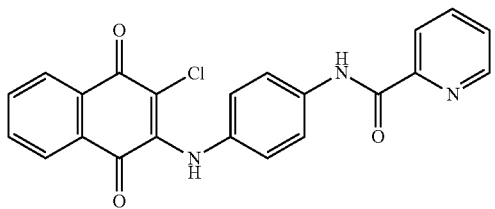 [SMILES: O=C(Nc1ccc(NC2=C(Cl)C(=O)c3ccccc3C2=O)cc1)c1ccccn1]

A mixture of 110 (0.10 g, 0.47 mmol) and 2,3-dichloro-1,4-naphthaquinone (0.11 g, 0.49 mmol) was dissolved in EtOH (2 ml) under microwave at 150° C. for 2 min. The residue was purified by flash column over silica gel (ethyl acetate:n-Hexane=1:1, Rf=0.50) to afford 60 (0.01 g, 3.54%) as a red solid. $^1$H-NMR (500 MHz, DMSO-$d_6$): δ 7.13 (d, J=8.5 Hz, 2H), 7.67 (m, 1H), 7.79 (m, 1H), 7.86 (m, 3H), 8.03 (m, 2H), 8.06 (m, 1H), 8.15 (d, J=7.5 Hz, 1H), 8.74 (d, J=4.5 Hz, 1H), 9.29 (s, 1H), 10.65 (s, 1H).

Example 74 N-(4-((3-chloro-1,4-dioxo-1,4-dihydronaphthalen-2-yl)amino)phenyl)isonicotinamide (61)

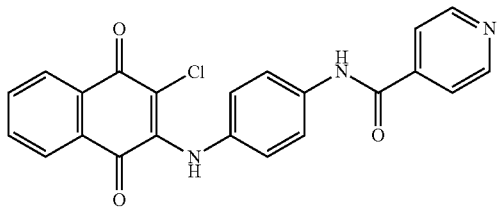 [SMILES: O=C(Nc1ccc(NC2=C(Cl)C(=O)c3ccccc3C2=O)cc1)c1ccncc1]

A mixture of 116 (0.10 g, 0.47 mmol) and 2,3-dichloro-1,4-naphthaquinone (0.11 g, 0.49 mmol) was dissolved in EtOH (2 ml) under microwave at 150° C. for 2 min. The residue was purified by flash column over silica gel (ethyl acetate:n-Hexane=3:1, Rf=0.25) to afford 61 (0.01 g, 5.27%) as a red solid. $^1$H-NMR (500 MHz, DMSO-$d_6$): δ 7.14 (d, J=8.5 Hz, 2H), 7.71 (d, J=9.0 Hz, 2H), 7.80 (t, J=8.0 Hz, 1H), 7.87 (m, 3H), 8.03 (m, 2H), 8.78 (d, J=5.5 Hz, 2H), 9.32 (s, 1H), 10.50 (s, 1H).

Example 75 1-((4-nitrophenyl)sulfonyl)-1H-indole (119)

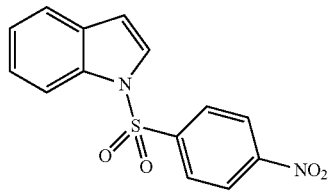 [SMILES: O=[N+]([O-])c1ccc(S(=O)(=O)n2ccc3ccccc32)cc1]

A mixture of indole (0.75 g, 6.40 mmol) was dissolved in DMF (3 ml) and added NaH (0.38 g, 9.60 mmol) and 4-nitrobenzenesulfonyl chloride (2.13 g, 9.60 mmol) and the mixture was stirred at room temperature overnight. Water was added to produce the precipitant. The residue was filtered by suction filtration without further purification to yield a white product to afford 119 (0.78 g, 40.31%) as a yellow product. $^1$H-NMR (300 MHz, $CDCl_3$): δ 6.72 (d, J=2.7 Hz, 1H), 7.31 (m, 2H), 7.55 (m, 2H), 8.00 (m, 3H), 8.25 (d, J=2.4 Hz, 2H).

Example 76 4-((1H-pyrrolo[2,3-b]pyridin-1-yl)sulfonyl)aniline (120)

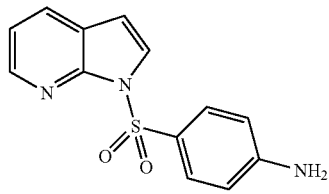 [SMILES: Nc1ccc(S(=O)(=O)n2ccc3cccnc32)cc1]

A mixture of 7-azaindole (1.00 g, 8.46 mmol) was dissolved in DMF (3 ml) and added NaH (0.51 g, 12.69 mmol) and added 4-nitrobenzenesulfonyl chloride (2.81 g, 12.69 mmol) and the mixture was stirred at room temperature overnight. Water was added to produce the precipitant. The residue was filtered by suction filtration to yield a white product. The product was dissolved in IPA/$H_2O$ (70 ml) and $NH_4Cl$ (0.75 g, 14.16 mmol) and Fe powder (1.18 g, 21.24 mmol) were added and the mixture was stirred and refluxed for 1 h. The reaction was filtered to remove Fe powder via celite and the residue was purified by flash column over silica gel (ethyl acetate:n-Hexane=1:4, Rf=0.08) to afford 120 (1.13 g, 48.83%) as a yellow product. $^1$H-NMR (300 MHz, $CDCl_3$): δ 4.15 (s, 2H), 6.54 (d, J=3.9 Hz, 1H), 6.60 (d, J=8.7 Hz, 2H), 7.15 (m, 1H), 7.17 (d, J=3.9 Hz, 1H), 7.82 (m, 1H), 7.96 (d, J=8.7 Hz, 2H), 8.41 (m, 1H).

Example 77 2-((4-((1H-indol-1-yl)sulfonyl)phenyl)amino)-3-chloronaphthalene-1,4-dione (62)

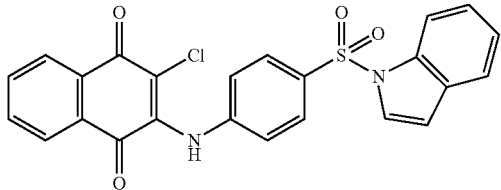 [SMILES: O=C1C(Cl)=C(Nc2ccc(S(=O)(=O)n3ccc4ccccc43)cc2)C(=O)c2ccccc21]

A mixture of 119 was dissolved in IPA/H$_2$O (30 ml) and NH$_4$Cl (0.32 g, 5.96 mmol) and Fe powder (0.50 g, 8.94 mmol) were added and the mixture was stirred and refluxed for 1 h. The reaction was filtered to remove Fe powder via celite and the residue was purified by flash column over silica gel (ethyl acetate:n-Hexane=1:4, Rf=0.08) to yield a yellow product. Then the residue was dissolved in EtOH (15 ml) and added 2,3-dichloro-1,4-naphthaquinone (0.70 g, 3.07 mmol) and the mixture was stirred and refluxed for 3 days. The residue was filtered by suction filtration to yield a red product. The residue was purified by flash column over silica gel (ethyl acetate:n-Hexane=1:4, Rf=0.18) to afford 62 (0.20 g, 15.49%) as a red solid. $^1$H-NMR (300 MHz, CDCl$_3$): δ 6.67 (m, 1H), 6.97 (d, J=8.7 Hz, 2H), 7.24 (m, 1H), 7.31 (m, 1H), 7.56 (m, 3H), 7.75 (m, 2H), 7.82 (m, 2H), 7.97 (m, 1H), 8.10 (m, 1H), 8.18 (m, 1H).

Example 78 2-((4-((1H-pyrrolo[2,3-b]pyridin-1-yl)sulfonyl)phenyl)amino)-3-chloronaphthalene-1,4-dione (63)

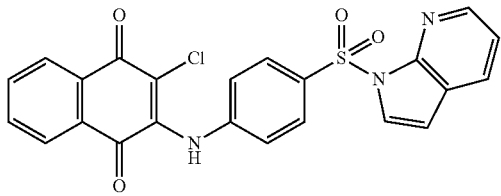 [SMILES: O=C1C(Cl)=C(Nc2ccc(S(=O)(=O)n3ccc4cccnc43)cc2)C(=O)c2ccccc21]

A mixture of 120 (1.20 g, 4.39 mmol) and 2,3-dichloro-1,4-naphthaquinone (1.10 g, 4.83 mmol) was dissolved in EtOH (20 ml) and the mixture was stirred and refluxed for 4 days. The residue was filtered by suction filtration to yield a red product. The residue was filtered without further purification to afford 63 (0.63 g, 30.94%) as a red solid. $^1$H-NMR (300 MHz, DMSO-d$_6$): δ 6.81 (d, =3.9 Hz, 1H), 7.18 (d, J=9.0 Hz, 2H), 7.29 (m, 1H), 7.83 (m, 3H), 8.03 (m, 5H), 8.34 (d, J=1.5 Hz, 1H), 9.55 (s, 1H).

Example 79 2-((4-((1H-pyrrolo[2,3-b]pyridin-1-yl)sulfonyl)phenyl)amino)-3-isopropylnaphthalene-1,4-dione (64)

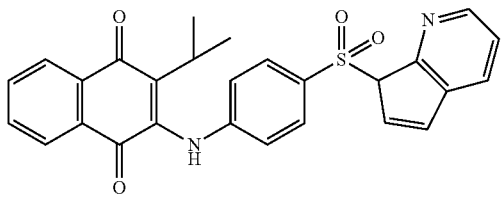 [SMILES: CC(C)C1=C(Nc2ccc(S(=O)(=O)C3C=Cc4cccnc43)cc2)C(=O)c2ccccc2C1=O]

A mixture of 120 (0.30 g, 1.10 mmol) and 2,3-dibromo-1,4-naphthaquinone (0.38 g, 1.21 mmol) was dissolved in EtOH (20 ml) and the mixture was stirred and refluxed for 4 days. The residue was filtered by suction filtration to yield a red product. The residue was then dissolve in EtOH (1.5 ml) and toluene (3 ml) and added Pd(PPh$_3$)$_4$ (0.02 g, 0.02 mmol), 2M K$_2$CO$_3$(aq.) (0.3 ml) and isopropylboronic acid (0.02 g, 0.24 mmol). The reaction was filtered via celite and the solvent removed from the filtrate to yield the oil product. The residue was purified by flash column over silica gel (ethyl acetate:n-Hexane=1:2, Rf=0.55) to afford 64 (0.03 g, 5.78%) as a red product. $^1$H-NMR (300 MHz, CDCl$_3$): δ 1.23 (d, J=6.6 Hz, 6H), 2.56 (qui, J=6.9 Hz, 1H), 6.58 (d, J=3.9 Hz, 1H), 6.97 (d, J=9.0 Hz, 2H), 7.06 (s, 1H), 7.17 (m, 1H), 7.68 (m, 3H), 7.84 (m, 1H), 8.06 (m, 2H), 8.13 (d, J=9.0 Hz, 2H), 8.41 (m, 1H).

Example 80 1-((4-nitrophenyl)sulfonyl)-2,3-dihydro-1H-pyrrolo[2,3-b]pyridine (122)

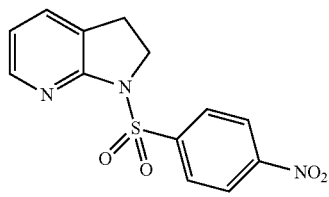 [SMILES: O=[N+]([O-])c1ccc(S(=O)(=O)N2CCc3cccnc32)cc1]

A mixture of 7-azaindoline (0.50 g, 4.16 mmol) was dissolved in DMF (5 ml) and added NaH (0.25 g, 6.24 mmol) and 4-nitrobenzenesulfonyl chloride (0.92 g, 4.16 mmol) was added and the mixture was stirred at room temperature for 0.5 h. The reaction was quenched with water and an extraction was conducted with ethyl acetate (30 ml*3). The organic layer was collected and dried over anhydrous MgSO$_4$ and concentrated in vacuo to yield a yellow product. The residue was purified by flash column over silica gel (ethyl acetate:n-Hexane=1:2, Rf=0.26) to afford 122 (0.21 g, 16.53%) as a yellow solid. $^1$H-NMR (500 MHz, CDCl$_3$): δ 3.09 (t, J=8.5 Hz, 2H), 4.10 (t, J=8.5 Hz, 2H), 6.85-6.87 (m, 1H), 7.39 (d, J=9.0 Hz, 1H), 8.13 (s, 1H), 8.30-8.35 (m, 4H).

Example 81 1-((3-nitrophenyl)sulfonyl)-2,3-dihydro-1H-pyrrolo[2,3-b]pyridine (123)

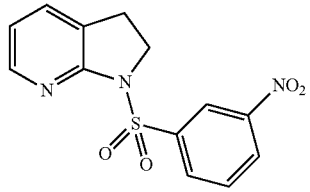 [SMILES: O=[N+]([O-])c1cccc(S(=O)(=O)N2CCc3cccnc32)c1]

A mixture of 7-azaindoline (0.20 g, 1.66 mmol) was dissolved in pyridine (1.5 ml) and 3-nitrobenzenesulfonyl chloride (0.55 g, 2.49 mmol) was added and the mixture was stirred at 50° C. overnight. The reaction was quenched with 3N HCl (aq.) and an extraction was conducted with ethyl acetate (30 ml*3). The organic layer was collected and dried over anhydrous MgSO$_4$ and concentrated in vacuo to yield a yellow product. The residue was purified by flash column over silica gel (ethyl acetate:n-Hexane=1:2, Rf=0.26) to afford 123 (0.30 g, 59.19%) as an orange solid. ¹H-NMR (500 MHz, CDCl₃+CD₃OD): δ 2.95 (t, J=8.0 Hz, 2H), 3.92 (t, J=8.5 Hz, 2H), 6.77 (s, 1H), 7.35 (s, 1H), 7.58 (t, J=8.0 Hz, 1H), 7.90 (d, J=5.5 Hz, 1H), 8.24 (s, 1H), 8.73 (s, 1H).

Example 82 2-chloro-3-((4-((2,3-dihydro-1H-pyrrolo[2,3-b]pyridin-1-yl)sulfonyl)phenyl)amino)naphthalene-1,4-dione (65)

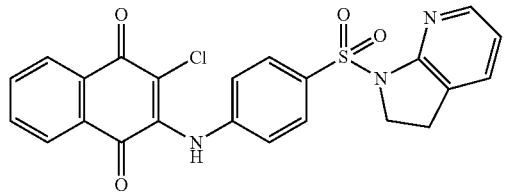

A mixture of 122 (0.20 g, 0.66 mmol) was dissolved in MeOH (10 ml) and 10% Pd/C added as the catalyst and the mixture was stirred under H₂ for h. The 10% Pd/C was filtered and the solvent removed from the filtrate. The residue was filtered without further purification and dissolved in EtOH (15 ml) then added 2,3-dichloro-1,4-naphthaquinone (0.15 g, 0.66 mmol). The reaction was refluxed for 2 days. The residue was purified by flash column over silica gel (ethyl acetate:n-Hexane=1:1, Rf=0.33) to afford 65 (0.02 g, 6.50%) as a red solid. ¹H-NMR (500 MHz, CDCl₃): δ 3.07 (t, J=8.5 Hz, 2H), 4.08 (t, J=9.0 Hz, 2H), 6.82-6.84 (m, 1H), 7.05 (d, J=8.5 Hz, 1H), 7.37 (d, J=7.5 Hz, 1H), 7.65 (d, J=8.5 Hz, 2H), 7.81-7.83 (m, 2H), 7.95-7.97 (m, 1H), 8.08-8.19 (m, 2H), 8.28 (d, J=8.5 Hz, 2H).

Example 83 2-bromo-3-((4-((2,3-dihydro-1H-pyrrolo[2,3-b]pyridin-1-yl)sulfonyl)phenyl)amino)naphthalene-1,4-dione (66)

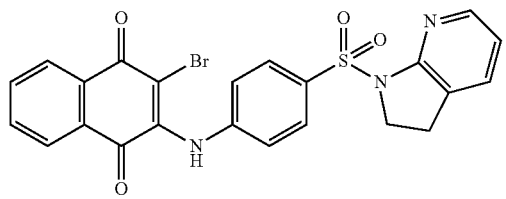 [SMILES: O=C1C(Cl)=C(Nc2ccc(S(=O)(=O)N3CCc4cccnc43)cc2)C(=O)c2ccccc21]

A mixture of 122 (0.14 g, 0.46 mmol) was dissolved in MeOH (15 ml) and 10% Pd/C added as the catalyst and the mixture was stirred under H₂ for 1 h. The 10% Pd/C was filtered and the solvent removed from the filtrate. The residue was filtered without further purification and dissolved in EtOH (15 ml) then 2,3-dibromo-1,4-naphthaquinone (0.15 g, 0.46 mmol) was added. The reaction was refluxed for 2 days. The residue was purified by flash column over silica gel (ethyl acetate:n-Hexane=1:1, Rf=0.33) to afford 66 (0.02 g, 8.52%) as a red solid. ¹H-NMR (500 MHz, CDCl₃): δ 3.07 (t, J=8.5 Hz, 2H), 4.07 (t, J=8.5 Hz, 2H), 6.54 (s, 1H), 6.83-6.85 (m, 1H), 7.34-7.38 (m, 3H), 7.68-7.71 (m, 2H), 7.78 (t, J=7.5 Hz, 1H), 8.10-8.13 (m, 1H), 8.17 (d, J=8.5 Hz, 2H).

Example 84 2-Chloro-3-((3-((2,3-dihydro-1H-pyrrolo[2,3-b]pyridin-1-yl)sulfonyl)-phenyl)amino)naphthalene-1,4-dione (67)

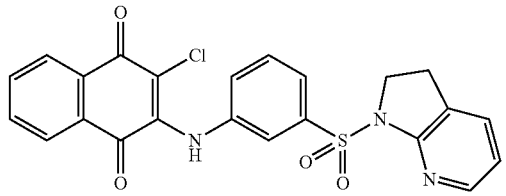 [SMILES: O=C1C(Cl)=C(Nc2cccc(S(=O)(=O)N3CCc4cccnc43)c2)C(=O)c2ccccc21]

A mixture of 123 (0.50 g, 1.64 mmol) was dissolved in IPA/H₂O (16.4 ml) and Fe powder (0.27 g, 4.92 mmol) and NH₄Cl (0.18 g, 3.28 mmol) were added. The reaction was stirred and refluxed for 2 h. The residue was extracted by ethyl acetate (30 ml*3) without further purification to yield the product. The product was dissolved in EtOH (15 ml) then added 2,3-dichloro-1,4-naphthaquinone (0.37 g, 1.64 mmol). The reaction was refluxed for 2 days. The residue was purified by flash column over silica gel (ethyl acetate: n-Hexane=1:1, Rf=0.33) to afford 67 (0.03 g, 3.93%) as a red solid. ¹H NMR (300 MHz, DMSO-d₆): δ 3.02 (t, J=8.7 Hz, 2H), 4.01 (t, J=8.1 Hz, 2H), 6.80 (t, J=6.6 Hz, 1H), 7.20 (d, J=6.9 Hz, 1H), 7.34-7.42 (m, 2H), 7.66-7.76 (m, 3H), 7.81 (d, J=7.5 Hz, 1H), 7.99 (d, J=5.4 Hz, 1H), 8.05 (d, J=6.3 Hz, 1H), 8.11 (d, J=6.0 Hz, 1H).

Example 85 N-(3-nitrobenzyl)pyridin-2-amine (124)

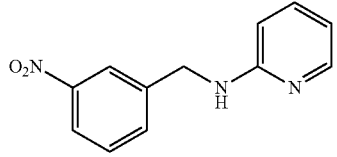 [SMILES: O=[N+]([O-])c1cccc(CNc2ccccn2)c1]

A mixture of 2-aminopyridine (1.1 g, 11.66 mmole) and 3-nitrobenzyl chloride (1.0 g, 5.83 mmol) was dissolved in toluene (30 mL). The reaction was stirred and refluxed under N₂ overnight. The residue was washed with saturated NaHCO₃(aq.) and saturated NaCl (aq.) and then worked up. The product was filtered without further purification to afford 124 (1.50 g, 56.12%). ¹H NMR (300 MHz, CDCl₃): δ 4.66 (d, J=6.0 Hz, 2H), 5.01 (brs, 1H), 6.39 (d, J=8.4 Hz, 1H), 6.60-6.65 (m, 1H), 7.39-7.44 (m, 1H), 7.49 (t, J=7.8 Hz, 1H), 7.70 (d, J=8.1 Hz, 1H), 8.09-8.12 (m, 2H), 8.22 (s, 1H).

Example 86 N-(4-nitrobenzyl)pyridin-2-amine (125)

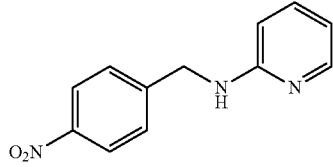 [SMILES: O=[N+]([O-])c1ccc(CNc2ccccn2)cc1]

A mixture of 2-aminopyridine (0.18 g, 1.91 mmol) was dissolved in toluene (3 ml) and 4-nitrobenzyl bromide (0.21 g, 0.96 mmol) was added and the mixture was stirred and refluxed overnight. The residue was purified by flash column over silica gel (ethyl acetate:n-Hexane=1:2, Rf=0.20) to afford 125 (0.12 g, 54.53%) as a pale yellow solid. ¹H NMR (300 MHz, CDCl₃): δ 4.67 (d, J=6.0 Hz, 2H), 5.00 (s, 1H), 6.37 (d, J=8.4 Hz, 1H), 6.61-6.65 (m, 1H), 7.38-7.44 (m, 1H), 7.51 (d, J=8.7 Hz, 2H), 8.09-8.11 (m, 1H), 8.18 (d, J=8.7 Hz, 2H).

Example 87
3-nitro-N-(pyridin-2-yl)benzenesulfonamide (126)

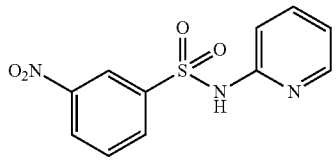 [SMILES: O=[N+]([O-])c1cccc(S(=O)(=O)Nc2ccccn2)c1]

A mixture of 2-aminopyridine (0.18 g, 1.91 mmol) was dissolved in toluene (3 ml) and 3-nitrobenzenesulfonyl chloride (0.47 g, 2.10 mmol) was added and the mixture was stirred and refluxed overnight. The residue was purified by flash column over silica gel (ethyl acetate:n-Hexane=1:2, Rf=0.20) to afford 126 (0.23 g, 43.12%) as a white solid. ¹H NMR (500 MHz, CD₃OD): δ 6.89 (t, J=7.0 Hz, 1H), 7.33 (d, J=9.0 Hz, 1H), 7.79 (t, J=8.0 Hz, 2H), 7.92 (d, J=5.5 Hz, 1H), 8.31 (d, J=7.5 Hz, 1H), 8.40 (d, J=8.0 Hz, 1H), 8.73 (s, 1H).

Example 88 2-Chloro-3-((3-((pyridin-2-ylamino)methyl)phenyl)amino)naphthalene-1,4-dione (68)

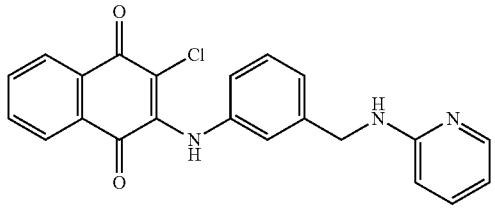 [SMILES: O=C1C(Cl)=C(Nc2cccc(CNc3ccccn3)c2)C(=O)c2ccccc21]

A mixture of 124 (0.44 g, 1.92 mmol), Fe powder (0.32 g, 5.76 mmol) and ammonium chloride (0.21 g, 3.84 mmol) was dissolved in IPA (15.2 ml) and H₂O (3.8 ml) and the mixture was stirred and refluxed for 2 hr. The reaction mixture was filtered, and extracted with dichloromethane, washed and worked up. To the residue, ethanol (3 ml) and 2,3-dichloro-1,4-naphthoquinone (0.19 g, 0.83 mmol) were added and the mixture was refluxed overnight. The solution was evaporated to give a residue, which was purified by flash column over silica gel (EtOAc:n-hexane=2:3) to afford 68 (0.05 g, 15.45%). ¹H NMR (300 MHz, CDCl₃): δ 4.54 (d, =3.6 Hz, 2H), 4.91 (brs, 1H), 6.38 (d, =4.8 Hz, 1H), 6.58-6.61 (m, 1H), 6.98 (d, J=4.5 Hz, 1H), 7.07 (s, 1H), 7.20-7.26 (m, 1H), 7.33-7.36 (m, 1H), 7.38-7.42 (m, 1H), 7.66-7.70 (m, 2H), 7.77 (t, 7ᵓ4.5 Hz, 1H), 8.09-8.12 (m, 2H), 8.19 (d, J=4.5 Hz, 1H).

Example 89 2-Chloro-3-((4-((pyridin-2-ylamino)methyl)phenyl)amino)naphthalene-1,4-dione (69)

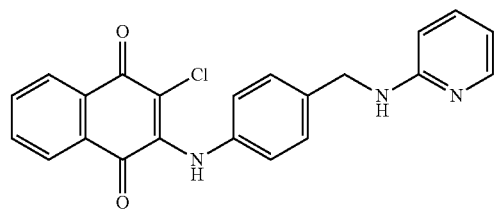 [SMILES: O=C1C(Cl)=C(Nc2ccc(CNc3ccccn3)cc2)C(=O)c2ccccc21]

A mixture of 125 (0.50 g, 2.18 mmol), Fe powder (0.37 g, 6.54 mmol) and ammonium chloride (0.23 g, 4.36 mmol) was dissolved in IPA (17.4 ml) and H₂O (4.4 ml) and the mixture was stirred and refluxed for 2 hr. The reaction mixture was filtered, and extracted with dichloromethane, washed and worked up. To the residue, ethanol (3 ml) and 2,3-dichloro-1,4-naphthoquinone (0.49 g, 2.18 mmol) were added and the mixture was refluxed overnight. The residue was purified by flash column over silica gel (EtOAc:n-hexane=2:3) to afford 69 (0.05 g, 5.88%). ¹H NMR (300 MHz, CDCl₃): δ 4.54 (d, J=3.6 Hz, 2H), 4.88 (brs, 1H), 6.38 (d, J=4.8 Hz, 1H), 6.59-6.62 (m, 1H), 7.05 (d, 7=5.1 Hz, 2H), 7.34 (d, J=5.1 Hz, 2H), 7.40-7.42 (m, 1H), 7.65 (s, 1H), 7.67-7.70 (m, 1H), 7.75-7.78 (m, 1H), 8.11-8.12 (m, 2H), 8.18-8.20 (d, J=3.9 Hz, 1H).

Example 90 3-((3-chloro-1,4-dioxo-1,4-dihydronaphthalen-2-yl)amino)-N-(pyridin-2-yl)benzenesulfonamide (70)

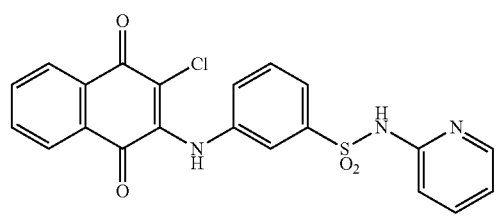 [SMILES: O=C1C(Cl)=C(Nc2cccc(S(=O)(=O)Nc3ccccn3)c2)C(=O)c2ccccc21]

A mixture of 125 (0.50 g, 1.79 mmol), Fe powder (0.30 g, 5.37 mmol) and ammonium chloride (0.19 g, 3.58 mmol) was dissolved in IPA (14.3 ml) and H₂O (3.6 ml) and the mixture was stirred and refluxed for 2 hr. The reaction mixture was filtered, and extracted with dichloromethane, washed and worked up. To the residue, ethanol (3 ml) and 2,3-dichloro-1,4-naphthoquinone (0.41 g, 1.79 mmol) were added and the mixture was refluxed overnight. The residue was purified by flash column over silica gel (EtOAc:n-hexane=2:3) to afford 70 (0.10 g, 12.70%). ¹H NMR (300 MHz, DMSO-d₆): δ 6.84 (d, J=6.6 Hz, 1H), 7.14 (d, J=8.7 Hz, 1H), 7.25-7.29 (m, 1H), 7.46 (t, J=8.1 Hz, 1H), 7.40-7.57 (m, 2H), 7.72-7.66 (m, 1H), 7.82-7.88 (m, 2H), 7.95 (d, J=4.8 Hz, 1H), 8.00-8.04 (m, 2H).

What is claimed is:

1. A compound of Formula (I):

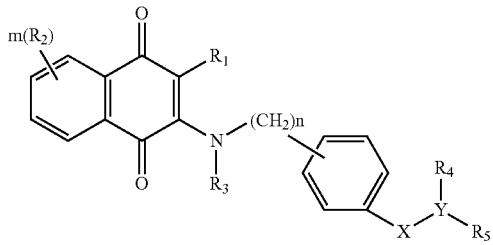

wherein $R_1$ is halogen;

each $R_2$ is the same or different, representing H, $C_{1-10}$alkyl, $C_{2-10}$alkenyl, $C_{2-10}$alkynyl, $NH_2$, $NO_2$, $C_{1-10}$alkyloxy, $C_{1-10}$alkylthio, $C_{1-10}$alkylamino, $C_{1-10}$alkyloxy$C_{1-10}$alkyl, OH or CN, $C_{6-10}$aryl or $C_{5-7}$heterocyclic having 1 to 3 heteroatoms selected from the group consisting of N, O and S;

$R_3$ is H, $C_{1-10}$alkyl, $C_{2-10}$alkenyl, $C_{2-10}$alkynyl, $NH_2$, $NO_2$, OH or CN;

$R_4$ is H, $C_{1-10}$alkyl, $C_{2-10}$alkenyl, $C_{2-10}$alkynyl, $NH_2$, $NO_2$, OH and CN;

$R_5$ is OH, $C_{3-8}$cycloalkyl, phenyl unsubstituted or substituted with one to three same or different substituents selected from OH, CN, halogen, $NH_2$ or $C_{1-4}$alkylpiperazinyl, $C_{1-6}$alkylpiperazinyl, $C_{1-6}$alkylpyridinyl, $C_{1-6}$alkylpyrrolidinyl, pyridinyl, pyrimidinyl, pyrazinyl, piperazinyl, pyrrolidinyl, thiazolyl, benzimidazolyl, pyrazolyl, indazolyl, quinolinyl, indolyl, azaindolyl, azaindazolyl, deazapurinyl, indanyl, morpholinoyl or $C_{1-4}$alkylmorpholinoyl, each of which is unsubstituted or substituted with one, two or three groups selected from OH, CN, halogen $NO_2$, $C_{1-4}$alkyl, or $NH_2$;

and

X is —C(O)

Y is —N—;

m is an integer of 0-3; and n is an integer of 1-7;

or a tautomer, enantiomer, stereoisomer thereof, or a solvate or a pharmaceutically acceptable salt thereof.

2. The compound of claim 1, wherein m is 0; $R_1$ is halogen; n is any integer of 1-4; $R_3$ is H; X is C(O); $R_4$ is H; and $R_5$ is OH, $C_{3-8}$cycloalkyl, phenyl unsubstituted or substituted with one to three same or different substituents selected from OH, CN, halogen, $NH_2$ or $C_{1-4}$alkylpiperazinyl, $C_{1-6}$alkylpiperazinyl, $C_{1-6}$alkylpyridinyl, $C_{1-6}$alkylpyrrolidinyl, pyridinyl, pyrimidinyl, pyrazinyl, piperazinyl, pyrrolidinyl, thiazolyl, benzimidazolyl, pyrazolyl, indazolyl, quinolinyl, indolyl, azaindolyl, azaindazolyl, deazapurinyl, indanyl, morpholinoyl or $C_{1-4}$alkylmorpholinoyl, each of which is unsubstituted or substituted with one, two or three groups selected from OH, CN, halogen or $NH_2$; or a tautomer, enantiomer, stereoisomer thereof, or a solvate or a pharmaceutically acceptable salt thereof.

3. The compound of claim 1, wherein m is 0; $R_1$ is halogen; n is any integer of 1-2; $R_3$ is H; X is C(O); $R_4$ is H; and $R_5$ is OH, $C_{3-8}$cycloalkyl, pyridinyl, phenyl substituted by one to three of $NH_2$, halogen, OH, CN or $C_{1-4}$alkylpiperazinyl; pyrimidinyl unsubstituted or substituted with $NO_2$, $NH_2$ or $C_{1-4}$alkyl; pyrazinyl unsubstituted or substituted with $NO_2$, $NH_2$ or $C_{1-4}$alkyl; thiazolyl unsubstituted or substituted with $NO_2$, $NH_2$ or $C_{1-4}$alkyl; benzimidazolyl unsubstituted or substituted with $NO_2$, $NH_2$ or $C_{1-4}$alkyl; pyrazolyl unsubstituted or substituted with $NO_2$, $NH_2$ or $C_{1-4}$alkyl; indazolyl unsubstituted or substituted with $NO_2$, $NH_2$ or $C_{1-4}$alkyl; quinolinyl unsubstituted or substituted with $NO_2$, $NH_2$ or $C_{1-4}$alkyl; indolyl unsubstituted or substituted with $NO_2$, $NH_2$ or $C_{1-4}$alkyl; -azaindazolyl unsubstituted or substituted with $NO_2$, $NH_2$ or $C_{1-4}$alkyl; deazapurinyl unsubstituted or substituted with $NO_2$, $NH_2$ or $C_{1-4}$alkyl; indanyl unsubstituted or substituted with $NO_2$, $NH_2$ or $C_{1-4}$alkyl; or morpholinoyl unsubstituted or substituted with $NO_2$, $NH_2$ or $C_{1-4}$alkyl; or a tautomer, enantiomer, stereoisomer thereof, or a solvate or a pharmaceutically acceptable salt thereof.

4. The compound of claim 1, which is selected from:
4-(((3-bromo-1,4-dioxo-1,4-dihydronaphthalen-2-yl)amino)methyl)-N-(pyridin-2-yl)benzamide;
4-(((3-chloro-14-dioxo-1,4-dihydronaphthalen-2-yl)amino)methyl)-N-(pyrimidin-4-yl)benzamide;
4-(((3-chloro-1.4-dioxo-1,4-dihydronaphthalen-2-yl)amino)methyl)-N-(pyrazin-2-yl)benzamide;
4-(((3-chloro-1,4-dioxo-1,4-dihydronaphthalen-2-yl)amino)methyl)-N-hydroxybenzamide;
4-(((3-chloro-1,4-dioxo-1,4-dihydronaphthalen-2-yl)amino)methyl)-N-(pyridin-2-yl)benzamide;
N-(2-aminophenyl)-4-(((3-chloro-1,4-dioxo-1,4-dihydronaphthalen-2-yl)amino)methyl)benzamide;
4-(((3-chloro-1,4-dioxo-1,4-dihydronaphthalen-2-yl)amino)methyl)-N-(pyridin-3-yl)benzamide;
4-(((3-chloro-1,4-dioxo-1,4-dihydronaphthalen-2-yl)amino)methyl)-N-(pyridin-4-yl) benzamide;
4-(((3-chloro-1,4-dioxo-1,4-dihydronaphthalen-2-yl)amino)methyl)-N-(3-fluorophenyl)benzamide;
4-(((3-chloro-1,4-dioxo-1,4-dihydronaphthalen-2-yl)amino)methyl)-N-(4-fluorophenyl)benzamide;
4-(((3-chloro-1,4-dioxo-1,4-dihydronaphthalen-2-yl)amino)methyl)-N-phenylbenzamide;
4-(((3-chloro-1,4-dioxo-1,4-dihydronaphthalen-2-yl)amino)methyl)-N-(2-fluorophenyl)benzamide;
4-(((3-chloro-1,4-dioxo-1,4-dihydronaphthalen-2-yl)amino)methyl)-N-(thiazol-2-yl)benzamide;
N-(1H-benzo[d]imidazol-2-yl)-4-(((3-chloro-1,4-dioxo-1,4-dihydronaphthalen-2-yl)amino)methyl)benzamide;
4-(((3-chloro-1,4-dioxo-1,4-dihydronaphthalen-2-yl)amino)methyl)-N-(4-hydroxyphenyl) benzamide;
4-(((3-chloro-1,4-dioxo-1,4-dihydronaphthalen-2-yl)amino)methyl)-N-(3-ethynylphenyl) benzamide;
4-(((3-chloro-1,4-dioxo-1,4-dihydronaphthalen-2-yl)amino)methyl)-N-(2-fluoro-4-iodophenyl)benzamide;
N-(1H-benzo[d]imidazol-5-yl)-4-((3-chloro-1,4-dioxo-1,4-dihydronaphthalen-2-ylamino) methyl)benzamide;
4-((3-chloro-1,4-dioxo-1,4-dihydronaphthalen-2-ylamino)methyl)-N-cyclopropylbenzamide;
4-((3-chloro-1,4-dioxo-1,4-dihydronaphthalen-2-ylamino)methyl)-N-cyclopentylbenzamide;
4-((3-chloro-1,4-dioxo-1,4-dihydronaphthalen-2-ylamino)methyl)-N-(1H-indazol-5-yl)benzamide;
4-((3-chloro-1,4-dioxo-1,4-dihydronaphthalen-2-ylamino)methyl)-N-(5-methylthiazol-2-yl)benzamide;
4-((3-chloro-1,4-dioxo-1,4-dihydronaphthalen-2-ylamino)methyl)-N-(5-methyl-3H-pyrazol-3-yl)benzamide;
4-((3-chloro-1,4-dioxo-1,4-dihydronaphthalen-2-ylamino)methyl)-N-(3-nitropyridin-4-yl) benzamide;
4-((3-chloro-1,4-dioxo-1,4-dihydronaphthalen-2-ylamino)methyl)-N-(quinolin-6-yl)benzamide;

4-((3-chloro-1,4-dioxo-1,4-dihydronaphthalen-2-ylamino)methyl)-N-(quinolin-8-yl)benzamide;

4-((3-chloro-1,4-dioxo-1,4-dihydronaphthalen-2-ylamino)methyl)-N-(quinolin-3-yl)benzamide;

4-((3-chloro-1,4-dioxo-1,4-dihydronaphthalen-2-ylamino)methyl)-N-(quinolin-5-yl)benzamide;

4-((3-chloro-1,4-dioxo-1,4-dihydronaphthalen-2-ylamino)methyl)-N-(2-methylquinolin-4-yl)benzamide;

4-((3-chloro-1,4-dioxo-1,4-dihydronaphthalen-2-ylamino)methyl)-N-(1H-indol-5-yl)benzamide;

4-((3-chloro-1,4-dioxo-1,4-dihydronaphthalen-2-ylamino)methyl)-N-(2-methyl-1H-indol-5-yl)benzamide;

4-((3-chloro-1,4-dioxo-1,4-dihydronaphthalen-2-ylamino)methyl)-N-(1H-indol-7-yl) benzamide;

4-((3-chloro-1,4-dioxo-1,4-dihydronaphthalen-2-ylamino)methyl)-N-(1H-indol-4-yl)benzamide;

4-((3-chloro-1,4-dioxo-1,4-dihydronaphthalen-2-ylamino)methyl)-N-(4-(4-ethylpiperazin-1-yl)phenyl)benzamide;

4-((3-chloro-1,4-dioxo-1,4-dihydronaphthalen-2-ylamino)methyl)-N-(1H-indazol-6-yl)benzamide;

4-((3-chloro-1,4-dioxo-1,4-dihydronaphthalen-2-ylamino)methyl)-N-(1H-pyrrolo[2,3-b]pyridin-5-yl)benzamide;

4-((3-chloro-1,4-dioxo-1,4-dihydronaphthalen-2-ylamino)methyl)-N-(1H-pyrazolo[3,4-b]pyridin-5-yl)benzamide;

4-((3-chloro-1,4-dioxo-1,4-dihydronaphthalen-2-ylamino)methyl)-N-(7-methyl-7H-pyrrolo[2,3-d]pyrimidin-4-yl)benzamide; and 4-((3-chloro-1,4-dioxo-1,4-dihydronaphthalen-2-ylamino)methyl)-N-(2,3-dihydro-1H-inden-4-yl)benzamide;

or a tautomer or stereoisomer thereof, or a solvate or a pharmaceutically acceptable salt thereof.

5. The compound of claim 1, which is 4-(((3-chloro-1,4-dioxo-1,4-dihydronaphthalen-2-yl)amino)methyl)-N-(pyridin-4-yl)benzamide, having the following formula:

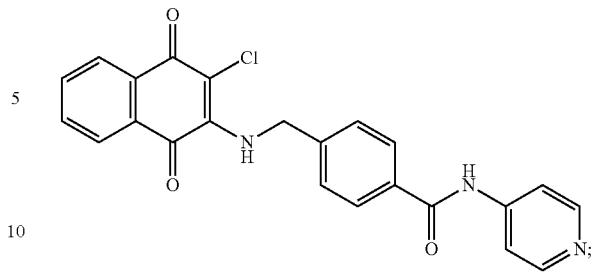

or a tautomer, enantiomer, stereoisomer thereof, or a solvate or a pharmaceutically acceptable salt thereof.

6. A pharmaceutical composition, comprising a compound of claim 1 and a pharmaceutically acceptable carrier.

7. The pharmaceutical composition of claim 6, further comprising a second therapeutic agent.

8. The pharmaceutical composition of claim 7, wherein the second therapeutic agent is selected from a mitotic inhibitor, vinca alkaloids and vepesid; an anthracycline antibiotic; a nucleoside analog; an EGFR inhibitor; a folate antimetabolite; cisplatin, carboplatin or an HDAC inhibitor.

9. The pharmaceutical composition of claim 7, wherein the second therapeutic agent is selected from a corticosteroid, a keratolytic agent, a vitamin $D_3$ derivative, PUVA and anthralin, $\beta_2$-agonist, immunosuppressant, NSAID, COX-2 inhibitor, non-steroidal calcineurin inhibitor, steroidal anti-inflammatory agent, 5-amino salicylic acid, DMARD, hydroxychloroquine sulfate, inflammatory modulator, agent that interferes with B cell action or penicillamine.

10. A method for therapeutically treating multiple myeloma or colorectal adenocarcinoma, comprising administrating an effective amount of the compound of claim 1 to a cell or a subject.

11. A method for reducing tumor volume growth relative to vehicle control in a cancer selected from breast cancer or ovarian cancer in a subject in need thereof, the method comprising administering to the subject a compound of claim 1.

* * * * *

UNITED STATES PATENT AND TRADEMARK OFFICE
CERTIFICATE OF CORRECTION

| | |
|---|---|
| PATENT NO. | : 10,577,328 B2 |
| APPLICATION NO. | : 15/746964 |
| DATED | : March 3, 2020 |
| INVENTOR(S) | : Yun Yen, Jing-Ping Liou and Shiow-Lin Pan |

It is certified that error appears in the above-identified patent and that said Letters Patent is hereby corrected as shown below:

On the Title Page

At (71), please delete "TAIPEI MEDICAL UNIVERSITY," and correct the Applicant to CALGENT BIOTECHNOLOGY CO., LTD.

Signed and Sealed this
Twenty-third Day of August, 2022

Katherine Kelly Vidal
*Director of the United States Patent and Trademark Office*